(12) United States Patent
Powis

(10) Patent No.: US 6,689,775 B2
(45) Date of Patent: Feb. 10, 2004

(54) USES OF THIOREDOXIN

(75) Inventor: Garth Powis, Tuscon, AZ (US)

(73) Assignee: Arizona Board of Regents, acting on behalf of the University of Arizona, Tuscon, AZ (US)

(*) Notice: Subject to any disclaimer, the term of this patent is extended or adjusted under 35 U.S.C. 154(b) by 145 days.

(21) Appl. No.: 09/875,578

(22) Filed: Jun. 6, 2001

(65) Prior Publication Data

US 2002/0055131 A1 May 9, 2002

Related U.S. Application Data

(63) Continuation of application No. 09/319,292, filed as application No. PCT/US97/22292 on Dec. 5, 1997, now abandoned.
(60) Provisional application No. 60/031,995, filed on Dec. 6, 1996.

(51) Int. Cl.$^7$ .............................................. A61K 31/545
(52) U.S. Cl. ........................ 514/208; 514/183; 424/9.1; 424/9.361; 435/7.1
(58) Field of Search ................................. 514/208, 183; 435/7.1; 424/9.1, 9.361

(56) References Cited

FOREIGN PATENT DOCUMENTS

| WO | WO 91 04320 | 4/1991 |
|---|---|---|
| WO | 97-22292 | 12/1997 |

OTHER PUBLICATIONS

Gura. Science, 1997, 278:1041–1042.*
Jain. Sci. Am., 1994, 271:58–65.*
Curti. Crit. Rev. in Oncology/Hematology, 1993, 14:29–39.*
Hartwell et al. Science, 1997, 278:1064–1068.*
Kirkpatrick, DL et al, 1998, Biochem pharmacol, 55:987–994.*
Mau, BL et al, 1992, Biochem Pharmacol, 43: 1613–1620.*
Schallreuter, KU et al, 1990, Biochem Biophys Acta, 1054: 14–20.*
Powis et al, 1994, Oncology Res, 6 (10–11): 539–44.*
Gasdaska, PY et al, 1994, Biochem Biophys Acta, 1218:292–296.*
Gasdaska, PY et al, 1995, Cell Growth Differ, 6:1643–1650.*
Baker, A., et al..: "Thioredoxin, a gene found overexpressed in human cancer"Cancer Research 57(22):5162–5167 (1997).
Powis, G., et al.: "Selenium and the Thioredoxin Redox System" Oncology Research 9(6–7):303–312 (1997).
Gallegos, A., et al.: "Trausfection with human thioredoxin increases cell proliferation and a dominant–negative mutant thioredoxin reverses the transformed phenotype of human breast cancer cells" Cancer Research 56(24):5765–5770 (1996).

Berggren, M., et al.: "Thioredoxin and Thioredoxin Reductase Gene Expression in Human Tumors and Cell Lines" Anticancer Research 16:3459–66, XP002062159 (Nov.–Dec. 1996).
Tockman,et al.: Cancer Research (Suppl) 52: 2715–2718 (1992).
Oblong, J.E.: Cancer Chemoth Pharmacol, 34:434–438 (1994).
Gura: Science 278:1041–1042 (1997).
Jain: Sci. Am, 271:58–65 (1994).
Gasdaska, J.R.: Biochem Pharmacol; 52:1741–1747 (1996).
Hartwell, et al: Science: 278:1064–1068 (1997).
Kirkpatrick, D.L., "Mechanisms of Inhibition of the Thioredoxin Growth Factor System by Antitumor 2–Imidazolyl Disulfides" Biochemical Pharmacology: 55: 987–996 (1998).
Kirkpatrick, D. L., et al., "Stimulation of Apoptis by a Redox Active Disulfide" Proc. Am. Assocation, Cancer Res., 36 (1995): 2541.
Drexler, et al. Leukemia and Lymphoma, 9:1–25 (1993).
Emblcton, et al.: Immunol. Ser. 23:181–207 (1984).
Curti, et al.,: Crit. Rev. in Oncology/Hematology, 14:29–39 (1993).
Mustafa O., et al.: International Journal of Oncology, 8(5):883–888 (1996).
Freshney: Culture of Animal Cells, a Manual of Basic Technique, Alan R. Liss, Inc., p. 4 (1983).
Powls, G., et al.: Thioredoxin Redox Signalling: a Novel Target for Anti–Cancer Drug Development, Anti–Cancer Drugs, 7:121–126 (1996).
Mau, D. L., et al.. Biochem. Pharmacol., 43:1613–1620 (1992).
Schallreuter, K.U. , Biochem Biophys Acta, 1504: 14–20 (1990).
Powis, et al., Oncology Research, 0 (10–11):539–44.
Gadaska, P.Y., et al.: Biochem Biophys ACTA 1218:292–296 (1994).

* cited by examiner

Primary Examiner—Susan Ungar
Assistant Examiner—Minh Tam Davis
(74) Attorney, Agent, or Firm—Raymond A. Miller; Pepper Hamilton LLP

(57) ABSTRACT

The present invention relates to the use of thioredoxin as, inter alia, a cell growth stimulator, as well as a screen for agents that are useful in reducing or preventing thioredoxin-associated apoptosis inhibition and agents that are useful in inhibiting thioredoxin stimulated cell growth.

3 Claims, 33 Drawing Sheets

23.3 –

10.6 –

8.1 –

1 2 3 4

Figure 1:
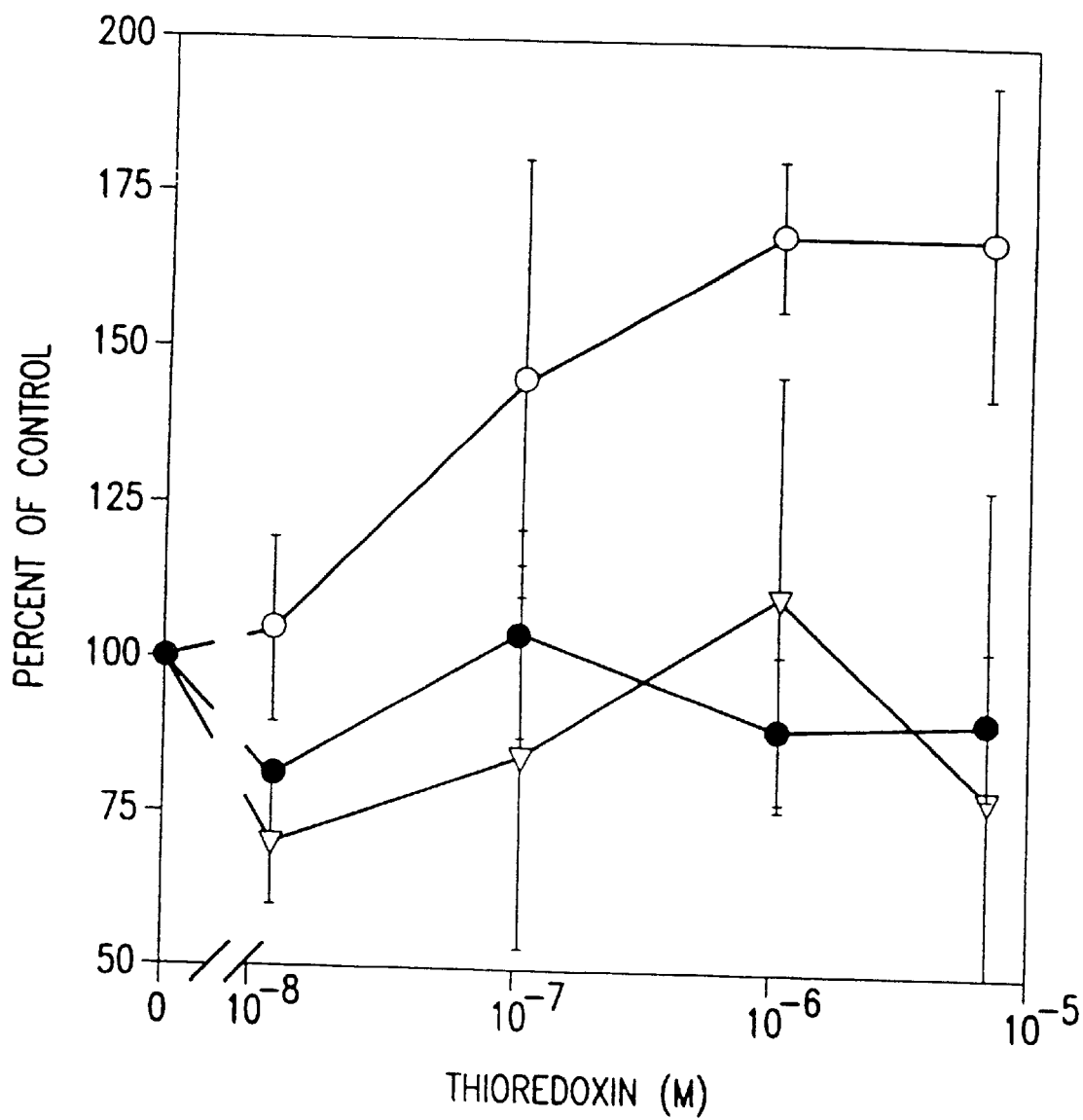

FIG.20B(1) 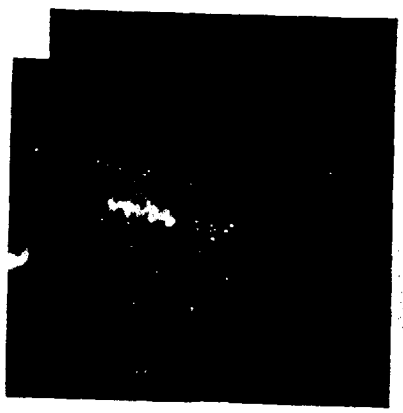 FIG.20B(2) 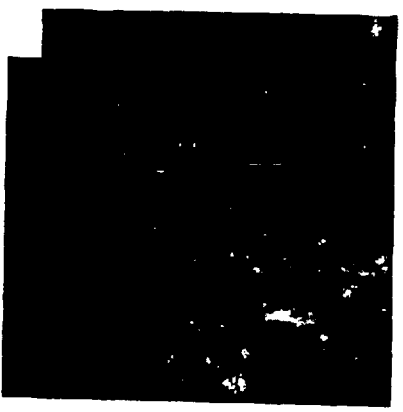
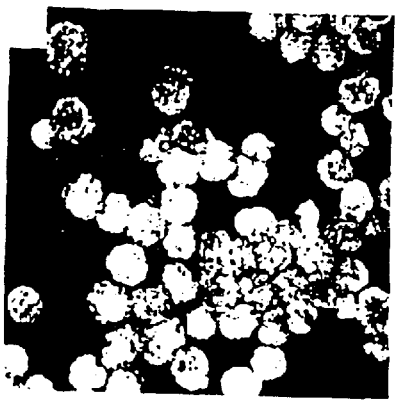 
FIG.20B(3) FIG.20B(4)
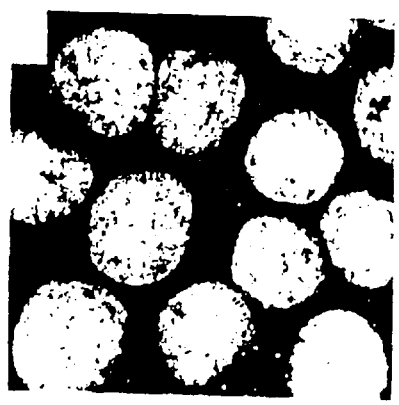 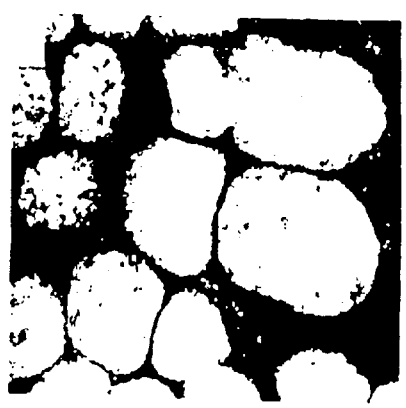
FIG.20C(1) FIG.20C(2)

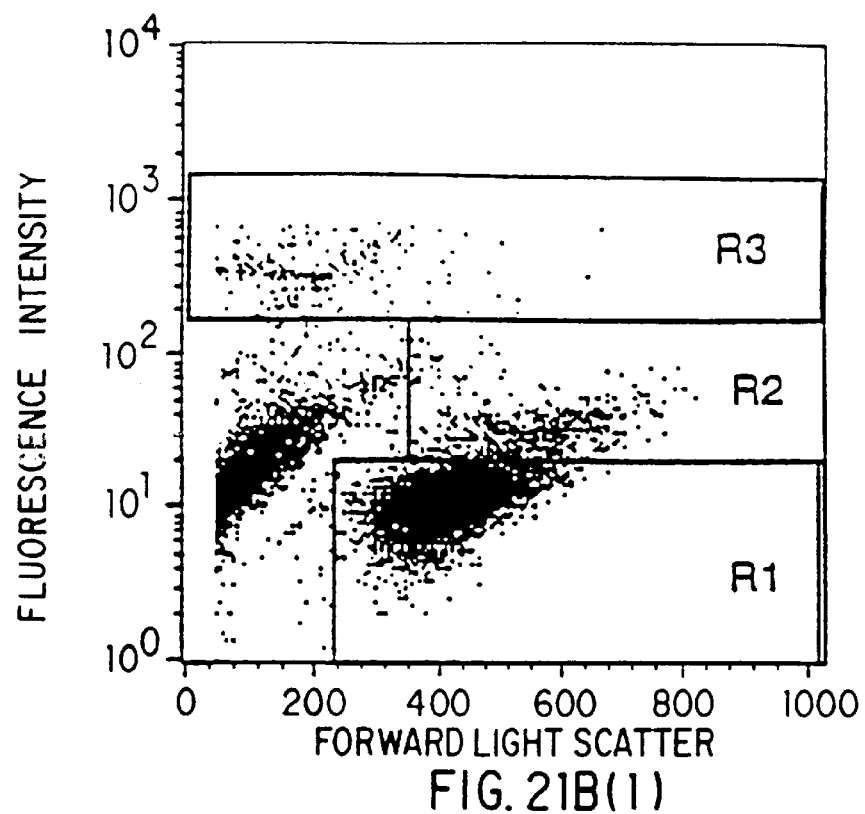
FIG. 21B(1)
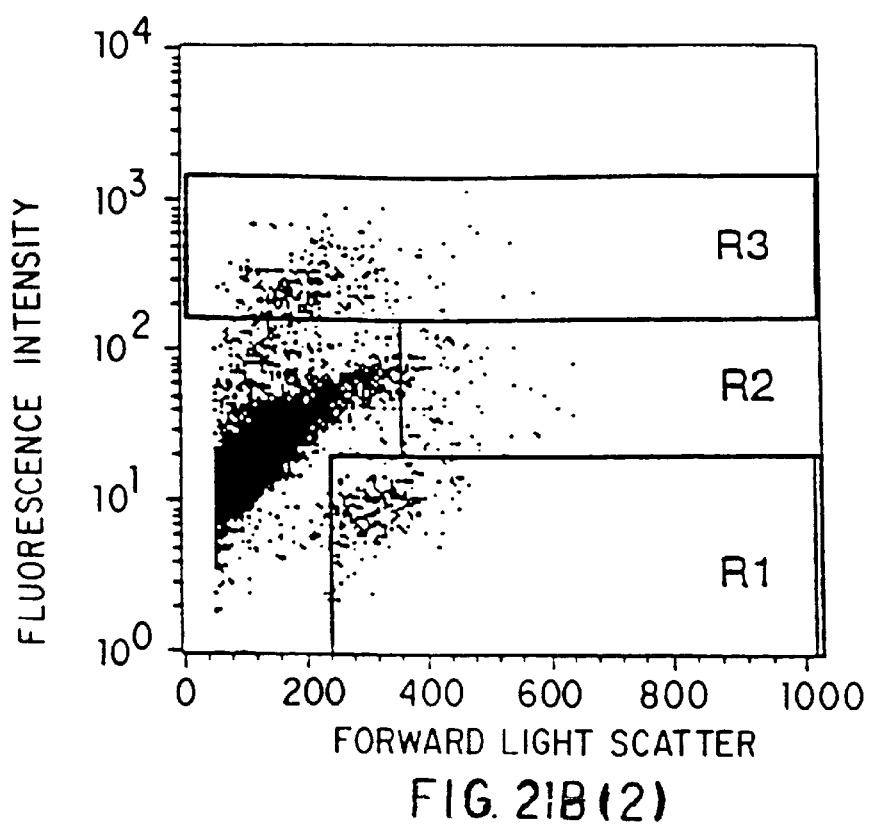
FIG. 21B(2)

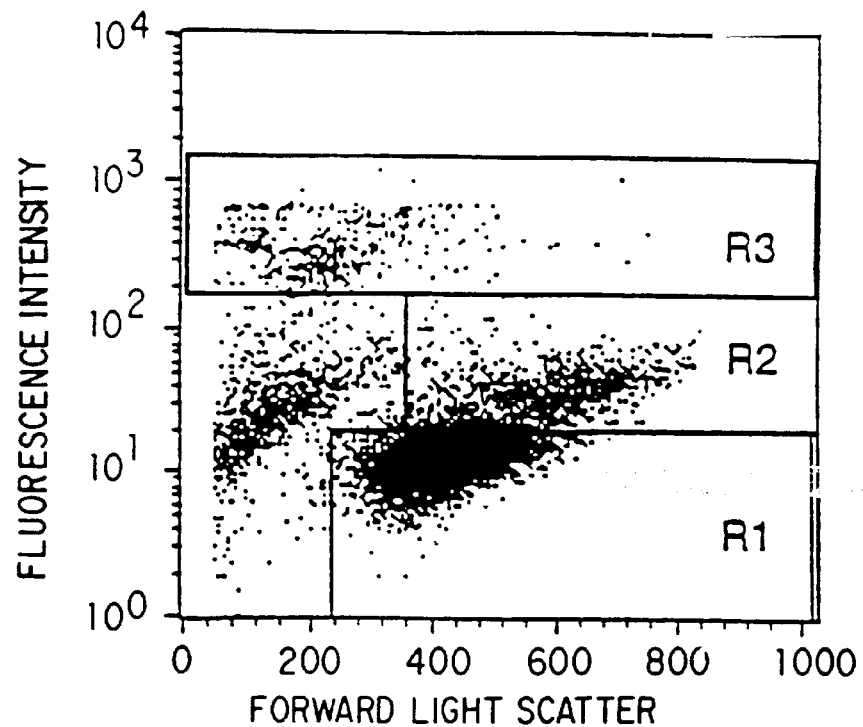
FIG. 21B(3)
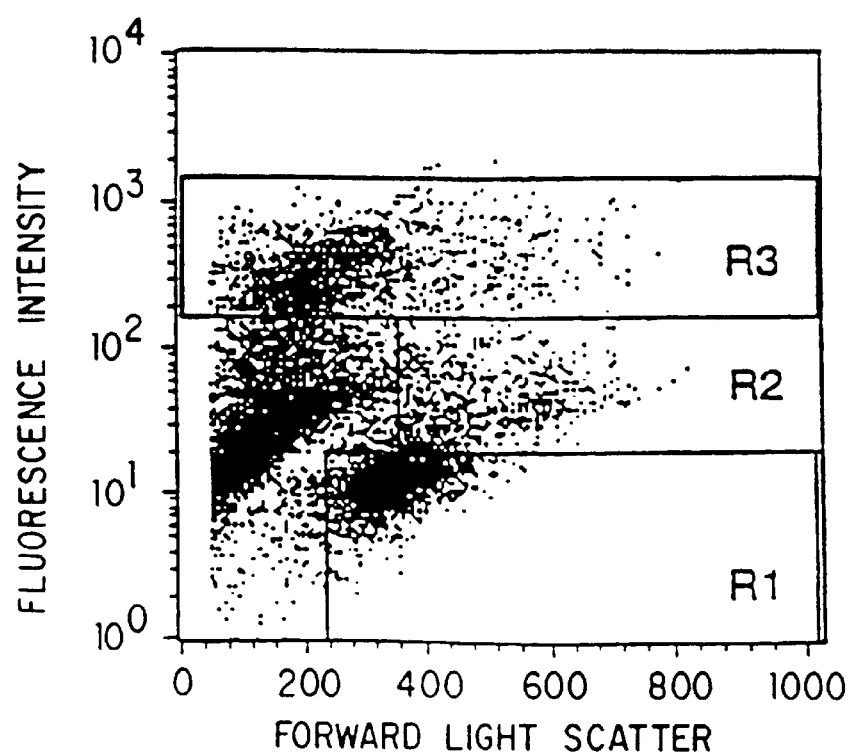
FIG. 21B(4)

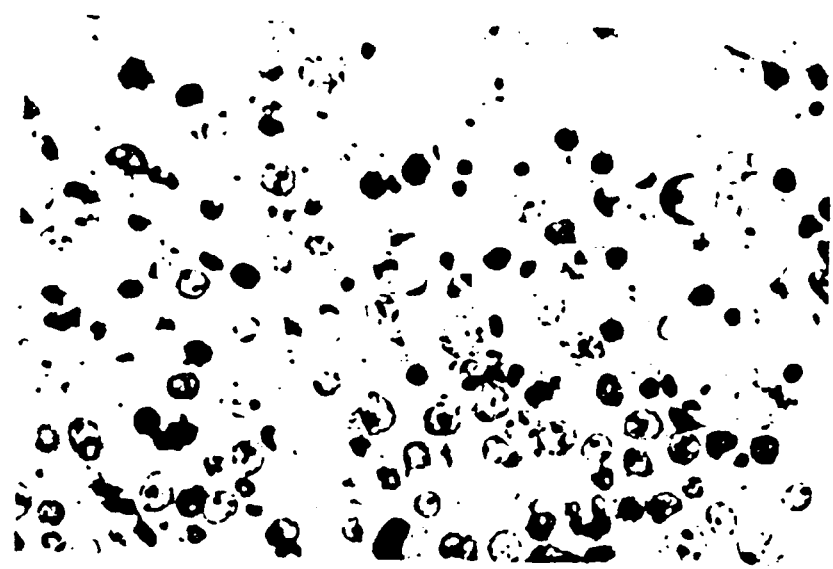
FIG.22B(1)
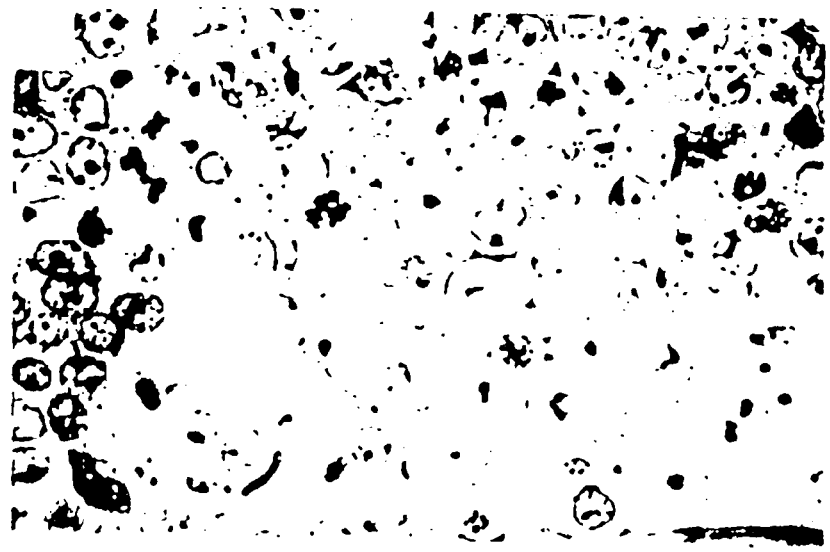
FIG.22B(2)

FIG.24A
FIG.24C
FIG.24B
FIG.24D

USES OF THIOREDOXIN

CROSS REFERENCE TO RELATED APPLICATIONS

This is a continuation of application U.S. Ser. No. 09/319,292, filed on Jun. 3, 1999, now abandoned, which is a national phase filing based on International Application No. PCT/US97/22292, filed on Dec. 5, 1997, which claimed the benefit of priority from U.S. Provisional Patent Application Serial No. 60/031,995, filed on Dec. 6, 1996.

STATEMENT REGARDING FEDERAL SPONSORSHIP

This invention was made with support from the U.S. government under a grant from the U.S. National Institutes of Health, contract number CA48725. The U.S. government has certain rights in the invention.

1. BACKGROUND OF INVENTION

The present invention generally relates to the use of thioredoxin as, inter alia, a cell growth stimulator, as well as a screen for agents that are useful in reducing or eliminating thioredoxin-associated apoptosis inhibition and agents that are useful in inhibiting thioredoxin stimulated cell growth.

Thioredoxin is a low molecular weight ($M_r$ 11,000–12,000) redox protein found in both prokaryotic and eukaryotic cells. (Holmgren A., J. Biol. Chem., 264:13963–13966, 1989), that undergoes reversible thiol reduction by the NADPH-dependent enzyme thioredoxin reductase. Human thioredoxin, which has 5 cysteine (Cys) residues, is a 11.5 kDa protein with 27% amino acid identity to $E.\ coli$ thioredoxin. Human thioredoxin contains 3 additional Cys residues not found in bacterial thioredoxin that give it unique biological properties. (Gasdaska P Y, et al., Biochem. Biophys. Acta., 1218:292–296, 1994). Cys32 and Cys35 are the conserved catalytic site cysteine residues that undergo reversible oxidation to cystine. Cys92, Cys69 and Cys73 are found in mammalian but not in bacterial thioredoxins. Cys73 appears to be particularly important for maintaining the biological activity of thioredoxin in an oxidizing environment. Thioredoxin reduces a variety of intracellular proteins including enzymes such as ribonucleotide reductase which is important for DNA synthesis, and critical Cys residues in transcription factors such as NF-κB, AP-1 and the glucocorticoid receptor, thus, altering their binding to DNA. In addition to its intracellular actions, human thioredoxin has remaskable eztracellular celm growth stimulating properties. It has been reported (Gasdaska P Y, et al., Biochem. Biophys. Acta., 1218:292–296, 1994) that thioredoxion is identical to a growth factor reported to be secreted by human HTLV-1 transformed leukemia cell lines (Fox J A, et al., Proc.Natl. Accd. Sci. USA, 84:2663–2677, 1987). It has also been found that human recombinant thioredoxin will stimulate the growth of a wide variety of fibroblast and human solid tumor cell lines in culture (Gasdaska J R, et al., Cell Growth Differ., 6:1643–1650, 1995; Oblong J E, et al., J. Biol. Chem., 269:11714–11720, 1994). $E.\ coli$ thioredoxin does not stimulate cell proliferation.

Thioredoxin was first studied for its ability to act as reducing co-factor for ribonucleotide reductase, the first unique step in DNA synthesis. (Laurent T C, et al., 15 J. Biol. Chem., 239:3436–3444, 1964). More recently thioredoxin has been shown to exert redox control over a number of transcription factors modulating their binding to DNA and thus, regulating gene transcription. Transcription factors regulated by thioredoxin include NF-κB (Matthews J R, et al., Nucl. Acids Res., 20:3821–3830, 1992), TFIIIC (Cromlish J A, et al., J. Biol. Chem., 264:18100–18109, 1989), BZLFI (Bannister 20 A J, et al., Oncogene, 6:1243–1250, 1991), the glucocorticoid receptor (Grippo J F, et al., J. Biol. Chem., 258:13658–13664, 1983) and, indirectly through a nuclear redox factor Ref-1/HAPE, thioredoxin can regulate AP-1 (Fos/Jun heterodimer) (Abate C, et al., Science 249:1157–1161, 1990). Thioredoxin is also a growth factor with a unique mechanism of action.

Human thioredoxin has been sequenced and cloned. (Gasdaska P Y, et al., Biochem. Biophys. Acta., 1218:292–296, 1994; Deiss L P, et al., Science 252:117–120, 1991). It has been shown that the deduced amino acid sequence of thioredoxin is identical to that of a previously known protein called eosinophil cytotoxicity stimulating factor (Silberstein D S. et al. J. Biol. Chem. 268:9138–9142, 1993) or adult T-cell leukemia-derived factor (ADF) (Gasdaska P Y, et al., Biochem. Biophys. Acta., 1218:292–296, 1994). ADF has been reported to be secreted by virally transformed leukemic cell lines and to stimulate their growth (Yodoi J, et al., Adv. Cancer Res., 57:381–411, 1991). These observations have been extended to show that human recombinant thioredoxin stimulates the proliferation of both normal fibroblasts and a wide variety of human solid and leukemic cancer cell lines. (Gasdaska J R, et al., Cell Growth Differ., 6:1643–1650, 1995); Powis G, et al., Oncol. Res., 6:539–544, 1994; Oblong J E, et al., J. Biol. Chem., 269:11714–11720, 1994). It has been shown that thioredoxin stimulates cell proliferation by increasing the sensitivity of the cells to growth factors secreted by the cells themselves. (Gasdaska J R, et al., Cell Growth Differ., 10 6:1643–1650, 1995).

Recombinant modified thioredoxins, otherwise called mutant thioredoxins, have been developed, but no indications of uses were known in the art for any particular mutant form. In a wild type thioredoxin, the cysteine (Cys) residues at the conserved -Cys32-Gly-Pro-Cys35-Lys active site of thioredoxin undergo reversible oxidation-reduction catalyzed by the NADPH-dependent flavoprotein thioredoxin reductase. (Luthman M, et al., Biochem., 21:6628–6633, 1982). It has been reported that mutation of the active site Cys32 and Cys35 residues to serine (Ser) residues, either singly or together (C32S/C35S thioredoxin), results in a compound that is redox inactive (i.e., it is not a substrate for reduction by thioredoxin reductase) and that does not stimulate cell proliferation (Oblong J E, et al., J. Biol. Chem., 269:11714–11720, 1994).

Thioredoxin mRNA has been found to be over expressed by some human tumor cells (Gasdaska P Y, et al., Biochem. Biophys. Acta., 1218:292–296, 1994; Grogan T, et al., Cancer Res., 1997, in press) and since it is secreted from cells by a leaderless secretary pathway (Rubartelli A. et al., J. Biol. Chem., 267:24161–24164, 1992) it could be a growth factor for some human cancers (Gasdaska J R, et al., Cell Growth Differ., 6:1643–1650, 1995). However, the mechanism for cell growth stimulation by thioredoxin mRNA has been examined and found not to promote cell growth. Recombinant human thioredoxin is not taken up by cells and does not bind to high affinity cell surface receptors but appears to enhance the sensitivity of cells to endogenously produced or other growth factors, a mechanism termed voitocrine (Greek, voithos =helper) (Gasdaska J R, et al., Cell Growth Differ., 6:1643–1650, 1995).

The in vitro cell growth stimulating activity of human thioredoxin has been previously reported for human lymphoid and solid tumor cancer cells (Gasdaska J R, et al., Cell Growth Differ., 6:1643–1650, 1995; Oblong J E, et al., J. Biol. Chem., 269:11714–11720, 1994) and for mouse fibroblast cells (Oblong J E, et al., J. Biol. Chem., 269:11714–11720, 1994). The production of a Cys$^{73}$→Ser mutant thioredoxin has been previously reported. In one study it did not act like wild-type thioredoxin as a component of a complex cell growth stimulating factor called "early pregnancy factor" (Tonissen K, 10 et al., J. Biol. Chem., 268:22485–22489, 1993). In another study it was reported that Cys$^{73}$→Ser mutant thioredoxin did not form a dimer, but cell growth stimulating activity by the mutant thioredoxin was not investigated in this study (Ren X, et al., Biochem., 32:9701–9705, 1993). However, the ability of the Cys73→Ser mutant and other mutant thioredoxins to stimulate cell proliferation has not been reported There have been no prior reports of administration of mutant thioredoxins in vivo.

It has been known that certain human tumor cells were found to over-express thioredoxin mRNA compared to normal lung tissue from the same subject. (Gasdaska P Y, et al., Biochem. Biophys. Acta., I 218:292–296, 1994). It has also been known that human primary colorectal tumors have exhibited elevated levels of thioredoxin mRNA compared to normal colonic mucosa (Berggren M, et al., Anticancer Res., 16:3459–3466, 1996). It has not been known that thioredoxin protein was present in certain human tumor cells, and it has not been known that thioredoxin protein played any role in preventing or enhancing tumor cell growth.

While thioredoxin itself is known, its use in identifying agents that inhibit cell growth stimulated by thioredoxin has not been previously shown.

Human thioredoxin reductase has been characterized as a protein (Oblong J E, et al., Biochem., 32:7271–7277, 1993). In addition, the general properties and the cDNA base sequence of human thioredoxin reductase is known in the art. However, it has not been disclosed or suggested in the art that thioredoxin reductase be used as an anti-tumor drug target.

The myelodysplastic syndromes (MDS) are a heterogeneous class of life threatening diseases characterized by ineffective hematopoiesis and progressive, reractory cytopenia (List A F, et al., J. Clin. Oncol., 8:1424–1441, 1990). Transformation to acute leukemia may occur in one-third of the patients, The underlying defect is decreased multilineage progenitor cell growth associated with decreased sensitivity to growth factor stimulation (Merchav S, et al., Leukemia, 5:340–346, 1991). Very high doses of recombinant granulocyte-macrophage colony stimulating factor (GM-CSF) and recombinant human granulocyte colony stimulating factor (G-CSF) can ameliorate neutropenia but do not improve red blood cell or platelet function (List A F, et al., J. Clin. Oncol., 8:1424–1441, 1990). Although IL-3 displays multilineage progenitor stimulatory effects in normal marrow clinical trials have shown limited ability to improve hematopoiesis in MDS (List A F, et al., Blood, 82 (Suppl. 1):377a, 1993). Thus, current treatment for MD is limited by the ability of cytokines to stimulate hematopoietic progenitor cells and the decreased sensitivity of these cells to growth factors.

2. SUMMARY OF THE INVENTION

The present invention relates to the use of thioredoxin as, inter alia, a cell growth stimulator, as well as a screen for agents that are useful in reducing or preventing thioredoxin-associated apoptosis inhibition in tumor cells and agents that are useful in inhibiting thioredoxin stimulated growth of tumor cells.

A non-limiting embodiment of the invention involves a method of inhibiting tumor cell growth in a tumor cell that over-expresses thioredoxin comprising contacting said tumor cell with a cell growth inhibiting effective amount of an inhibitor of thioredoxin expression. Such agents can include, inter alia, small molecular compounds that complex with and interfere with the biological action of thioredoxin, preferably those that complex with active Cys residues, antisense inhibitors of thioredoxin expression, antibodies, or inhibitors of nucleic acid expression.

A further non-limiting embodiment of the invention involves a method of reducing inhibition of apoptosis in tumor cells that over-express thioredoxin comprising contacting said tumor cells with an effective amount of an agent that inhibits thioredoxin. Such agents can include, inter alia, antibodies to this redoxin, compounds that inhibit the activity of this redoxin, preferably those that inhibit the activity of active Cys residues in the protein, cross-linking agents and the like.

A further non-limiting embodiment of the invention involves a method of identifying an agent that inhibits tumor cell growth in cells that over-express thioredoxin comprising measuring thioredoxin expression or activity in a first sample of said cells; contacting a second sample of said cells with an agent to be tested; measuring expression or activity of thioredoxin in said second sample; comparing expression or activity of thioredoxin in said first sample and said second sample; whereby a decrease in expression or activity of thioredoxin in said second sample is indicative of an agent that inhibits tumor cell growth.

A further non-limiting embodiment of the invention involves a method of identifying an agent that reduces inhibition of apoptosis in a tumor cell that over-expresses thioredoxin comprising measuring thioredoxin expression or activity in a first sample of said cells; contacting a second sample of said cells with an agent to be tested; measuring expression or activity of thioredoxin in said second sample; comparing expression or activity of thioredoxin in said first sample and said second sample; whereby a decrease in expression or activity of thioredoxin in said second sample is indicative of an agent that reduces inhibition of apoptosis.

A further non-limiting embodiment of the invention involves a method of identifying an agent that reduces thioredoxin induced inhibition of apoptosis in a tumor cell growth.

A further non-limiting embodiment of the invention involves a method of stimulating cell growth comprising introducing a nucleic acid encoding a human thioredoxin having Ser at amino acid reside 73 under conditions whereby said nucleic acid is expressed.

A further non-limiting embodiment of the invention involves a composition comprising an agent that is useful in reducing or eliminating thioredoxin-associated apoptosis inhibition and an acceptable carrier.

A further non-limiting embodiment of the invention involves a composition comprising an agent that is useful in inhibiting thioredoxin stimulated cell growth and an acceptable carrier.

The present invention is based, at least in part, on the discovery that thioredoxin protein is over-expressed in certain human tumor cells; that thioredoxin stimulates the growth of cancer cells; that thioredoxin inhibits apoptosis; that thioredoxin is over-expressed in some human primary tumors and is correlated with increased tumor cell growth and decreased apoptosis; and that agents that inhibit thioredoxin also have anti-tumor activity.

The present invention involves the new uses of thioredoxin, thioredoxin reductase, and mutant forms of thioredoxin for use in screening for anti-tumor agents. It has not been known in the art to use thioredoxin and/or thioredoxin reductase in a screening assay for anti-thioredoxin and/or anti-thioredoxin reductase agents for use as anti-tumor compounds.

The present invention further relates to the use of thioredoxin and/or thioredoxin reductase antibodies for use as anti-tumor agents.

The present invention further relates to the use of anti-sense thioredoxin or anti-sense thioredoxin reductase compounds for use as anti-tumor agents.

The present invention further relates to the use of thioredoxin nucleic acid probes and/or thioredoxin antibodies in a diagnostic assay for certain cancers.

The present invention further relates to the use of thioredoxin as a target for agents to be used in combination with existing and new treatment therapies, such as drugs and radiation, that reduce or prevent the thioredoxin-induced inhibition of apoptosis in tumor cells or to increase the sensitivity of tumor cells to these modalities.

In addition, mutant forms of thioredoxin provide proteins with additional growth stimulating activity.

These and still further objects as shall hereinafter appear are readily fulfilled by the present invention in an unexpected manner as will be readily discerned from the following detailed description of the preferred embodiments of the invention, especially when read in conjunction with the accompanying drawings.

In contrast to the present invention, none of the above cited references teach or suggest the use of thioredoxin protein according to the claimed invention.

3. BRIEF DESCRIPTION OF THE DRAWINGS

FIG. 1 shows a chart that illustrates the stimulation of human bone marrow colony formation by Cys73→Ser mutant thioredoxin in accordance with the present invention, wherein the effects of Cys73→Ser thioredoxin on colony formation are shown by (o) multilineage progenitors (CFU-GEMM); (●) erythroid progenitors (BFU-E); and (∇) myeloid progenitors (CFU-GM), measured over 10 days as described (Values represent the mean of 4 determinations and bars represent S.D.)

Figure 2:
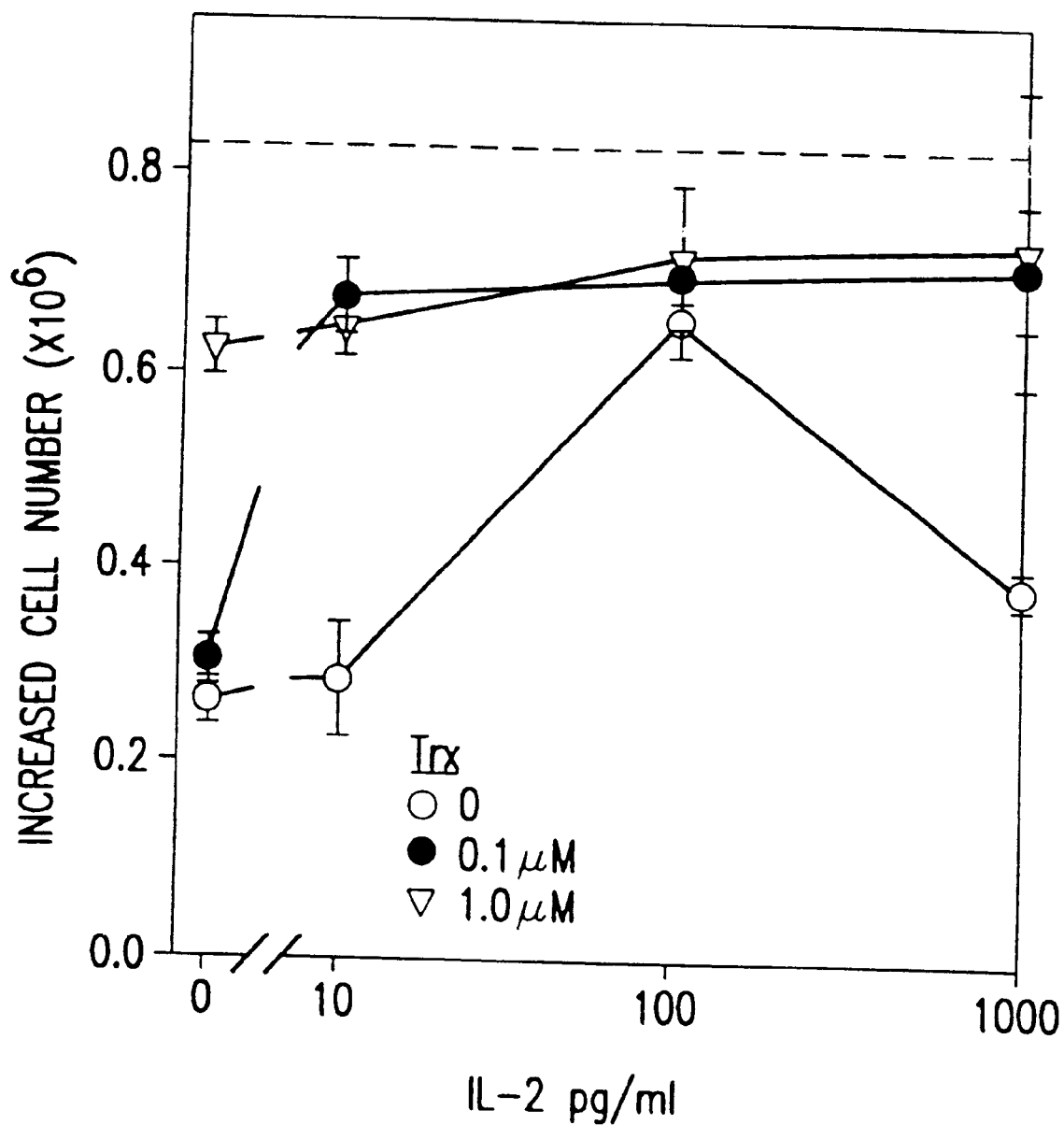

FIG. 2 shows a chart that illustrates potentiation of IL-2 induced MCF-7 breast cancer cell growth by Cys73→Ser mutant thioredoxin in accordance with the present invention, wherein cells were growth arrested for 48 hr. in medium with 0.5% serum ($10^5$ cells) then stimulated in the absence of medium with either IL-2 or $Cys^{32}$→Ser mutant thioredoxin at the concentrations shown and cell number was measured after 48 hr. (Each point represents the mean of 3 determinations and bars represent S.E., and the dotted line shows stimulation by 10% serum.)

Figure 3:
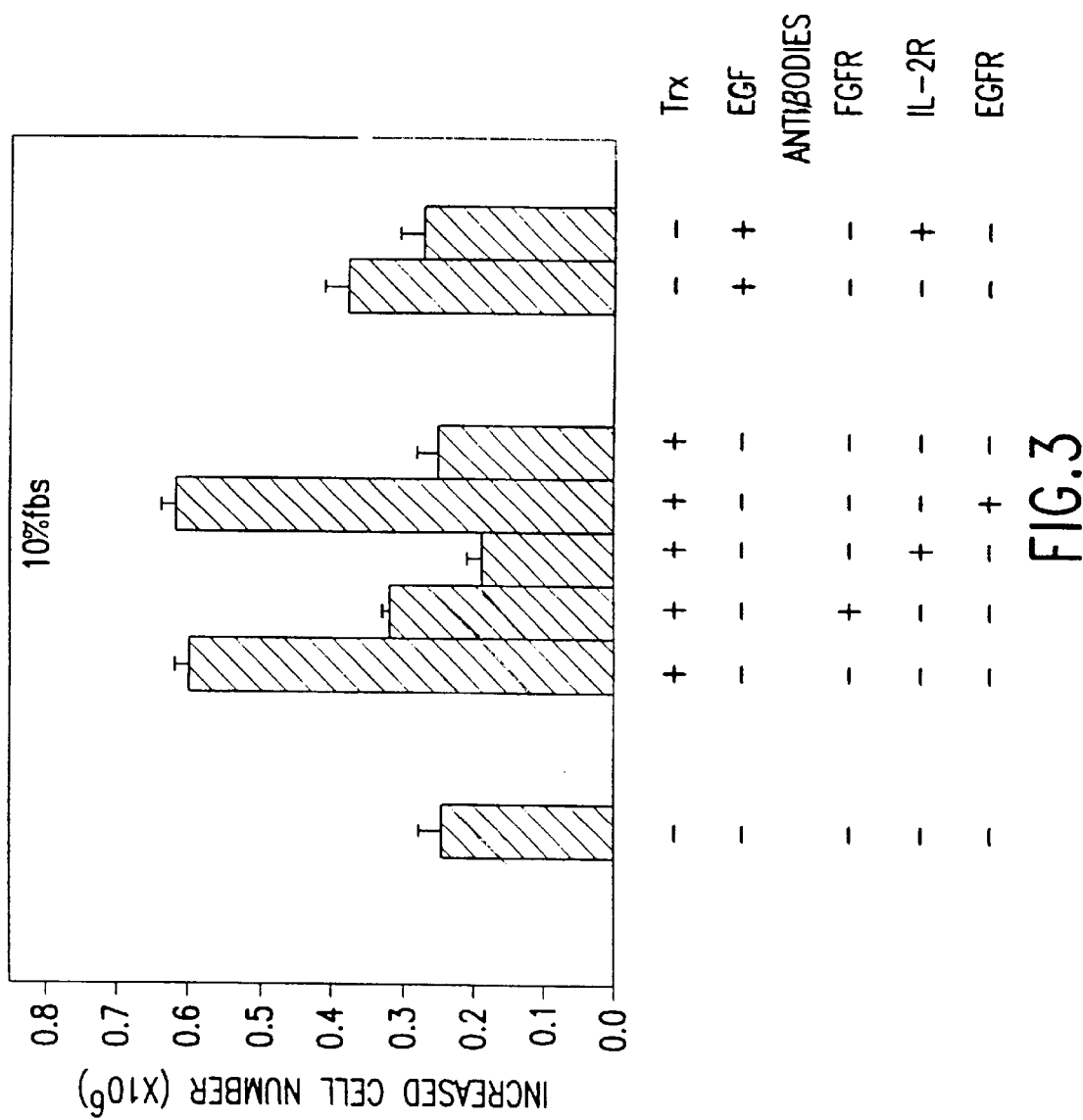

FIG. 3 shows a chart that illustrates the inhibition of thioredoxin stimulated MCF-7 cell growth by receptor antibodies in accordance with the present invention, wherein cell proliferation was measured as described in FIG. 2; the concentrations of agents used were Cys73→Ser mutant thioredoxin (Thioredoxin) 1 μM, monoclonal antibodies to FGF receptor, IL-2-receptor and EGF-receptor 4 μg/ml, and EGF 10 nM; and the EGF and EGFR were added as a negative control. (Values represent the mean of 3 determinations and bars represent S.E., and the dotted line shows the effect of 10% serum alone.)

Figure 4A:
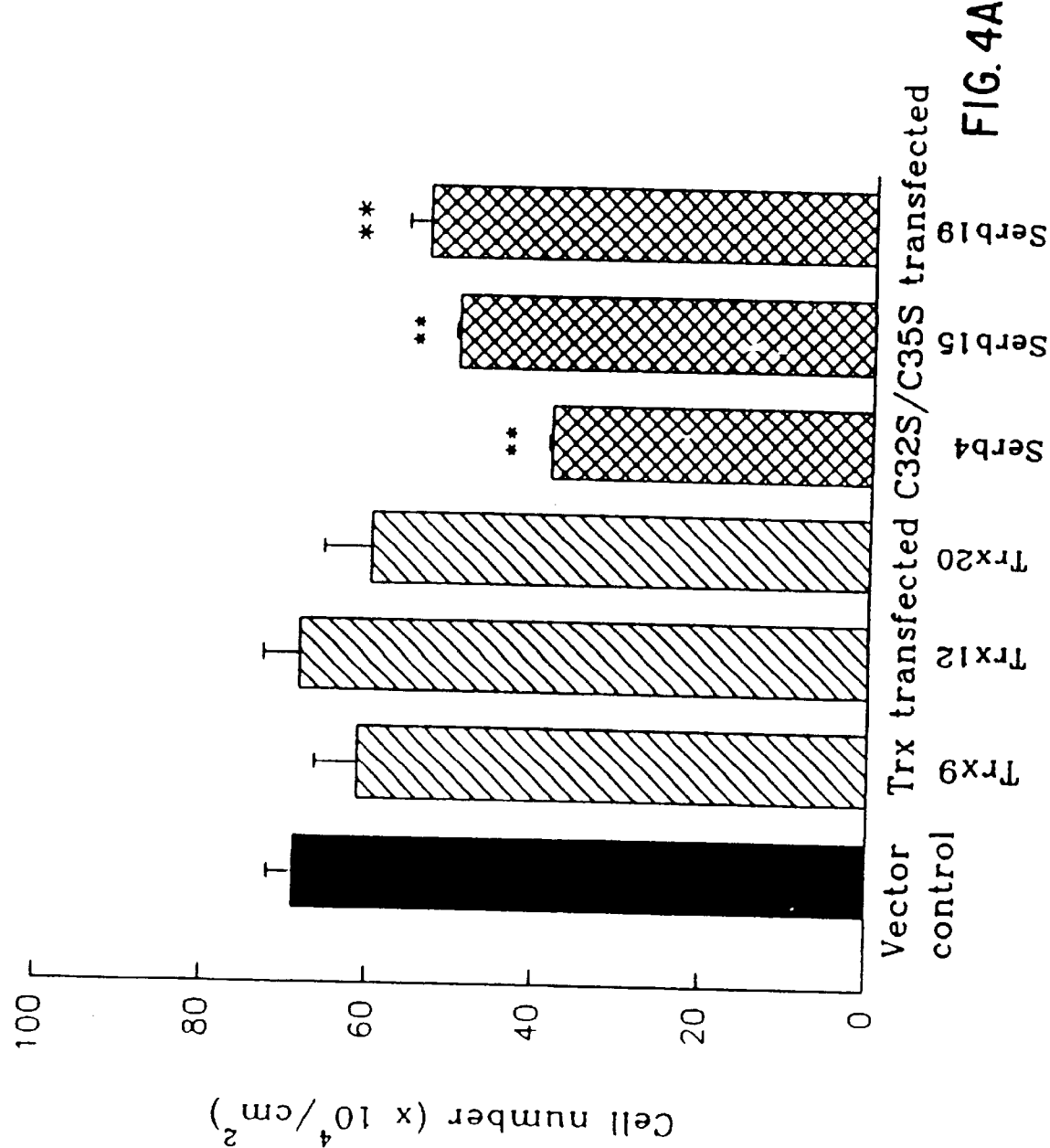
Figure 4B:
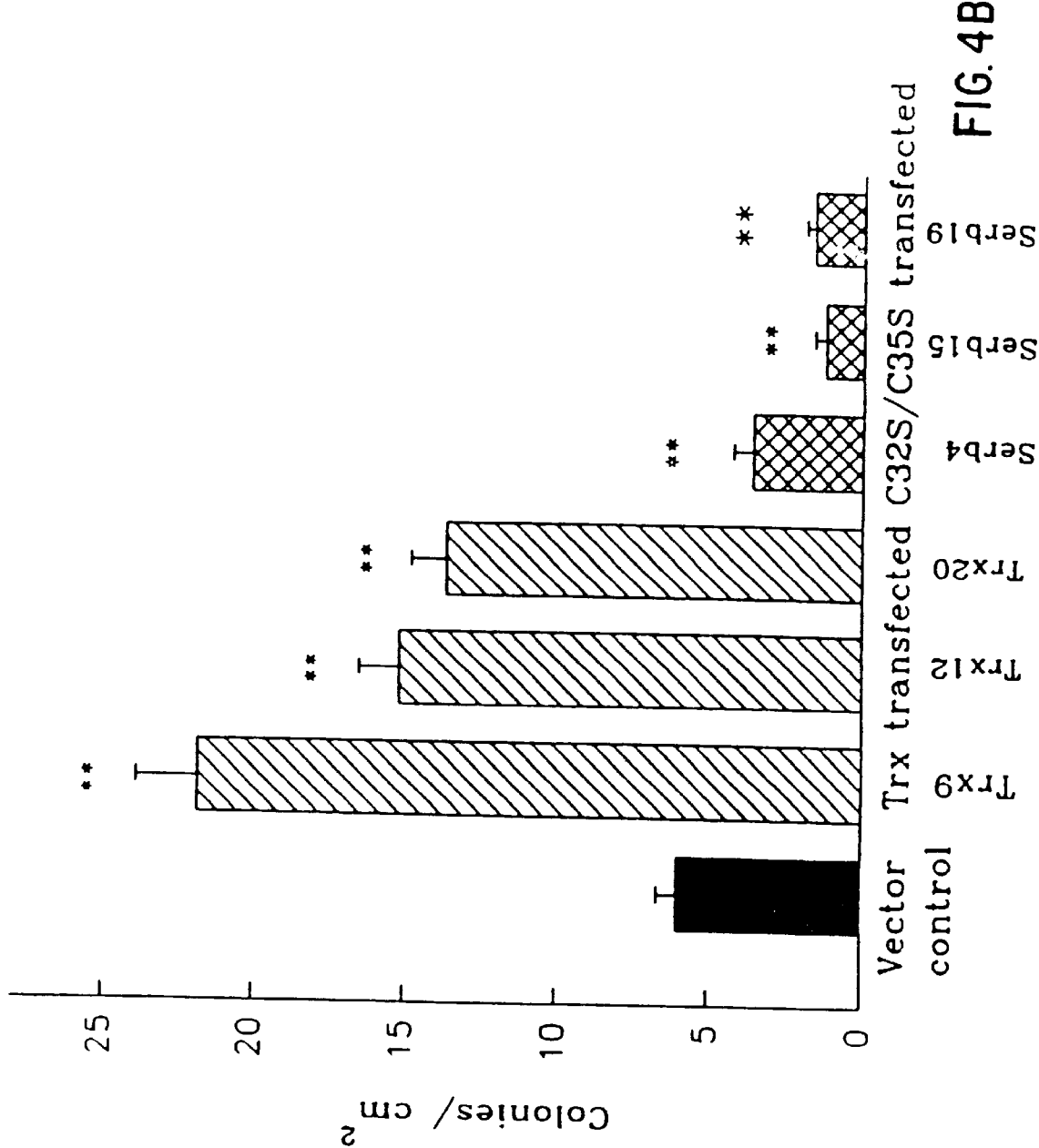

FIGS. 4A–B illustrate comparative charts showing the effects of thioredoxin and C32S/C35S cDNA transfection on proliferation of MCF-7 cells. In FIG. 4A, $3 \times 10^4$ cells were plated in 3.8 $cm^2$ plastic culture dishes in DMEM with 10% fbs and cell number measured 7 days later. In FIG. 413, $10^4$ cells were plated in 2 $cm^2$ wells containing soft agarose and colonies measuring >60 microns counted 7 days later. (Control, the Neol vector alone transfected MCF-7 cells; Thioredoxin 9, Thioredoxin 12, and Thioredoxin 20, MCF-7 cells transfected with human Thioredoxin cDNA; Serb 4, Serb 15, and Serb 19, MCF-7 cells transfected with C32S/C35S cDNA. Values are the mean of 3 determinations and bars are S.E. **indicates p <0.01 compared to vector-alone transfected cells.)

Figure 5:
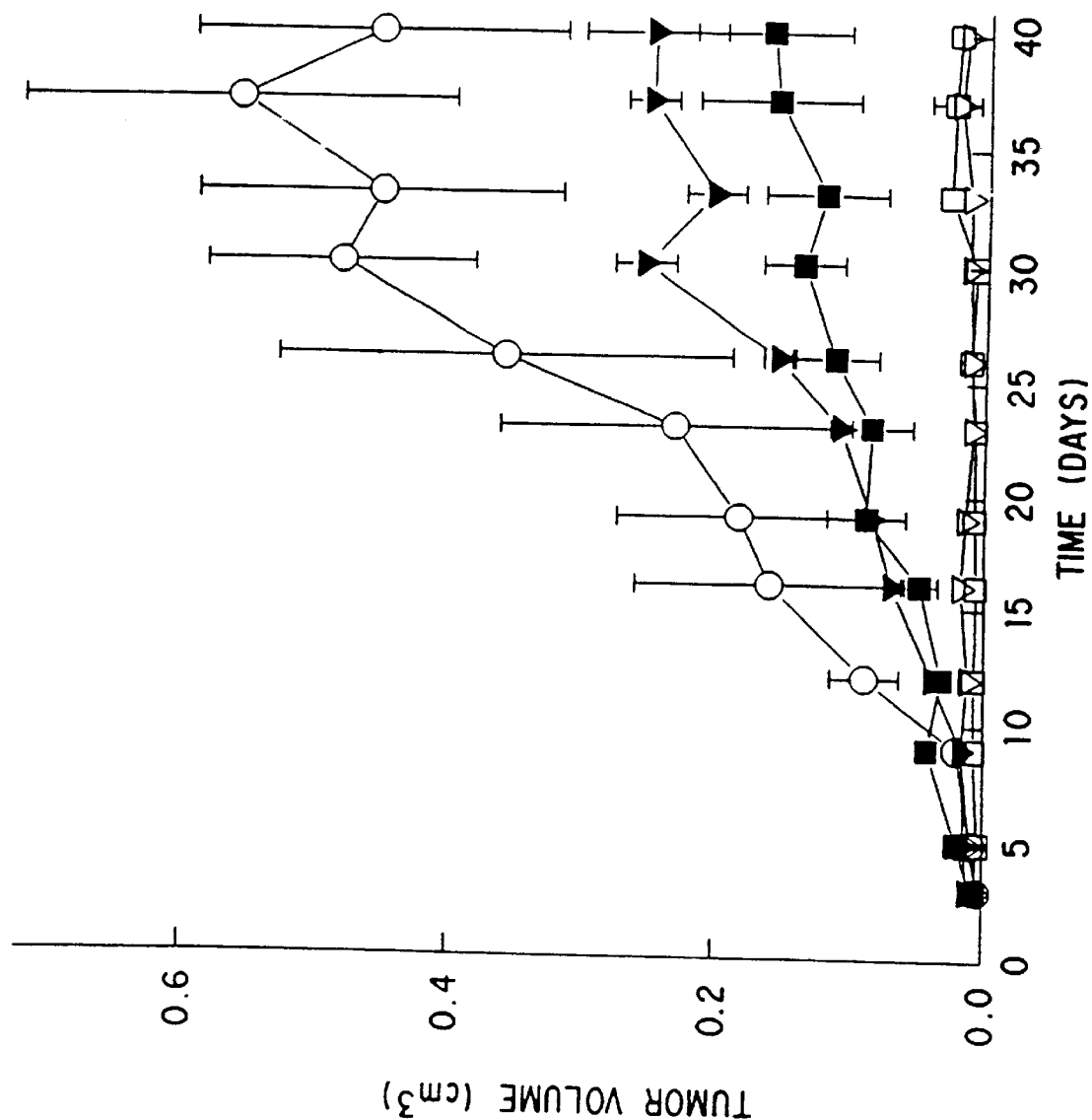

FIG. 5 illustrates a chart showing the growth of Trx and C32S/C35S-transfected MCF-7 breast cells in Scid mice. Female Scid mice implanted s.c. 2 days previously with a 21 day release pellet of 0.25 mg 17-β estradiol were injected subcutaneously with $2 \times 10^6$ transfected MCF 7 cells in 0.1 ml 0.9% NaCl and 0.1 ml matrigel. (o) represents MCFneo, pDC304 vector-alone transfected MCF 7 cells; (▼) represents Trx 12, thioredoxin transfected cells; (■) represents Trx 20, thioredoxin transfected cells; (∇) represents Serb 4, C32S/C35S transfected cells; and (□) represents Serb 15, C32S/C35S transfected cells. There were 4 mice per group. Tumor growth was measured twice a week for 40 days. The 17-β-estradiol pellet was replaced at 21 days. Values are mean and bars, SE.

Figure 6:
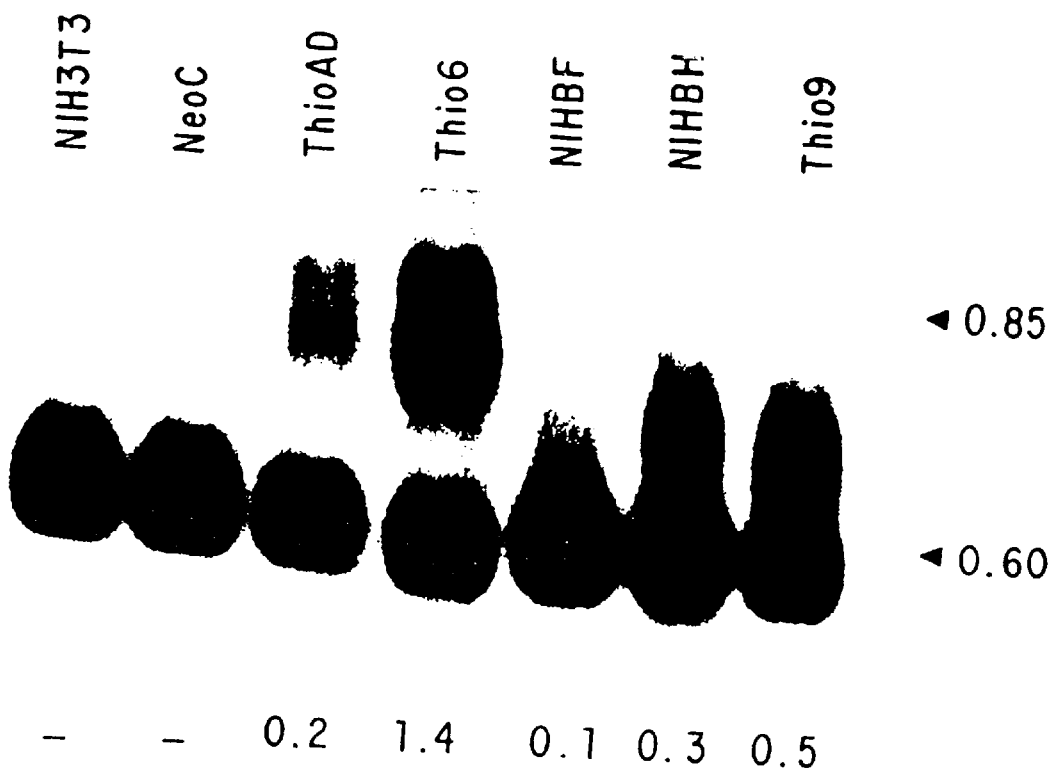

FIG. 6 illustrates an autoradiogram showing Northern analysis of NIH 3T3 cells stably transfected with cDNA for human Trx and a redox-inactive mutant human Trx (C32S/C35S) hybridized with a full-length $^{32}$P-labeled human Trx cDNA. The bottom band is endogenous mouse Trx mRNA, and the top band is the transfected human Trx mRNAs. The blots illustrate columns of NIH 3T3. wild-type NIH 3T3 cells; NeoC, cells transfected with the pRXneo vector; ThioAD and Thio6, cells transfected with C32S/C35S Trx in the pDC304neo vector; and Thio 9, cells transfected with human Trx cDNA in the pDC304neo vector. Values on right are molecular weight markers (in kb). Values below are the ratios of transfected Trx mRNA to endogenous Trx mRNA determined by phosphorimager analysis.

Figure 7:
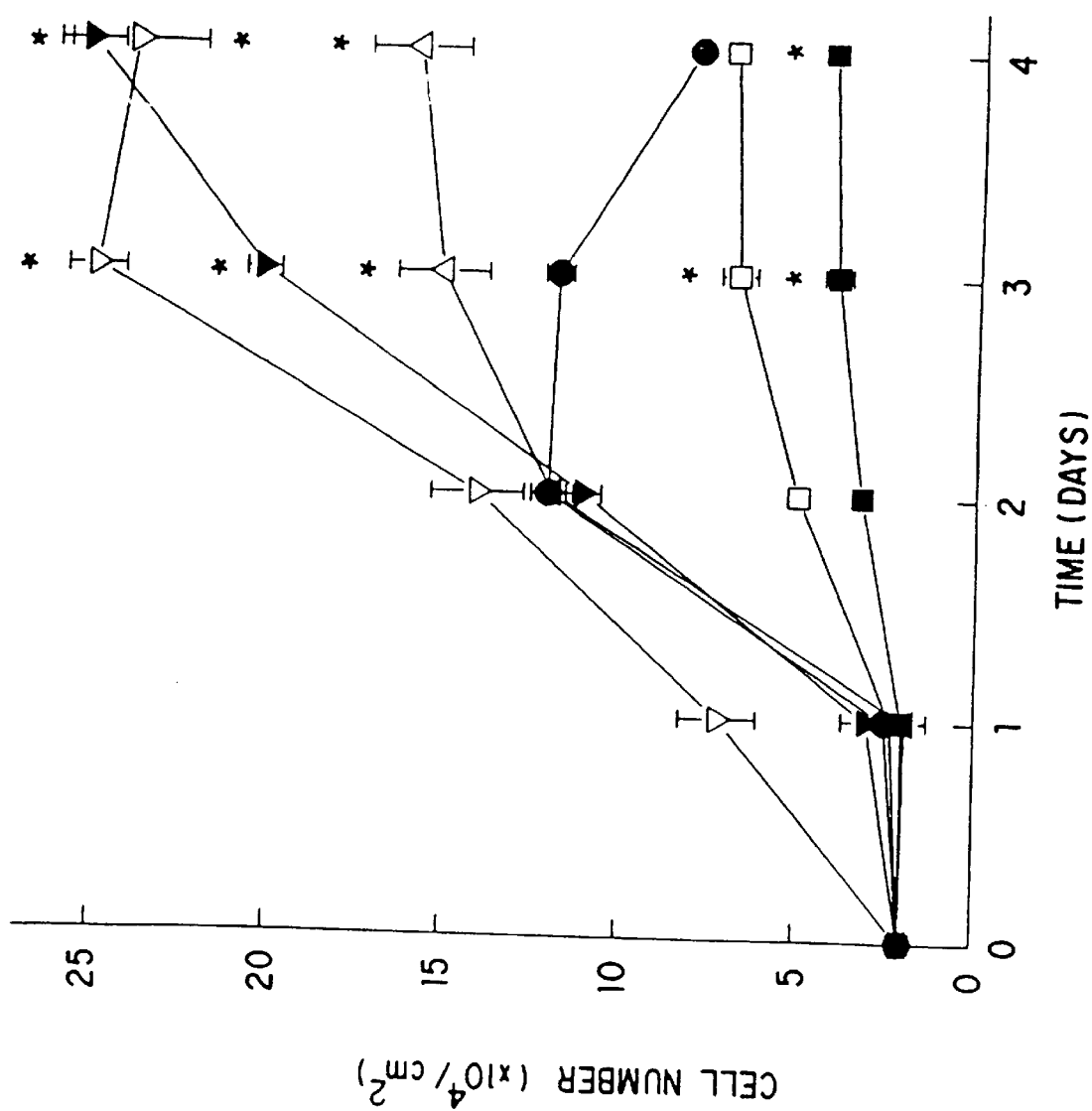

FIG. 7 illustrates a chart showing the effects of transfection with Trx or C32S/C35S cDNA on the growth of NIH 3T3 cells. Cells were plated in plastic dishes at a density of $2 \times 10^4$ $cells/cm^2$—in DMEM with 10% FBS and cell number measured daily. ●,NeoC vector alone-transfected cells. The apparent decrease in the number of cells after day 3 is due to detachment of cells from the plastic surface: ∇, ▼, and Δ, Thio6, ThioAD, and Thio9 cells transfected with Trx cDNA; □ and ■, NIHBH and NIHBF cells transfected with C32S/C35S cDNA. Values are the mean of three determinations: bars, SE. *, P<0.05 compared with vector alone-transfected cells, shown for days 3 and 4 only. The study is typical of three repeat experiments.

Figure 8:
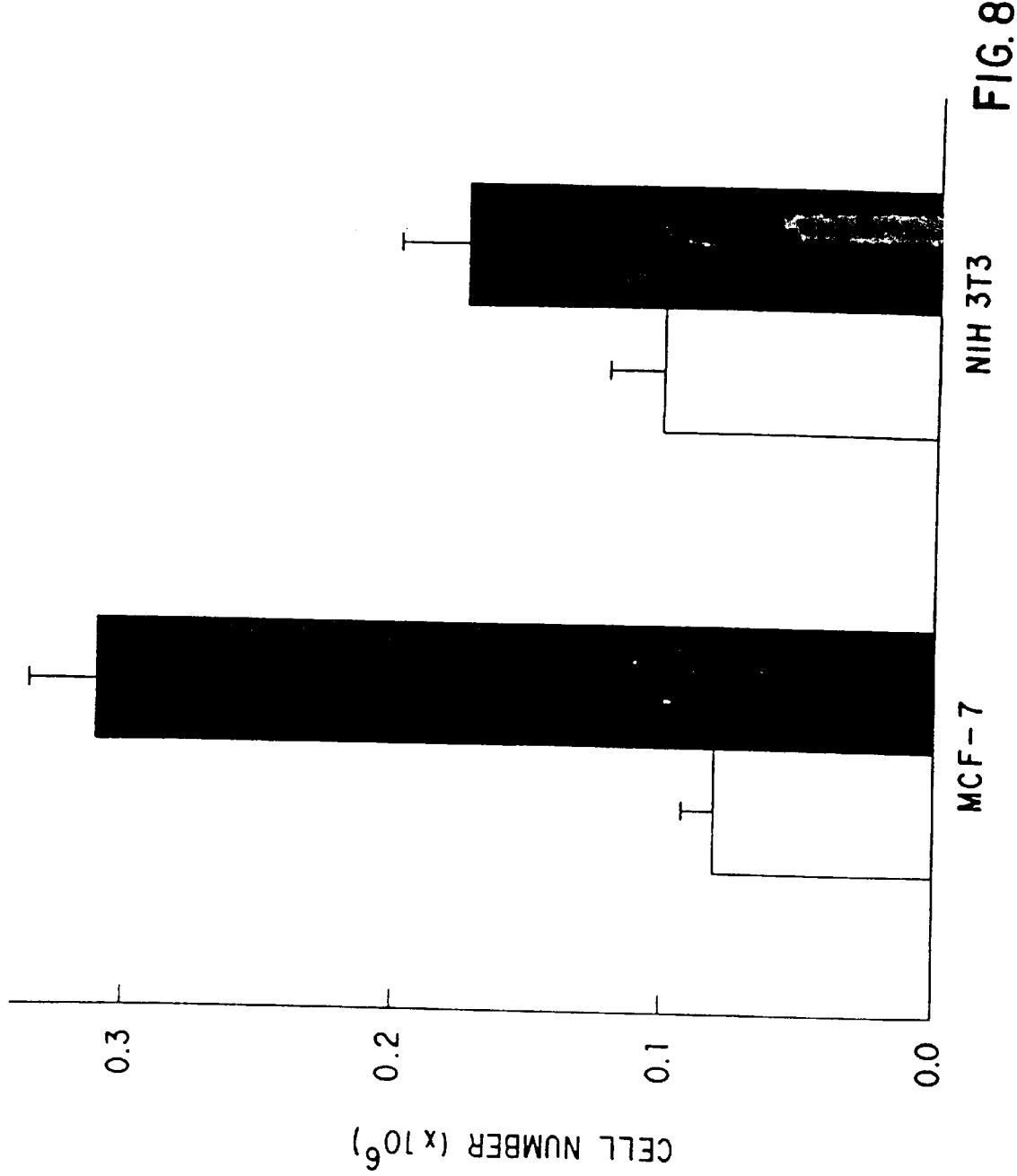

FIG. 8 illustrates a chart showing the stimulation of the proliferation of MCF-7 human breast cancer cells and mouse NIH 3T3 cells by human Trx. Cells were growth arrested in DMEM containing 0.5% FBS for 48 h so that there were $0.4 \times 10^5$ cells, at which time the medium was replaced with fresh DMEM with (■) or without (□) 1 μM human Trx. Cell numbers were measured 48 h later. Values are the mean of three determinations: bars, SE.

Figure 9A:
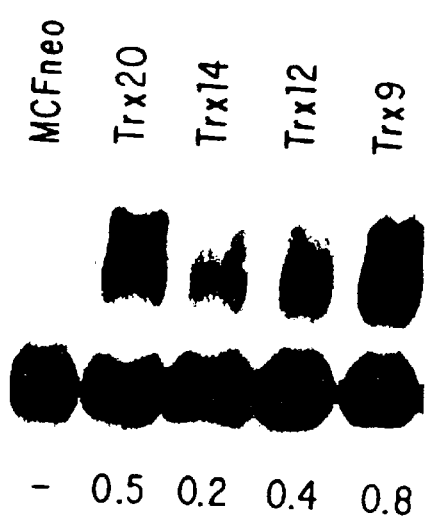
Figure 9B:
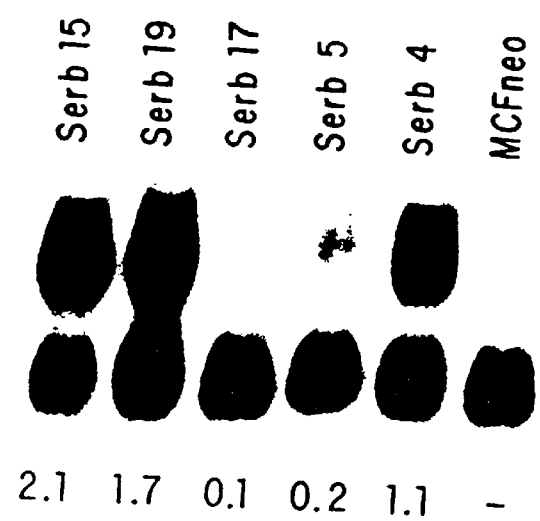

FIGS. 9A–B illustrate comparative autoradiograms showing Northern analysis of MCF-7 breast cancer cells stably transfected with cDNA for wild-type Trx (FIG. 9A) and redox-inactive mutant Trx (C32S/C35S) hybridized with a full-length $^{32}$P-labeled human Trx cDNA (FIG. 9B). MCF-neo are cells transfected with pDC304 vector alone. The blots illustrate columns of MCFneo, Trx20, Trx 14, Trx 12, and Trx9 in FIG. 9A and Serb 15, Serb 19, Serb 17, Serb 5, Serb 4 and MCFneo in FIG. 9B. The bottom band is endogenous Trx mRNA, and the top band is the transfected Trx mRNAs. Values below each column are the ratios of transfected Trx mRNA to endogenous Trx mRNA determined by phosphorimager analysis.

Figure 10A:
Figure 10B:
Figure 10C:
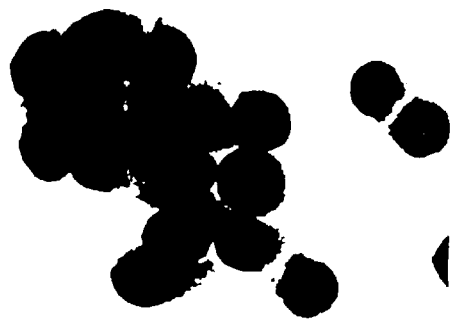
Figure 10D:

FIGS. 10A–D illustrate light microscopy of Trx and C32S/C35S cDNA-transfected MCF-7 breast cancer cells. The cells were grown to 75% confluence on glass coverslips, fixed with methanol, stained with a Romanowski-type dye (Diff-Quick, Baxter), and observed with a ×100 oil immersion objective. In FIG. 10A, pDC304 vector alone-transfected MCF-7 cells; FIG. 10B, Trx 20 Trx-transfected MCF-7 cells; FIG. 10C, Serb 4 C32S/C35S-transfected MCF-7 cells; and FIG. 10D, Serb 19 C32S/C35S-transfected MCF-7 cells.

Figure 11A:
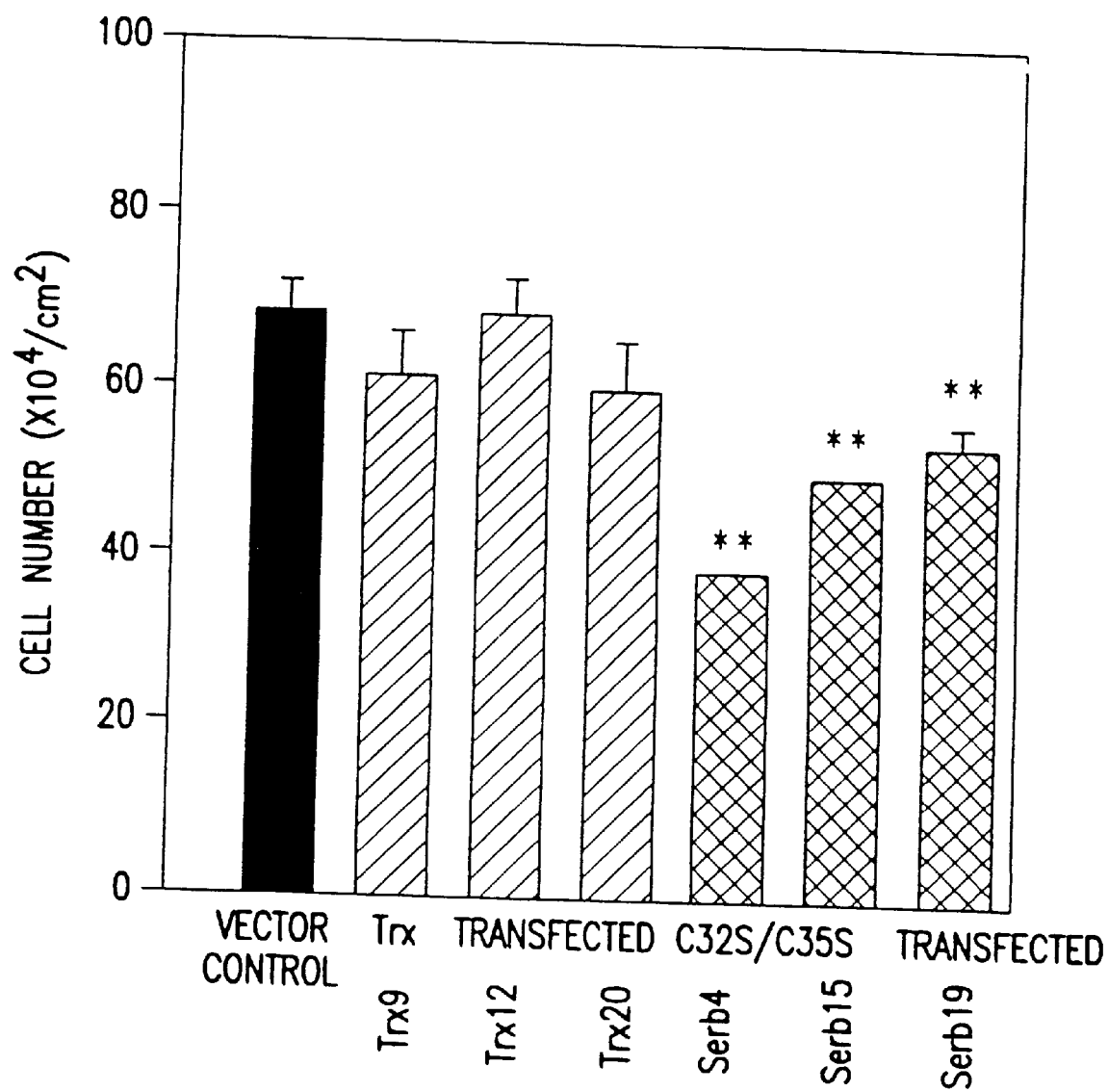
Figure 11B:
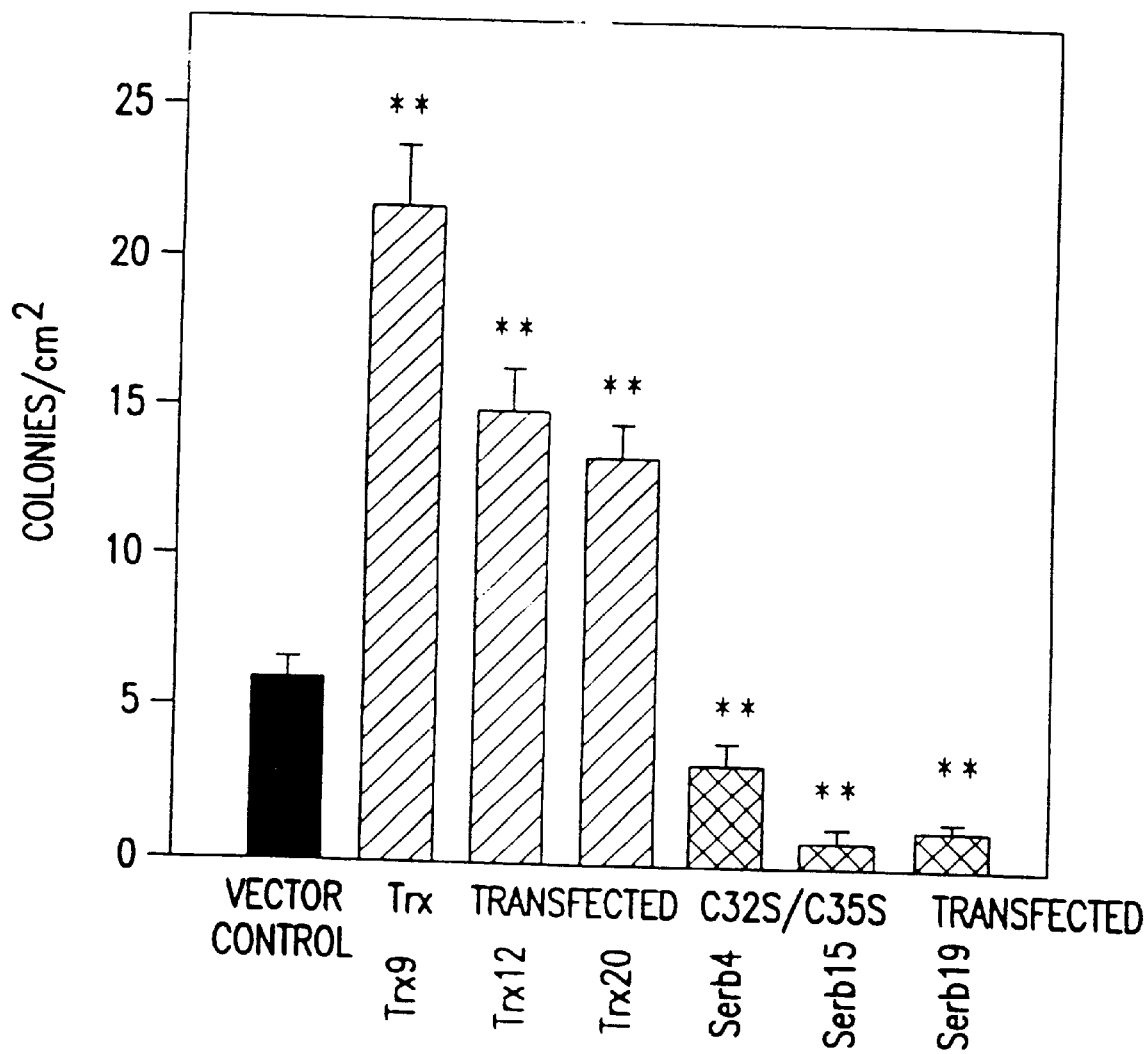

FIGS. 11A–B illustrate comparative charts showing the effects of Trx and C32S/C35S cDNA transfection on proliferation of MCF-7 cells. In FIG. 11A, cells ($3\times10^4$) were plated in 3.8-cm$^2$—plastic culture dishes in DMEM with 10% FBS, and cell number was measured 7 days later. In FIG. 11B, cells ($10^4$) were plated in 2-cm$^2$—wells containing soft agarose, and colonies measuring >60 $\mu$m were counted 7 days later. In both FIGS. 11A and B, the chart shows control Neol vector alone-transfected MCF-7 cells, Trx 9, Trx 12, and Trx 20, MCF-7 cells transfected with human Trx cDNA: Serb 4, Serb 15, and Serb 19, MCF-7 cells transfected with C32/C35S cDNA. Values are the mean of three determinations: bars, SE, **, P<0.01 compared with vector alone-transfected cells.

Figure 12:
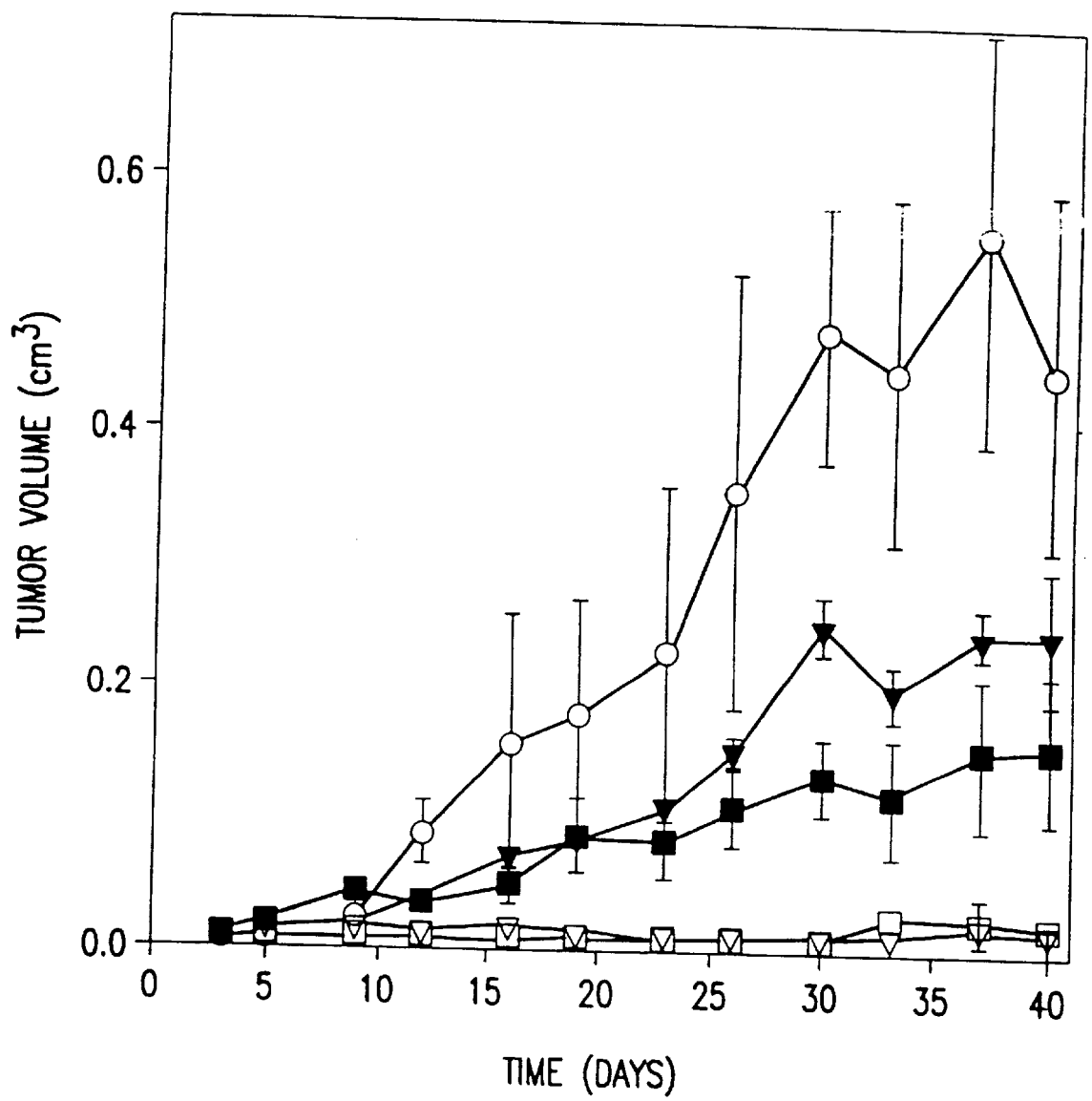

FIG. 12 illustrates a chart showing the growth of Trx and C32S/C35S-transfected MCF-7 breast cancer cells is Scid mice. Female Scid mice implanted s.c. 2 days previously with a 21-day release pellet of 0.25 mg of 17-β-estradiol were injected s.c. with $2\times10^6$ transfected MCF-7 cells in 0.1 ml of 0.9% NaCI and 0.1 ml of Matrigel. ○, MCFneo, pDC304 vector alone-transfected MCF-7 cells: ▼, Trx 12, Trx-transfected cells; ■. Trx 20, thioredoxin-transfected cells: ▼. Serb 4. C32S/C35S-transfected cells; □, Serb 15, C32S/C35S-transfected cells. There were four mice per group. Tumor growth was measured twice a week for 40 days. The 17-β-estradiol pellet was replaced at 21 days. Values are mean. Bars, SE.

Figure 13:
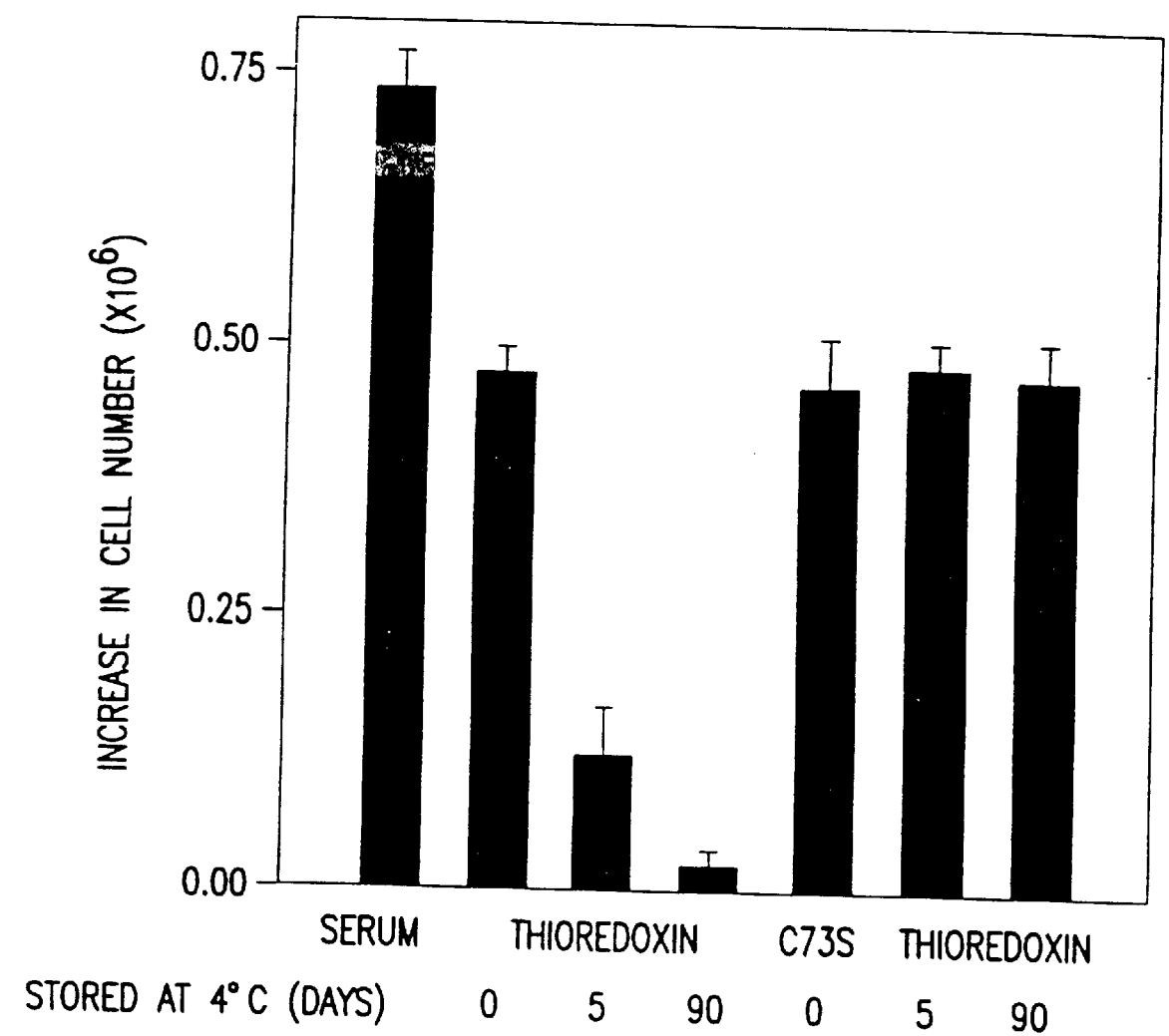

FIG. 13 illustrates a chart showing the stimulation of MCF-7 breast cancer cell growth by fresh and aged Trx and C73S. MCF-7 cells were growth arrested and the stimulation of cell proliferation measured over 2 days using 1 $\mu$M Trx or C73S that was fresh or had been stored as a 25, $\mu$M stock solution without reducing agent for 5 days or 90 days at 4°. Also shown for reference is the effect of 10% fetal bovine serum. Each value is the mean of 3 determinations, and bars are SEM.

Figure 14:
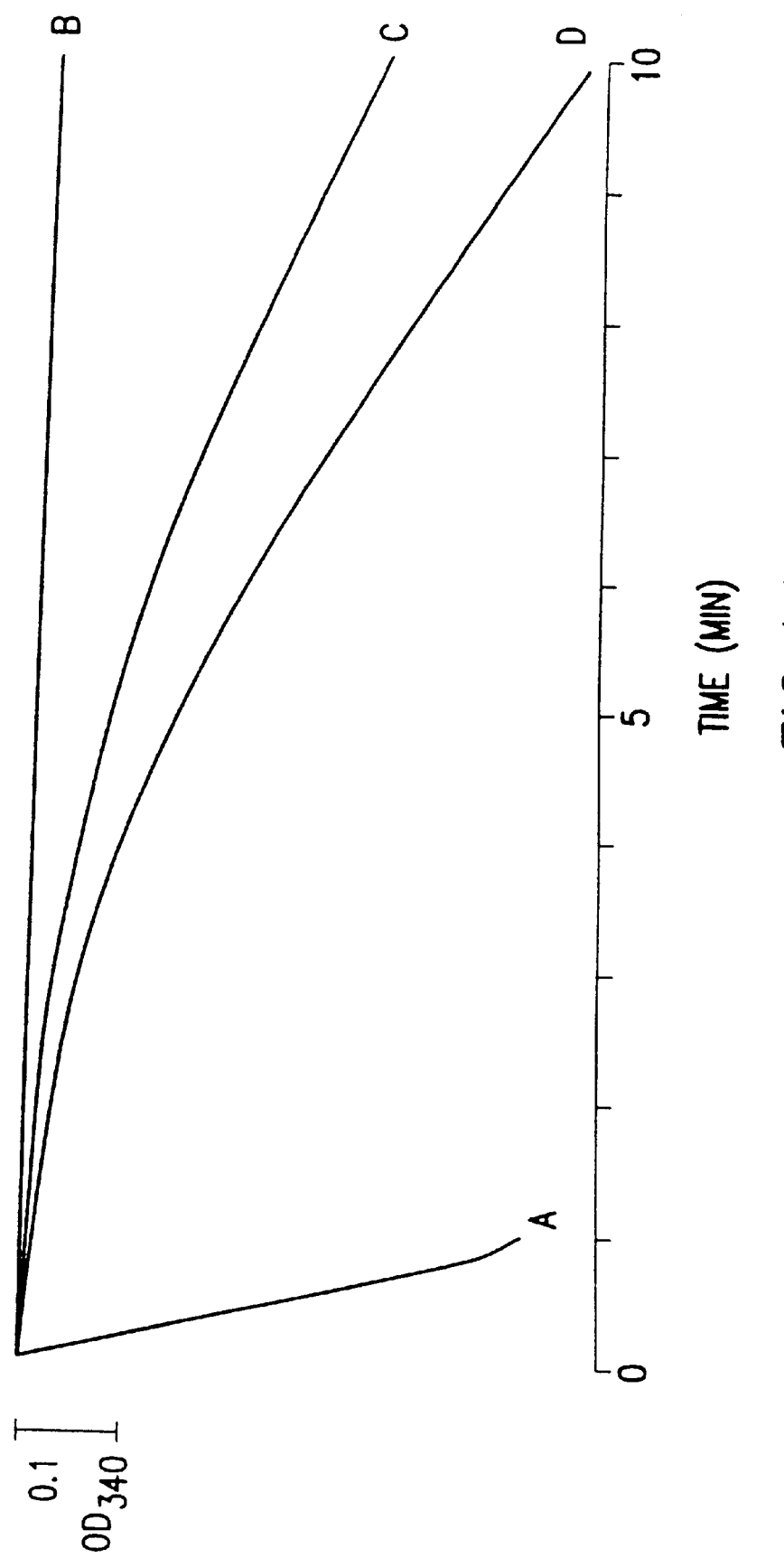

FIG. 14 illustrates a chart showing the reduction of aged Trx by thioredoxin reductase. The incubation mixture contained 0.1 M HEPES buffer, pH 7.6, 5 mM EDTA, 17 $\mu$M insulin, 100 $\mu$M NADPH, 15 $\mu$g/ml human thioredoxin reductase. Traces show the oxidation of NADPH at 340 nm at room temperature with: Line A represents 1 $\mu$M fresh Trx; Line B represents 30 nM fresh Trx; Line C represents 90-day aged 1 $\mu$M Trx; and Line D represents 1 $\mu$M 90-day aged Trx and 30 nM fresh Trx.

Figure 15:
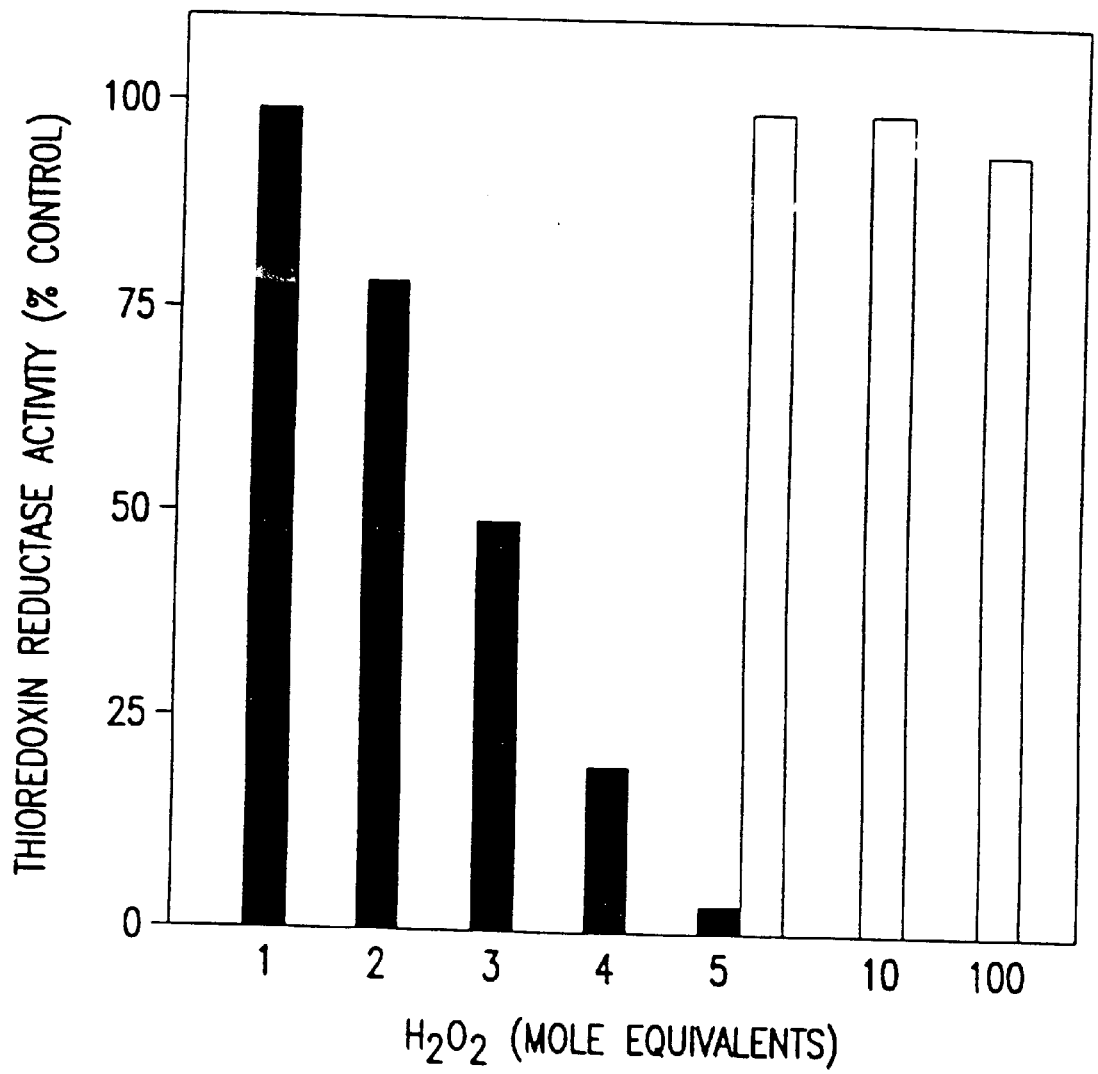

FIG. 15 illustrates a chart showing the effect of $H_2O_2$ on the reduction of Trx (filled bars) and C73S (open bars) by thioredoxin reductase. Trx solutions were treated with varying amounts of $H_2O_2$ for 18 hr. at room temperature. Reductase activity was measured by adding treated samples to a solution of 0.1 M HEPES buffer, pH 7.6, 5 mM EDTA, 17 $\mu$M insulin, 100 $\mu$M NADPH, 15 $\mu$g/ml human thioredoxin reductase and measuring the rate of NADPH oxidation at 340 nm at room temperature. One hundred percent of thioredoxin reductase activity is defined as 0.1 absorbance unit/min/mM Trx or C73S Trx $H_2O_2$ had no effect on the oxidation of NADPH.

Figure 16:
Figure 16:
Figure 16:

FIG. 16 illustrates an electrophoretic analysis showing the effect of storage on Trx studied by SDS-PAGE. Protein was stained with silver stain. Lane 1 represents fresh Trx; lane 2 represents Trx 48 hr. at room temperature without DTT; lane 3 represents Trx 7 days at room temperature without DTT; and lane 4 represents Trx stored 90 days at 4° without DTT. Position of molecular mass markers in kDa are shown on the left.

Figure 17:
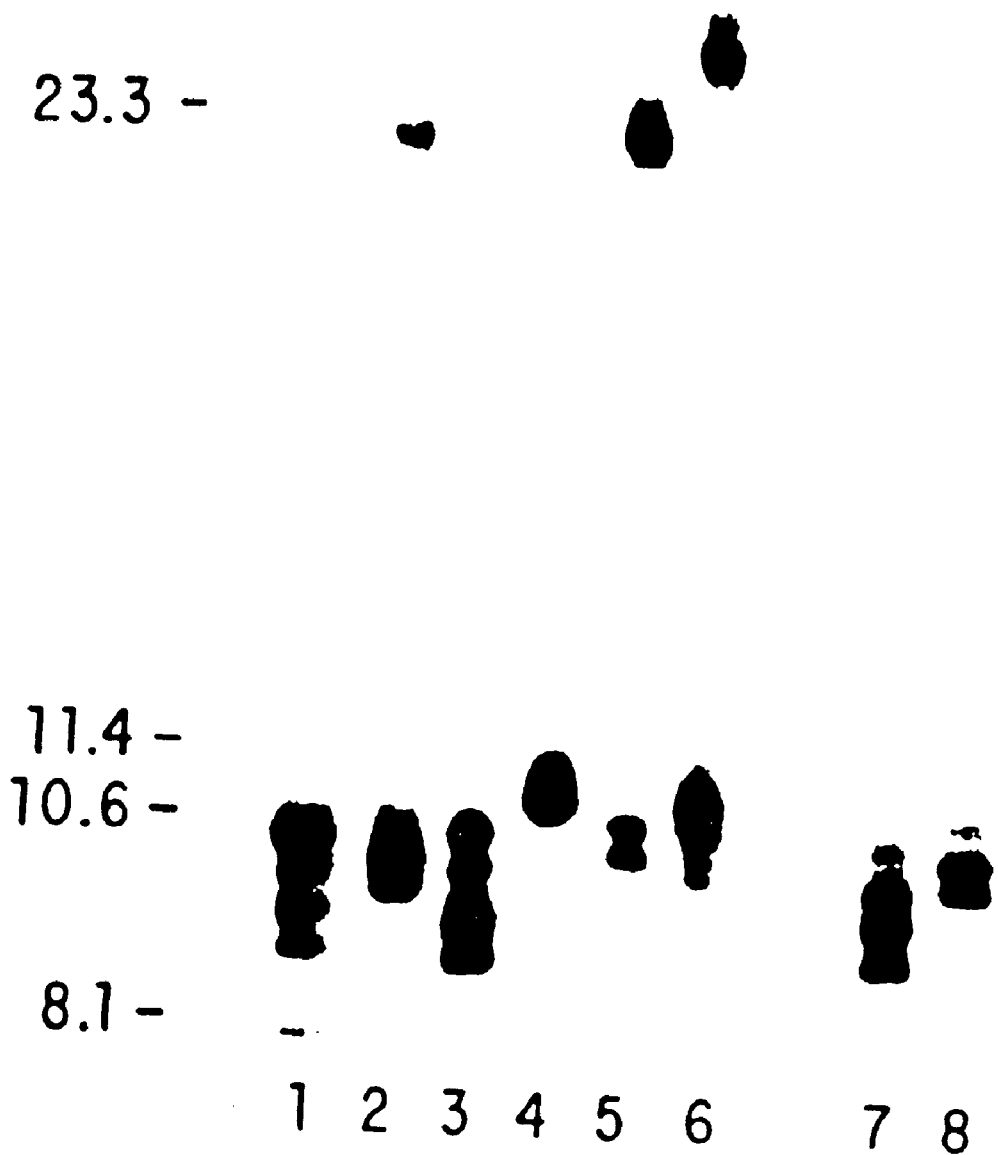

FIG. 17 illustrates an electrophoretic analysis showing the oxidation and alkylation of Trx studied by SDS-PAGE. Lane 1 represents fresh Trx; lane 2 represents Trx stored at room temperature without DTT for 7 days; lane 3 represents Trx as in lane 2 treated with 3 mM 2-mercaptoehtanol; lane 4 represents fresh Trx treated with 1 mM N-ethylmaleimide; lane 5 represents fresh Trx treated with 1 mM diamide; lane 6 represents fresh Trx treated with 2:1 (v:v) $H_2O_2$; lane 7 represents Trx as in lane 5 treated with 3 mM 2-mercaptoethanol; and lane 8 represents Trx as in lane 6 treated with 10 mM 2-mercaptoethanol. Position of molecular mass markers in kDa are shown on the left.

Figure 18:

FIG. 18 illustrates an electrophoretic analysis showing the oxidation and reduction of mutant Trxs studied by SDS-PAGE. Lane 1 represents fresh Trx; lane 2 represents fresh C73S Trx; lane 3 represents fresh C32S/C35S Trx; lane 4 represents C73S Trx treated with 1 mM diamide; lane 5 represents C73S Trx as in lane 4 treated with 10 mM DTT; lane 6 represents C32S/C35S Trx treated with 1 mM diamide; and lane 7 represents C32S/C35S Trx as in lane 6 treated with 10 mM DTT. Position of molecular mass markers in kDa are shown on the left and right.

Figure 19:
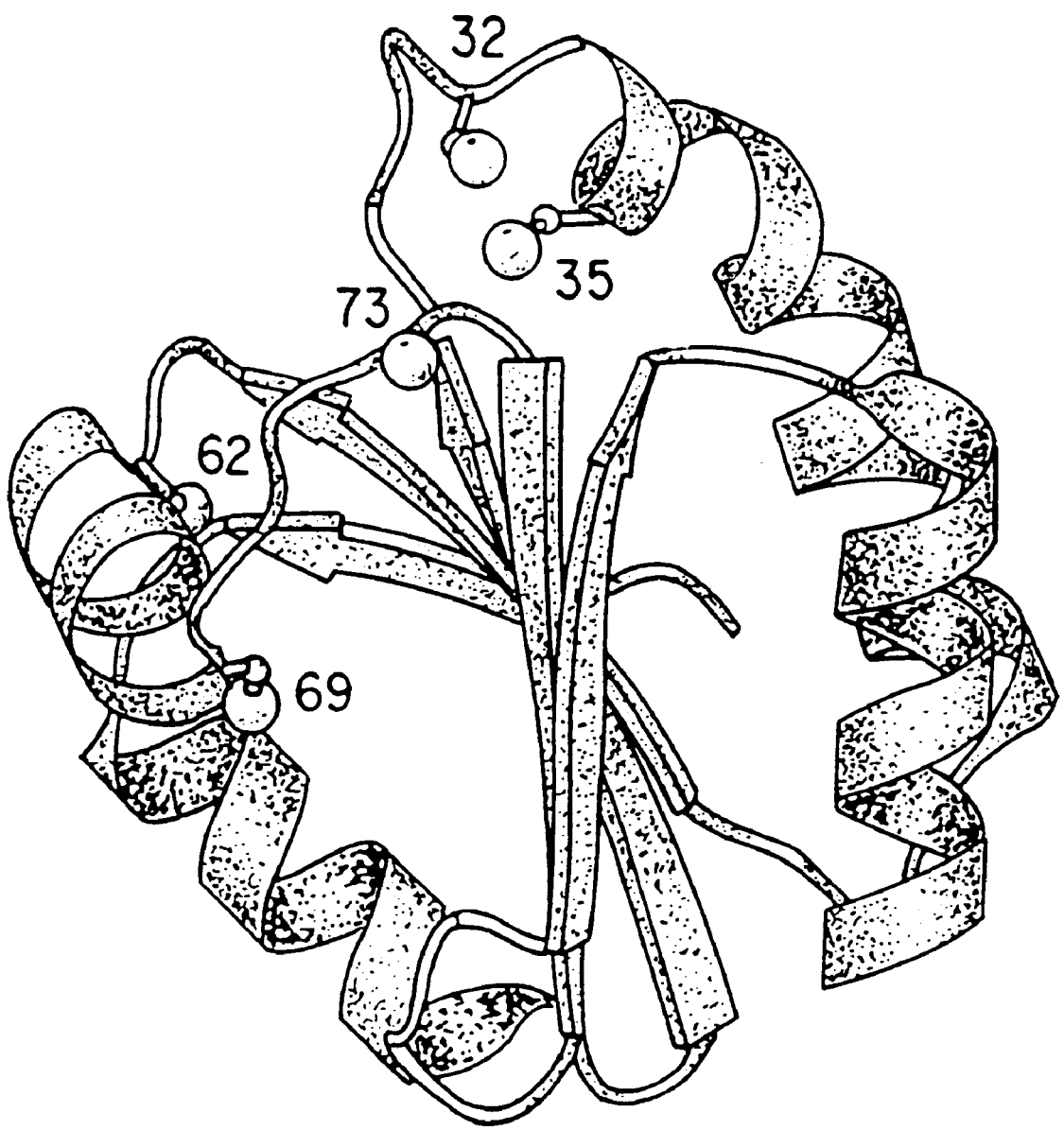

FIG. 19 illustrates the position of cysteines in human Trx. Ribbons and ball-and-stick representation showing the relative positions of $Cys^{32}$, $Cys^{35}$, $Cys^{62}$, $Cys^{69}$ and $Cys^{73}$, based on the crystal coordinates for the wild type reduced protein (Weichsel A. et al., Structure 4:735–751, 1996). None of the thiols are in a position for disulfide bond formation except for the redox active pair $Cys^{32}$ and $Cys^{35}$. The intermolecular disulfide bond requiring the least distortion in the protein would be between $Cys^{32}$ and $Cys^{73}$. The sulfhydryls for these residues are 9.1 Å apart in the model, but could possibly approach each other through local distortions in nearby residues. Both residues are in loops, making necessary distortions of energetically lower cost. The region near $Cys^{32}$ has already been shown to adopt alternate conformations (Weichsel. A. et al., Structure 4:735–751, 1996), in support of this possibility. This figure was made with MOLSCRIPT (Sato N. et al., J. Immunol., 154:3194–3203, 1995).

Figure 20A:
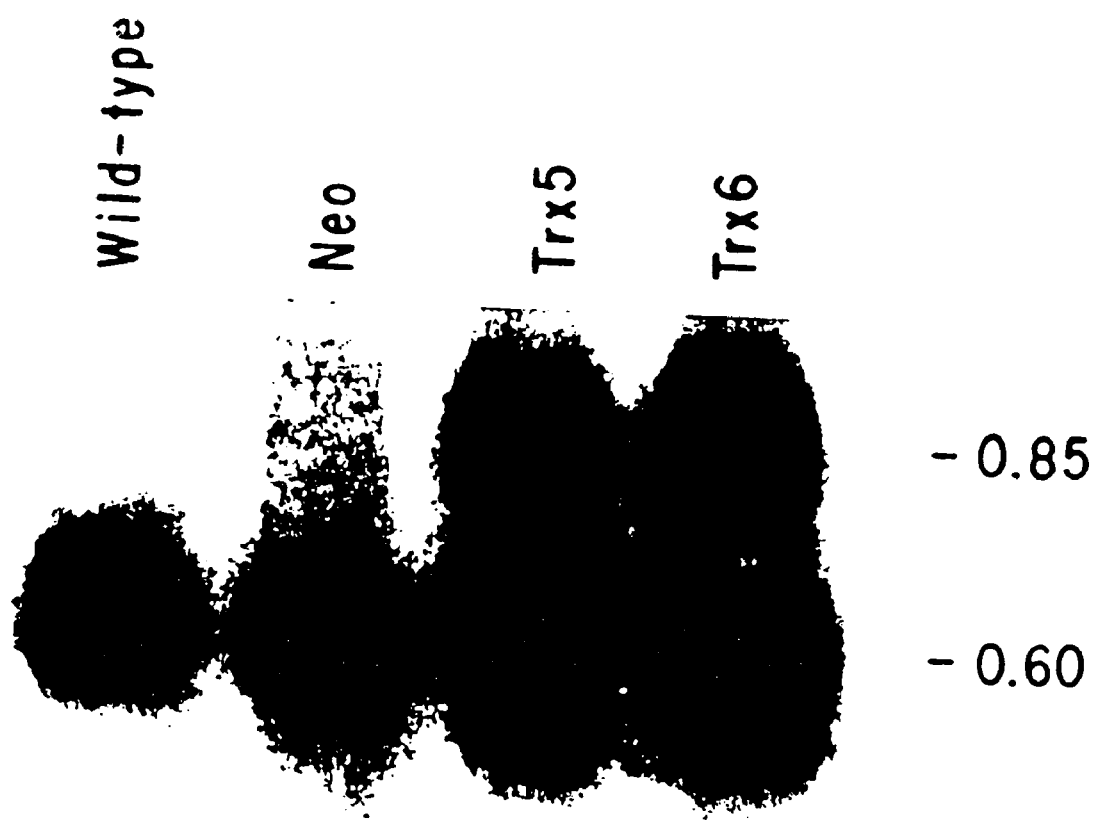

FIG. 20A shows a Northern blot hybridization analysis of total RNA extracted from: wild-type mouse WEHl7.2 cells; from pDC304neo vector-alone transfected WEHl7.2 cells (Neo); and from the trx-transfected WEHl7.2 clones Trx5 and Trx6. A full-length $^{32}$P-labeled trx cDNA probe was used for hybridization. Top band, transfected human Trx mRNA; bottom band, mouse Trx mRNA. The values on the right show the position of molecular weight markers (kb).

FIGS. 20B(1)–(4) illustrate fluorescence immunohistochemical staining of Trx in cells using immunoaffinity-purified rabbit antihuman Trx polyclonal antibody, biotinylated goat antirabbit IgG fluorescein streptavidin, and laser scanning confocal microscopy. FIG. 20B(1) represents wild-type WEHl7.2 cells; FIG. 20B(2) represents pDC304neo vector-alone transfected WEHl7.2 cells; FIG. 20B(3) represents Trx5 trx-transfected cells; and FIG. 20B(4) represents Trx6 trx-transfected cells.

FIGS. 20C(1)–(2) illustrate a fluorescence immunohistochemical staining of Trx using Cy5-streptavidin fluorochrome and YOYO-1 to counterstain nuclear DNA showing that Trx is present in the cytoplasm and the nucleus of wild-type WEHl7.2 cells (in FIG. 20C(1)) and Trx6 trx-transfected cells (in FIG. 20C(2)).

FIG. 21 shows comparative charts illustrating the effects of trx and bcl-2 transfection in WEHl7.2 cells on dexamethasone-induced apoptosis.

Figure 21A:
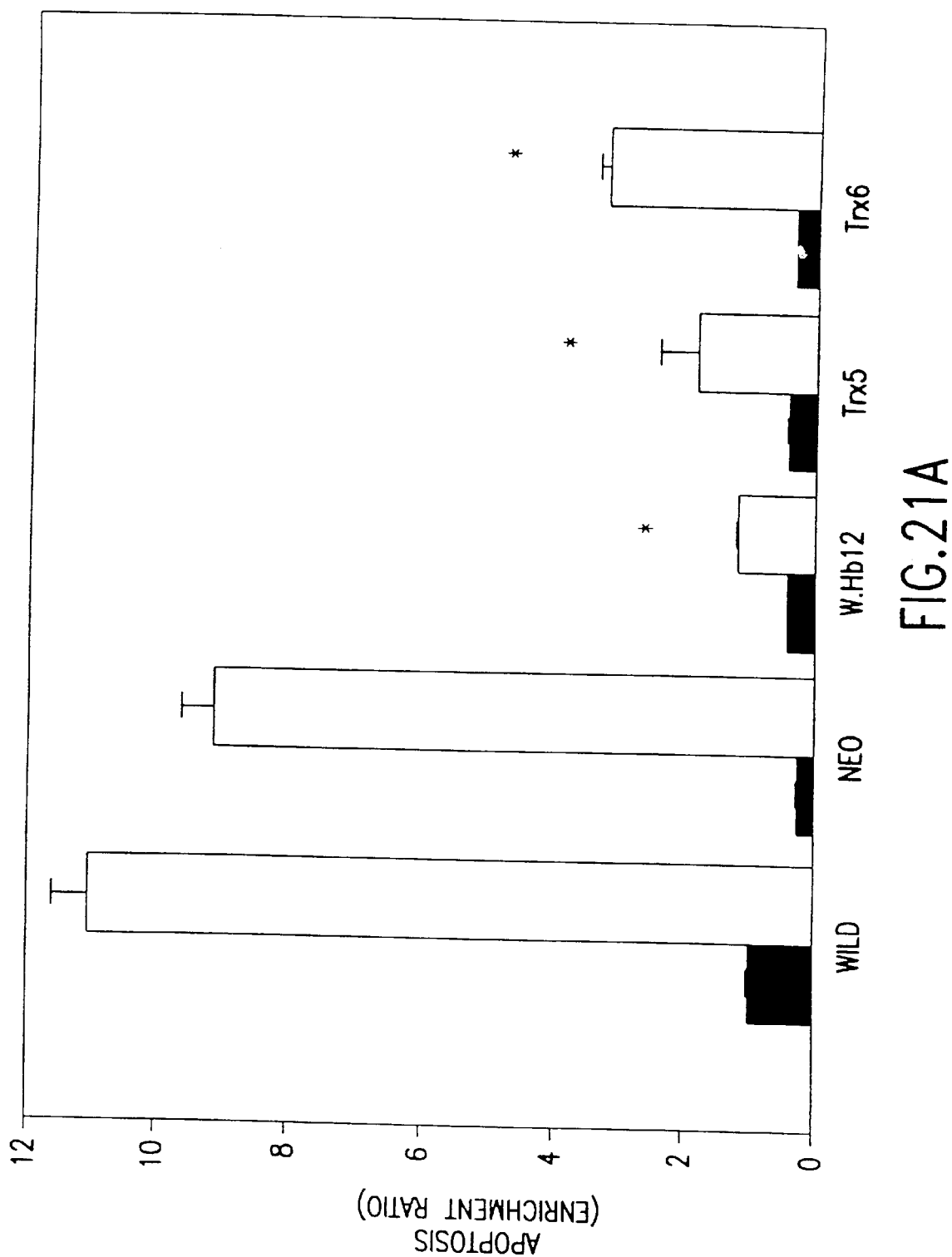

FIG. 21A shows a chart illustrating apoptosis measured by an ELISA for histone-associated DNA fragments, expressed as relative nucleosomal enrichment. Wild represents wild-type WEHl7.2 cells; Neo represents pDC304neo vector-alone-transfected WEHl7.2; W.Hbl2 represents bcl-2-transfected WEHl7.2; and Trx5 and Trx6 represent trx-transfected WEHl7.2 cells. The cells were treated with 0.01% ethanol vehicle (■) or I μM dexamethasone (□), and apoptosis was measured 24 h later. Columns, mean of four determinations; bars, SE. *, P<0.05 compared to Neo control.

FIGS. 21B(1)–(4) illustrate comparative charts of apoptosis measured by flow cytometry showing typical results. Regions R1, R2, and R3 of the scattergrams represent live nonapoptotic, early apoptic, and late apoptotic cells, respectively. FIG. 21B(1) shows pDC304neo vector-alone-transfected control cells; FIG. 21B(2) shows pDC304neo vector-alone-transfected cells treated for 48 h with 1 μM dexamethasone; FIG. 21B(3) shows Trx6 trx-transfected WEH 17.2 cells; and FIG. 21B(4) shows Trx6 cells treated for 48 hr. with 1 μM dexamethasone.

Figure 22A:
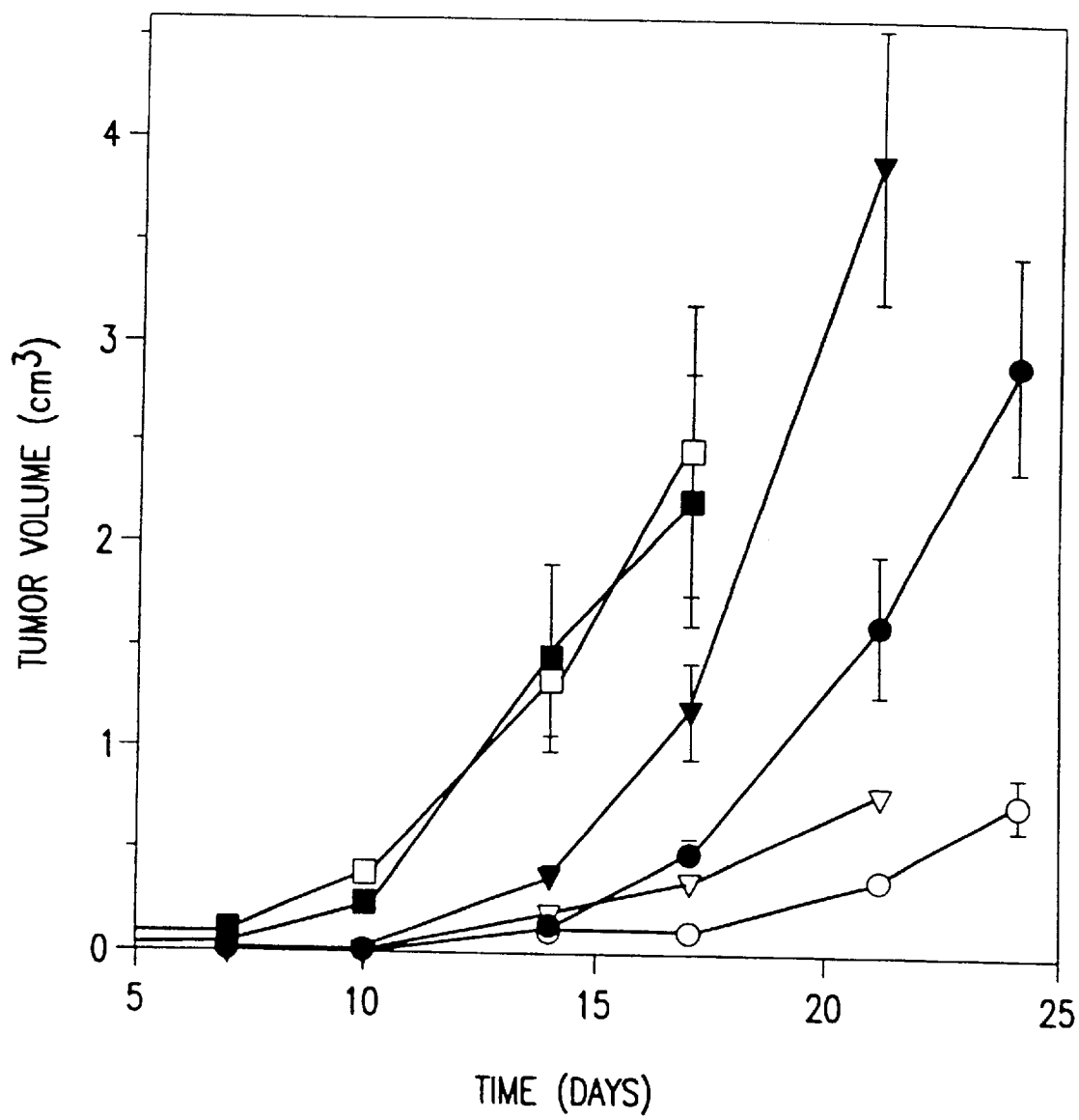
Figure 23A:
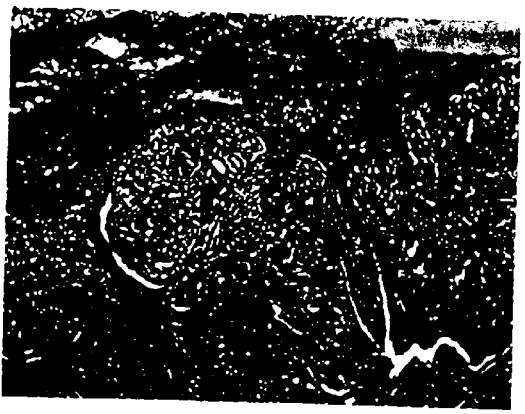
Figure 23C:
Figure 23B:
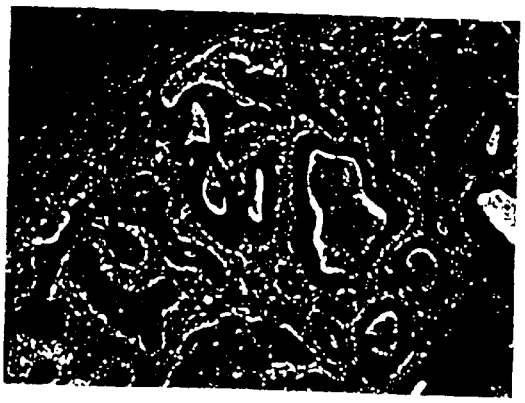
Figure 23D:
Figure 25A:
Figure 25B:
Figure 25C:
Figure 25D:
Figure 26A:
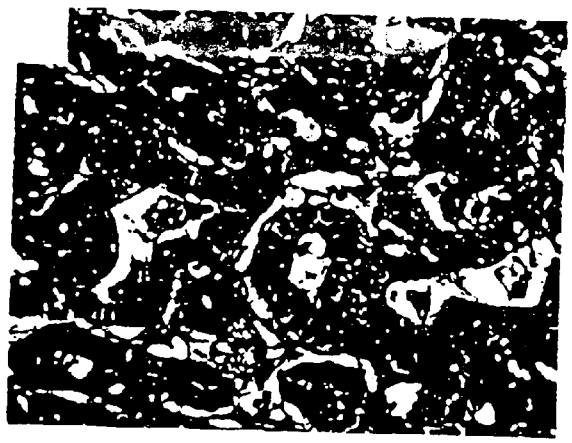
Figure 26B:
Figure 26C:
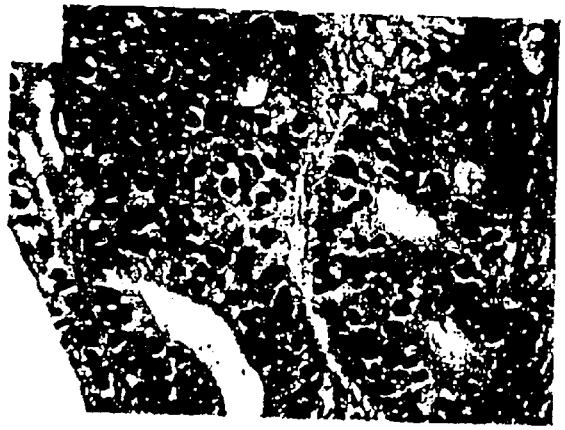
Figure 26D:
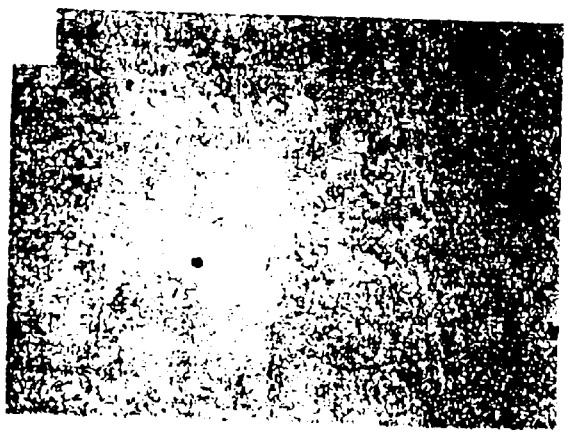
Figure 27A:
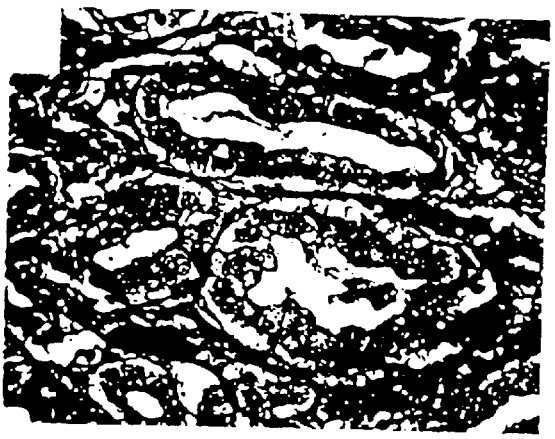
Figure 27B:
Figure 27C:
Figure 27D:
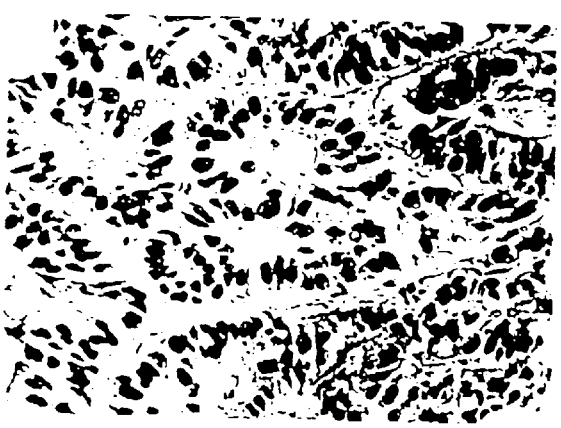

FIG. 22A shows a chart illustrating tumor formation in Scid mice by wild-type WEHl7.2 cells (o and ●); bcl-2-transfected WEHl7.2 (W. Hbl2) cells (∇ and ▼); and Trx6 trx-transfected WEHl7.2 cells (□ and ■). Twenty mice were injected s.c. with 2×10$^7$ cells and 0.1 ml matrigel in the flank. Tumor size was measured every 3–4 days with calipers, and tumor volumes were calculated. Nine days after tumor cell injection, half of the mice were injected s.c. into the opposite flank with 1 mg/kg/day dexamethasone (o, ∇, and □) or with vehicle alone (●, ▼, and ■). Mice were euthanized at the first measurement at which tumor volume exceeded 2 cm$^3$. Data points, mean of 10 mice in each group; bars, SE. Results similar to the Trx6 cells were obtained with Trx5 cells.

FIG. 22B illustrates 1-μm sections of epoxy-embedded tumor samples taken at day 14 stained with toluidine blue o examined by bright-field microscopy. Spontaneous apoptosis in wild-type WEHl7.2 tumor are shown in FIG. 22B(1) and Trx6 tumor showing less spontaneous apoptosis are shown in FIG. 22B(2).

FIG. 23 illustrates thioredoxin positive gastric carcinoma (Case 2). FIGS. 23A–B show that hematoxylin and eosin stains (FIG. 23A and FIG. 23B) reveal a pleomorphic carcinoma invading the gastric wall. FIGS. 23C–D show that the thioredoxin expression (FIG. 23C and FIG. 23D) is present in both the nuclei and cytoplasm of tumor cells in malignant glands and in rare associated leucocytes. Thioredoxin expression is absent in the adjacent stroma (100× to 400×).

FIG. 24 illustrates thioredoxin negative gastric carcinoma (Case 8). FIG. 24A represents gastric carcinoma with complex glands in lower field of view with overlying normal gastric mucosa and submucosa. Hematoxylin and eosin (100×). FIG. 24B represents the same section as shown in FIG. 24A, negative control stained after biotin-avidin block to eliminate biotin receptor affect and stained with substituted irrelevant isotype matched monoclonal antibody (100×, Diaminobenzidine). FIG. 24C represents the same section as shown in FIGS. 24A and B showing faint reactivity in normal upper mucosa (+), moderate reactivity in the submucosa (++) and the underlying gastric carcinoma appears negative for thioredoxin (0) (100×). FIG. 24D represents a higher magnification of FIG. 24C showing detail with gastric pit cells having both nuclear and cytoplasmic stain and absent tumor staining (250×).

FIG. 25 illustrates normal gastric mucosa—thioredoxin and Ki67 (proliferation antigen) expression. FIG. 25A shows normal gastric mucosa and gastric pits with underlying muscularis propria hematoxylin and eosin (100×). FIG. 25B shows the same section as shown in FIG. 25A, stained for thioredoxin with faint (+) mucosal staining and moderate (++) gastric pit staining (100×). FIG. 25C shows the same section as shown in FIG. 25B at higher magnification. Note the faint mucosal staining is solely cytoplasmic, while lower lying gastric pit cells are both cytoplasmic and nuclear (250×). FIG. 25D shows the nuclear Ki67 expression notable in lower mucosa and upper gastric pits (250×).

FIG. 26 illustrates thioredoxin intense gastric carcinoma related to strong proliferation and weak apoptosis (Case 4). FIG. 26A shows complex adenocarcinoma cell glands (400×, hematoxylin and eosin). FIG. 26B shows intense thioredoxin expression in gastric carcinoma cells (400×). FIG. 26C shows a high percentage of Ki67 positive cells indicating high proliferation (400×). FIG. 26D shows a rare Tdt+− apoptotic cell 25 indicating weak apoptosis (Tunel assay, 400×, same slide).

FIG. 27 illustrates thioredoxin negative gastric carcinoma related to weak proliferation and strong apoptosis (Case 6). FIG. 27A shows complex adenocarcinoma glands (400×, hematoxylin and eosin). FIG. 27B shows the absent thioredoxin expression (400×). FIG. 27C shows a low percentage of Ki67 positive cells indicating a low proliferative rate (400×). FIG. 27D shows a very high Tdt+ apoptotic cell rate indicating strong apoptosis (TUNEL assay, 400×, same slide).

4. DETAILED DESCRIPTION OF THE INVENTION

All of the various publications cited in the present specification are incorporated by reference in their entireties.

4.1 DEFINITIONS

In order that the invention herein described may be fully understood, the following definitions are provided:

"Nucleotide" means a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a "nucleoside". The base characterizes the nucleotide. The four DNA bases are adenine ("A"), guanine ("G"), cytosine ("C"), and thymine ("T"). In RNA uracil ("U") substitutes for T. In double stranded molecules, an A on one strand pairs with T(U) on the other, and G with C. As is conventional for convenience in the structural representation of a DNA nucleotide sequence only one strand is shown in which A on one strand connotes T on its complement and G connotes C. DNA comprises deoxyribose as the sugar while RNA comprises ribose.

"Amino acids" are shown either by a three letter or one letter abbreviation as follows:

| Abbreviated Designations | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

"DNA Sequence" means a linear array of nucleotides connected one to the other by phosphodiester bonds between the 3' and 5' carbons of adjacent pentoses.

"Codon" means a DNA sequence of three nucleotides (a triplet) which encodes through mRNA an amino acid, a translation start signal or a translation termination signal. The code however, is degenerate, with some amino acids being encoded by more than one triplet codon. For example, the nucleotide triplets TTA, TTG, CTT, CTC, CTA and CTG all encode the amino acid leucine ("Leu"), TAG, TAA and TGA are translation stop signals and ATG is a translation start signal.

"Proteins", "peptides" and "poly peptides" are composed of a linear array of amino acids connected one to the other by peptide bonds between the alpha-amino and carboxyl groups of adjacent amino acids.

"Genome" means the entire DNA of an organism, cell or a virus. It includes, inter alia, the structural genes coding for polypeptides, as well as regulatory regions including operator, promoter, terminator, enhancer and ribosome binding and interaction sequences.

"Gene" means a DNA sequence which encodes through its template or messenger RNA ("mRNA") a sequence of amino acids characteristic of a specific polypeptide.

"cDNA" means a complementary or copy DNA prepared by using mRNA as a template for synthesizing the first strand of DNA using reverse transcriptase, an appropriate oligonucleotide primer and a mixture of nucleotides.

"PCR" means a polymerase chain reaction whereby a specific DNA sequence, either genomic or cDNA, can be preferentially amplified by the enzyme Taq polymerase using synthetic, oligonucleotide sense and antisense primers, (which specify a target sequence), a mixture of nucleotides and a temperature thermocycling regime which allows sequential denaturing, annealing and synthesis of the target DNA between the primers.

"Transcription" means the process of producing mRNA from a gene or DNA sequence.

"Translation" means the process of producing a polypeptide from mRNA.

"Expression" means the process undergone by a gene or DNA sequence to produce a polypeptide and comprises a combination of transcription and translation.

"Plasmid" or "phagemid" means a nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for ampicillin resistance ($AMP^R$) transforms a cell previously sensitive to ampicillin into one which is resistant to it. A cell transformed by a plasmid is called a "transformant".

"Recombinant DNA Molecule" or "Hybrid DNA" means a molecule consisting of segments of DNA from different genomes which have been joined end-to-end outside of living cells and able to be maintained in living cells.

"Apoptosis" is programmed cell death activated by a genetic program to implement a series of events that cause the death and disposal of a cell. This is in contrast to cell death occurring by necrosis, usually as a result of injury to the cell.

"Oncogene" is a gene that encodes a protein able to transform cells in culture to induce cancer in animals.

"Over-expression" in the context of determining over-expression of thioredoxin or recombinant modified thioredoxin is characterized by a two fold increase or more of the levels of thioredoxin or recombinant modified thioredoxin in a target sample compared with a control sample.

The following abbreviations may be used throughout the disclosure:

"C32/C35S"=$Cys^{32} \rightarrow Ser^{32}/Cys^{35} \rightarrow Ser^{35}$

"DTT"=dithiothreitol

"FBS"=Fetal bovine serum

"NEM"=N-ethylmaleimide

"Scid"=Severe combined immunodeficient

"Trx"=thioredoxin 4.2 Use of Thioredoxin as an Oncogene

In a non-limiting embodiment of the present invention, NIH 3T3 cells transfected with human thioredoxin DNA that has been directed to the nucleus of the cells by a nuclear localization signal causes malignant transformation of the cells.

In a further non-limiting embodiment, stable transfection of mouse WEHI7.2 lymphoid cells with human thioredoxin DNA has been shown to inhibit apoptosis induced by a variety of agents including glucocorticoid, N-acetylsphingosine, staurosporine, thapsigargin and etoposide, which is similar to the pattern of inhibition of apoptosis caused by the anti-apoptotic oncogene bcl-2 in these cells. The thioredoxin transfected WEHI7.2 cells form tumors in Scid mice that grow more rapidly and show less spontaneous apoptosis than vector-alone or bcl-2 transfected cells, and are resistant to growth inhibition by glucocorticoid. Therefore, the thioredoxin gene acts as an oncogene according to the standard definition of an oncogene: a gene that encodes a protein able to transform cells in culture or to induce cancer in animals (Lodish H, et al., "Cancer." In: Lodish H, Baltimore D, Berk A, Zipursky S L, Matsudaira P, Darnell J, eds. *Molecular Cell Biology*. New York: Scientific American Books, pp. 1258, 1995).

In a further non-limiting embodiment, the thioredoxin gene offers an increased survival advantage as well as a growth advantage to tumors in vivo, unlike the known anti-apoptosis oncogene bcl-2 which offers only a survival advantage and requires other genetic changes for tumor growth (McDonnell T J, et al., *Nature* 349:254–256, 1991).

4.3 Thioredoxin is Over-Expressed in Certain Human Tumor Cells

It has been discovered that thioredoxin DNA is over-expressed in certain human tumor cells resulting in the over production of thioredoxin. According to a technique for reproducibly retrieving antigens for immunohistochemical studies from archived paraffin, human tissue pathology samples were embedded and used it to study thioredoxin protein levels with a panel of human primary gastric carcinoma tissue samples, it has been found that thioredoxin is present in dividing normal basal crypt cells. It has been further learned that, as the cells differentiate and move down the villi to eventually be shed into the gastric lumen, thioredoxin levels decrease. By stably transfecting murine NIH 3T3 fibroblast-like cells and human MCF-7 breast cancer cells with cDNA for human wild-type thioredoxin or with cDNA for a redox-inactive mutant thioredoxin, it has been found that transfection with thioredoxin increases the density to which the NIH 3T3 cells grow in culture and stimulates anchorage-independent colony formation by MCF-7 breast cancer cells. The redox-inactive mutant thioredoxin acted in a dominant-negative manner, so that transfected MCF-7 cells showed inhibited growth and a reversal of the transformed phenotype, assessed by growth in vitro and in vivo.

It has been shown that stable transfection of mouse NIH 3T3 normal embryonic cells with human thioredoxin cDNA increases their growth rate and cell saturation density in culture (normal NIH 3T3 cells are highly contact inhibited) which is in vitro evidence of transformation. It has also been shown that transfection of MCF-7 human breast cancer and HT-29 human colon carcinoma cells with human thioredoxin cDNA increases their colony formation in soft agarose and tumor growth by HT-29 colon cancer cells when the cells are inoculated into immunodeficient (Scid) mice.

Trx was originally studied for its ability to act as a cofactor for ribonucleotide reductase, the first unique step in DNA synthesis (Laurent, T. C. et al., *J. Biol. Chem.*, 239:3436–3444, 1964). Human Trx was subsequently shown to modulate the DNA binding of several transcription factors that regulate cell proliferation, including nuclear factor KB (Hayashi, T. et al., *J. Biol. Chem.* 268:11380–11388, 1993), the glucocorticoid receptor (Grippo, J. F. et al., *J. Biol. Chem.* 258:13658–13664, 1983), and, indirectly through the nuclear redox protein Ref-1, activator protein-1 (Fos/Jun heterodimer; Abate, C. et al., *Science* (Washington D.C.), 249:1157–1161, 1990). Cloning and sequencing of human Trx have shown that it has a predicted amino acid sequence (Gasdaska, P. Y. et al., *Biochem. Biophys. Acta.*, 1218:292–296. 1994: Deiss. L. P. et al., *Science* (Washington D.C.), 252:117–120, 1991) identical to that of a growth factor secreted by virus-transformed leukemic cell lines, termed adult T-cell leukemia-derived factor (Tagaya, Y. et al., *J. Immunol*, 140:2614–2620, 1988; Wakasugi, N. et al., *Proc. Natl. Acad. Sci. USA*, 87:8282–8286, 1990). Human Trx, but not bacterial Trx, added to the culture medium stimulates the growth of a variety of normal and cancer cell lines (Wakasugi, N. et al., *Proc. Natl. Acad. Sci. USA*, 87:8282–8286, 1990; Yodoi, J. et al., *Adv. Cancer Res.*, 57:381–411, 1991; Oblong, J. E. et al., *J. Biol Chem.*, 269:11714–11720, 1994). The added Trx is not taken up by cells (Gasdaska, J. R. et al., *Cell Growth & Differ.*, 6:1643–1650, 1995) and appears to stimulate cell growth by enhancing the action of other growth factors (Gasdaska, J. R. et al., *Cell Growth & Differ.*, 6:1643–1650, 1995; Tagaya, Y. et al., *EMBO J.*, 8:757–764, 1989). The redox activity of Trx is required for growth stimulation, and redox-inactive mutant Trxs do not stimulate cell growth (Oblong, J. E. et al., *J. Biol Chem.*, 269:11714–11720, 1994).

Trx mRNA levels are increased compared with corresponding normal tissue in almost half human primary lung (Gasdaska, P. Y. et al., *Biochem. Biophys. Acta.*, 1218:292–296, 1994) and colon tumors examined (Berggren, M. et al., *Anticancer Res.*, (in press) 1996). Trx protein has been reported to be increased in human cervical neoplastic squamous epithetial cells (Fujii, S. et al., *Cancer* (Phila.), 68:1583–1591, 1991) and hepato-cellular carcinoma (Nakamura, H. et al., *Cancer* (Phila.), 69:2091–2097, 1992). Trx is excreted from cells (Ericson, M. L. et al., *Lymphokine Cytokine Res.*, 11:201–207, 1992; Rubartelli, A. et al., *J. Biol. Chem.*, 267:24161–24164, 1992; Rubartelli, A. et al., *Cancer Res.*, 55:675–680, 1995) using a leaderless secretory pathway. (Rubartelli, A. et al., *J. Biol. Chem.*, 267:24161–24164, 1992), and we have suggested that Trx might be a growth factor for some human cancers (Gasdaska, J. R. et al., *Cell Growth & Differ.*, 6:1643–1650, 1995). However, it remains to be unequivocally demonstrated that endogenously produced Trx can affect cell proliferation. The role Trx plays in the transformed phenotype or cancer cells also is not known.

To provide some answers to these questions, we have stably transfected murine NIH 3T3 fibroblast-like cells and human MCF-7 breast cancer cells with cDNA for human wild-type Trx or with cDNA for a redox-inactive mutant Trx. We have found that transfection with Trx increases the density to which the NIH 3T3 cells grow in culture and stimulates anchorage-independent colony formation by MCF-7 breast cancer cells. The redox-inactive mutant Trx acted in a dominant-negative manner, so that transfected MCF-7 cells showed inhibited growth and a reversal of the transformed phenotype, assessed by growth in vitro and in vivo.

4.3.1 Materials and Methods

Human wild-type Trx cDNA and cDNA for C32/C35S redox-inactive Trx, in which both active-site cysteine residues are replaced by serine (Oblong, J. E. et al., *J. Biol. Chem.*, 269:11714–11720, 1994), were prepared as described previously (Gasdaska, P. Y. et al., *Biochem. Biophys. Acta.*, 1218:292–296, 1994; Oblong, J. E. et al., *J. Biol. Chem.*, 269:11714–11720, 1994). The cDNAs were cloned into either the KpnI or SacI sites of the pRXneo mammalian transfection vector, under constitutive control of the Rous sarcoma virus promotor (Dieken, E. S. et al., *Mol. Cell. Biol.*, 12:589–597, 1992), or into the NotI site of the pDC304neo mammalian transfection vector, in which constitutive expression is driven by the cytomegalovirus and SV-10 promoters (Gordon, D. A. et al., *Exp. Cell. Res.*, 217:368–377, 1995). Correct orientation of the cDNAs in the vectors was confirmed by restriction digestion. The pRXneo and pDC304neo vectors were obtained from Dr. Roger Miesfeld (University of Arizona, Tucson, Ariz.).

Human MCF-7 breast cancer cells and murine NIH 3T3 cells were obtained from the American Tissue Type Collection (Rockville, Md.), maintained in DMEM containing 10% FBS under 6% $CO_2$ at 37° C., and passaged before confluence. NIH 3T3 cells were transfected with Trx:pRXneo, Trx:pDC304neo, C32S/C35S:pDC304neo, or pRXneo alone. MCF-7 cells were transfected with Trx:pDC304neo, C32S/C35S:pDC304neo, or pDC304neo alone. Transfection used liposomes of N-[1,2,3-dioleolylpropyl]-N,N,N,-trimethylammoniummethylsulfate (Boehringer Mannheim, Indianapolis, Ind.) according to the manufacturer's instructions. Cells were selected by growing for 4 weeks in DMEM with 10% FBS and 400 µg/ml G418 sulfate (Life Technologies, Gaithersburg, Md.). Cell colonies were isolated by trypsinization onto small squares of sterile filter paper and expanded by growing in the same medium. All studies were conducted on clonal cell lines between passages 3 and 10.

Northern hybridization analysis of Trx and C32S/C35S mRNA used a full-length [$\alpha$-$^{32}$P]dCTP-labeled human Trx cDNA probe as described previously (Gasdaska, P. Y. et al., *Biochem. Biophys. Acta.*, 1218:292–296, 1994), and the blots were quantified using a PhosphorImager (Molecular Dynamics, Sunnyvale, Calif.). Transfected Trx and C32S/C35S mRNA levels were expressed relative to endogenous Trx mRNA levels in the cells. Western analysis of lysates from Trx and C32S/C35S-transfected MCF-7 cells, prepared by sonicating the cells in 20 mm Tris-HCl buffer (pH 8.0), 137 mm NaCl, 1 mm MgCl$_2$, 1 mm CaCl$_2$, 10% glycerol, 1% Triton X-100, and 1 mm phenylmethylsulfonyfluoride, or in DMEM in which the cells had been incubated at 37° C. for 6 h, was performed using immunoaffinity-purified rabbit polyclonal IgG raised against human Trx (Gasdaska, J. R. et al., *Cell Growth & Differ.*, 6:1643–1650, 1995) which also recognizes C32S/C35S. Detection used the enhanced chemiluminescence system (Amersham Life Sciences, Rockford, Ill.), and quantification of autoradiograms was by densitometry (Eagle Eye II, Stratagene, La Jolla, Calif.).

Colony formation by MCF-7 cells was measured in soft agarose with DMEM and 10% FBS over 7 days, as described previously, (Alley, M. C. et al., *Br. J. Cancer*, 52:205–224, 1985). Growth of cells on plastic surfaces with DMEM and 10% FBS was measured daily for NIH-3T3 cells over 4 days and for MCF-7 cells over 7 days, as described previously (Powis, G. et al., *Biochem. Pharmacol.* 36:2473–2479, 1987). All cell growth studies were conducted in the absence of G418 sulfate.

Tumor formation by transfected NIH 3T3 cells was studied by the s.c. injection of $10^7$ transfected cells in 0.1 ml of sterile 0.9% NaCl into the backs of groups of four male Scid mice or six nude mice. Tumor formation by MCF-7 cells was studied by injecting 2×$10^7$ cells in 0.1 ml of sterile 0.9% NaCl and 0.1 ml of Matrigel (Becton Dickinson, Bedford, Mass.) s.c. into the backs of groups of four female Scid mice that had been implanted s.c. 2 days previously with 21-day release pellets of 0.25 mg of 17-$\beta$-estradiol (Innovative Research, Sarasota, Fla.). The 17-$\beta$-estradiol pellet was replaced at 21 days. Tumor volume was measured with calipers (Geran, R. I. et al., *Cancer Chemother. Rep.*, 3:1–103, 1972) twice a week for 40 days. At the end of the study, the animals were killed, and tumors and other organs were taken for histological analysis.

Statistical analysis was by nonpaired test unless otherwise stated. Tumor growth rates in Scid mice were linearized using the cube root of the tumor volume by day for each mouse, and ANOVA was performed using Dunnett's test to determine significant differences form the vector alone-transfected (control) cell line.

4.3.2 Trx and C32S/C35S Transfection of NIH 3T3 Cells

Transfection of mouse NIH 3T3 cells with Trx:pRXneo yielded 6 clones stably expressing Trx mRNA, transfection with Trx:pDC304 yielded 4 clones, and transfection with C32S/C35S:pDC304 neo yielded 12 clones. The levels of transfected mRNA in some of the clones is shown in FIG. 6. The human Trx and C32S/C35S mRNAs were larger than the endogenous mouse Trx mRNA, probably because the transfected Trx mRNAs also contain portions of the vector promoter region, the 5' leader sequence, or the polyadenylate tail The level of transfected Trx mRNA expression was relatively low, being only 0.2–1.4-fold the endogenous mouse Trx mRNA. Western blotting showed no significant increase in the level of Trx protein in the cells compared with wild-type or vector alone-transfected cells (results not shown).

The Trx-transfected NIH 3T3 cells grew at the same rate on a plastic surface, but reached saturation densities up to twice that of the vector alone-transfected NIH 3T3 cells (FIG. 7). The vector alone-transfected cells had the same growth characteristics of wild-type NIH 3T3 cells. NIH 3T3 cells transfected with the redox-inactive C32S/C35S Trx grew more slowly and reached a lower saturation density on a plastic surface than the vector alone-transfected cells. Neither the vector alone-transfected NIH 3T3 cells nor the Trx or C32S/C35S Trx transfected cells formed colonies in soft agarose (results not shown).

The ability of transfected NIH 3T3 cells to form tumors when inoculated into immunodeficient mice is used to identify neoplastic transforming genes (Pitot, H. C. Fundamentals of Oncology, p. 149. New York: Marcel Dekker, Inc., 1981). When the Trx-transfected NIH 3T3 cells Thio6 or ThioAD were injected i.m. into Scid or nude mice, there was no tumor formation over 40 days (results not shown). Thus, Trx expression. at least at the level obtained in this study, was not, by itself, transforming.

4.3.3 Trx and C32/C35S Transfection of MCF-7 Breast Cancer Cells

Human solid cancer cells generally show a greater proliferation response to added Trx than do mouse fibroblasts (Oblong, J. E. et al., *J. Biol. Chem.*, 269:11714–11720, 1994; Gasdaska, J. R. et al., *Cell Growth & Differ.*, 6:1643–1650, 1995). This is shown for MCF-7 human breast cancer cells compared with NIH 3T3 cells in FIG. 8. Thus, we also studied the effects of Trx transfection using MCF-7 breast cancer cells. Transfection of MCF-7 cells with Trx:pDC304neo yielded 31 clones that stably overexpressed Trx mRNA, and transfection with C32S/C35S:pDC304neo yielded 45 clones stably expressing C32S/C35S mRNA. Expression of transfected mRNAs by some of the clones is shown in FIG. 9. As seen previously with the mouse cells, the transfected human Trx mRNAs in MCF-7 cells were larger than endogenous human Trx mRNA. The level of Trx mRNA expression was up to 0.8-fold and C32S/C35S mRNA up to 2.1-fold of the endogenous Trx mRNA levels. Light microscopy showed no difference in the appearance of vector alone-transfected and Trx-transfected MCF-7 cells growing on glass coverslips (FIG. 10), and both were similar to wild-type MCF-7 cells. In contrast, C32S/C35S-transfected MCF-7 cells appeared more rounded and had a reduced cytoplasm-to-nucleus ratio.

Quantitative Western immunoblotting showed no significant increase in the level of Trx protein in the transfected MCF-7 cells compared with vector alone-transfected MCF-7 cells except for one clone (Table 1). There was, however, a significant 60% increase in the secretion of Trx into the medium by three of the clones compared with the vector alone-transfected MCF-7 cells. The three other clones showed a 20–50% increase of Trx in the medium, but this was not statistically significant. Thus, it appears that most of the extra Trx and C2S/C35S produced by the transfected cells is secreted into the medium.

All of the transfected MCF-7 cells showed linear growth characteristics on plastic surfaces over 7 days. The Trx-transfected cells grew at the same rate as the vector alone-transfected MCF-7 cells (FIG. 11). However, when grown in the absence of, or with 0.5% FBS for 2 days, the Trx-transfected cell grew at twice the rate of the vector alone-transfected cells (results not shown). The C32S/C35S-transfected cells grew at a significantly slower rate that was 56–78% of the vector alone-transfected cells (FIG. 11). Colony formation was significantly increased between 3- and 4-fold for the Trx-transfected MCF-7 cells compared with the vector alone-transfected cells, and significantly decreased up to 73% for the C32S/C35S-transfected cells when the cells were grown in soft agarose. The vector alone-transfected cells showed growth characteristics identical to those of wild-type MCF-7 cells under all conditions (results not shown).

4.3.4 Tumor Formation by Trx- and C32s /C35s Transfected MCF-7 Cells

The vector alone-transfected MCF-7 cells injected into Scid mice formed tumors that grew at the same rate as nontransfected MCF-7 cells we have seen in other studies. Trx-transfected MCF-7 cells formed tumors in Scid mice, although they grew at a significantly slower rate than tumors formed by vector alone-transfected cells: 57% for Trx 12 cells and 38% for Trx 20 cells (both $P<0.05$ by least squares regression analysis; FIG. 12). Tumor formation by the C32S/C35S-transfected MCF-7 cells was almost completely suppressed. Tissues from the injection site and other organs were taken for histological examination at the end of the study. The animals injected with vector alone or Trx-transfected cells showed large solid tumors. The animals injected with C32S/C35S-transfected cells showed small microscopic tumor cell deposits. There was no evidence of tumor metastasis to other organs in any of the animals. Northern analysis of the tumor taken from animals injected with Trx-transfected cells showed the presence of transfected Trx mRNA as determined by its large size (results not shown).

TABLE 1

Trx Levels in Transfected Mcf 7 Breast Cancer Cells and Media
Trx or redox-inactive C32S/C35S (Serb)-transfected MCF-7 breast cancer cells ($10^6$) were incubated in 5 ml of DMEM for 6 hr. and Trx in the original cell pellet or in the medium measured by quantitative Western immunoblotting. Values are a mean of three separate determinations expressed relative to vector alone-transfected cells.

| Clone | Cell[a] | Medium |
|---|---|---|
| MCF-7 vector | 1.0 ± 0.0 | 1.0 ± 0.0 |
| Trx 9 | 0.9 ± 0.0 | 1.6 ± 0.5* |
| Trx 12 | 1.2 ± 0.1* | 1.2 ± 0.2 |
| Trx 20 | 1.1 ± 0.1 | 1.5 ± 0.2 |
| Serb 4 | 0.9 ± 0.1 | 1.6 ± 0.6* |
| Serb 15 | 0.8 ± 0.2 | 1.3 ± 0.2 |
| Serb 19 | 1.2 ± 0.1* | 1.6 ± |

[a]*$P < 0.05$ by a nonpaired t test compared with vector alone-transfected cells.

4.3.5 Discussion

Trx regulates the redox state and activity of a number of intracellular proteins that control cell growth, including ribonucleotide reductase (Laurent, T. C. et al., *J. Biol. Chem.*, 239:3436–3444, 1964) and the DNA binding of several transcription factors (Hayashi, T. et al., *J. Biol. Chem.* 268:11380–11388, 1993; Grippo, J. F. et al., *J. Biol. Chem.*, 258:13658–13664, 1983; Abate, C. et al.,*Science* (Washington D.C.), 249:1157–1161, 1990). Recombinant human Trx added to normal and cancer cells in culture stimulates their proliferation (Gasdaska, J. R. et al., *Cell Growth & Differ.*, 6:1643–1650, 1995). However, it has not been demonstrated that endogenously produced Trx can stimulate cell proliferation. Furthermore, the role Trx may play in malignant transformation of cells is not known. The present study was undertaken to address some of these questions. NIH 3T3 cells transfected with Trx showed an increased cell saturation density when grown as a monolayer on plastic surfaces. Loss of contact inhibition is a feature of transformed cells (Pitot, H. C. *Fundamentals of Oncology*, p. 149. New York: Marcel Dekker, Inc., 1981), and the cell saturation density of the Trx-transfected NIH 3T3 cells was similar to that seen with other transformed, weakly tumorigenic mouse 3T3 cell lines (Schlager, J. J. et al., *Cancer Res.*, 53:1338–1342, 1993). However, the Trx-transfected NIH 3T3 cells did not form tumors when inoculated into immunodeficient mice. The Trx-transfected MCF-7 cells did not show increased growth on plastic surfaces in normal FBS, but exhibited significantly increased anchorage-independent growth measured by colony formation in soft agarose. It is surprising that when the Trx-transfected MCF-7 cells were grown as xenografts in Scid mice, they exhibited decreased growth rate compared with vector alone-transfected MCF-7 cells. This may be because human Trx can stimulate the immune system of mice so that Trx secreted by the transfected MCF-7 cells might promote some immune rejection, even by the Scid mice, which, although deficient in mature B and T lymphocytes, have natural killer-, myeloid-, and antigen-presenting cells (Shultz, L. D. Am. *J. Anat.*, 191:303–311, 1991).

Both NIH 3T3 and MCF-7 breast cancer cells transfected with the C32S/C35S Trx showed slowed growth rates on a plastic surface. In addition, colony formation by MCF-7 breast cancer cells in soft agarose was considerably decreased. When injected into Scid mice, the C32S/C35S-transfected MCF-7 cells formed only microscopic tumors. C32S/C35S is a redox-inactive mutant Trx that acts as competitive inhibitor of Trx reductase (Oblong, J. E. et al., *J. Biol. Chem.*, 269:11714–11720, 1994). Our X-ray crystallographic studies have identified a highly conserved 12 amino acid hydrophobic surface on mammalian, but not bacterial, Trxs, which stabilizes the $Cys^{73}$-mediated disulfide-bonded dimer (Weichsel, A. et al. *Structure*, 4:735–751, 1996). The physiological function of this $Cys^{73}$-$Cys^{73}$ linked Trx dimer is not known. The surface structure of C32S/C35S is very similar to that of Trx (Weichsel, A. et al., *Structure*, 4:735–751, 1996) so that C32S/C35S is likely to participate in the formation of a heterodimer with Trx and thus might lower Trx monomer concentrations or affect the biological activity of the dimer. Unlike wild-type Trx, C32S/C35S does not stimulate cell growth when added to the culture medium. C32S/C35S might also act as a competitive inhibitor to the normal redox-active substrates of Trx. Whatever the mechanism, it appears that C32S/C35S acts in a dominant-negative manner to inhibit the effects of endogenous Trx and, in so doing, inhibits cell growth and reverses the transformed phenotype of MCF-7 breast cancer cells.

Most of the added Trx or C32S/C35S protein that is produced by the transfected cells appears to be secreted into the medium. Whether the transfected Trx is produced in a different compartment to endogenous Trx, allowing it to be secreted, or whether a constant proportion of Trx is secreted is not known. Trx is known to be secreted from cells by a leaderless secretory pathway (Rubartelli, A. et al., *J. Biol. Chem.*, 267:24161–24164, 1992). The concentrations of Trx found in the medium, up to 10 nm after 6 hr. are lower than those required to directly stimulate cell proliferation (Gasdaska, J. R. et al., *Cell Growth & Differ.*, 6:1643–1650, 1995). However, we have recently found that Trx at nanomolar concentrations will potentiate the growth effects of cytokines such as interleukin-2 and basic fibroblast growth factor. It remains to be established whether the extra Trx is producing its effects on cell proliferation through an intracellular or an extracellular action. It should be noted that Trx binds to the surface of cells (Gasdaska, J. R. et al., *Cell Growth & Differ.*, 6:1643–1650, 1995; Ifversen, P. et al., *Hum. Antib. Hybrid.*, 4:115–123, 1993) so that secreted Trx could have a local effect at the outer cell surface although concentrations in the medium are low.

The levels of transfected Trx mRNA in cells were not high, only up to 1-fold endogenous Trx mRNA levels, and were independent of the mammalian transfection vector used. Typically mRNA levels resulting from transfection using such vectors are 10–50-fold or higher (Powis, G. et al., *Anticancer Res.*, 15:1141–1146, 1995). It may be that high levels of Trx gene expression are toxic to cells. We have found only a low expression of the human Trx gene in transgenic mice. In contrast, some human tumors show very high levels of Trx mRNA compared with the normal tissue: more than 11-fold in human primary lung tumors (Gasdaska, P. et al., *Proc. Am. Assoc. Cancer Res.*, 34:62, 1993) and even higher in human primary colon tumors (Berggren, M. et al., *Anticancer Res.*, 17:3371–3380, 1997). It is not known why higher Trx mRNA levels could not be obtained in transfected cells. We were unable to obtain transformation of NIH 3T3 cells with Trx. It remains to be demonstrated whether the much higher levels of Trx expression seen in some human tumors might be transforming.

The observation that a redox-inactive dominant-negative Trx reverses the transformed phenotype of MCF-7 cells suggests that drugs that inhibit the redox activity of Trx might offer a novel approach to treating some forms of human cancer. Alternatively, inhibiting the enzyme responsible for the reduction of Trx, the flavoprotein Trx reductase, might also lead to a selective inhibition of cancer cell growth. We have shown previously that some antitumor quinones, including doxorubicin and diaziquone, are mechanism-based (suicide substrate) inhibitors of Trx reductase both in the purified form and in intact cells (Mau, B. L. et al., *Biochem. Pharmacol.*, 43:1621–1626, 1992). However, the antitumor quinones have many other effects that could contribute to their antitumor activity (Powis, G. *Pharmacol. Ther.*, 35:157–162, 1987). On the basis of our transfection studies, it would be of great interest to see what effect selective inhibitors of Trx or its reductase have on cancer cell growth and transformation.

In summary, our results have shown that stable transfection of nontransformed mouse fibroblast-like cells and human breast cancer cells with human Trx leads to low levels of overexpression and increased cell saturation densities but no transformation, measured by tumor formation of NIH 3T3 cells in immunodeficient mice. Stable transfection with redox-inactive mutant Trx results in a dominant-negative effect with inhibition of mouse cell and human breast cancer cell growth and reversion of the transformed phenotype of human breast cancer cells, measured by their ability to form colonies in soft agarose and to form tumors in mice. The Trx produced appears to be secreted mostly from cells, and whether the Trx is having an intracellular or extracellular action remains to be determined.

In the majority of the subjects tested (8/10), human primary gastric carcinomas thioredoxin was over-expressed in tumor cells compared to normal mucosa, and in all cases the over-expression was found only in the cancer cells and not in stromal cells or infiltrating lymphocytes. Levels of thioredoxin significantly higher than in normal dividing cells, were found in 5/8 of the over-expressing carcinomas. To relate thioredoxin over-expression to cell proliferation and apoptosis, nuclear proliferation antigen was detected by Ki67 antibody and apoptosis by the in situ terminal deoxynucleotidyl transferase (TUNEL) assay were measured in the same tissue samples. (See Table 2). Thioredoxin expression was significantly and highly positively correlated with nuclear proliferation antigen (p<0.01) a marker of aggressive tumor growth and highly negatively correlated with apoptosis (p<0.001) a form programmed cell death that is presumed to limit tumor growth. Thus, thioredoxin is over-expressed at the mRNA and protein level in a number of human primary tumors. Further, the expression of thioredoxin protein is directly associated with highly proliferative tumors.

TABLE 2

Staining of Thioredoxin in Human Gastric Cancers:
Comparison with Cell Proliferation and Apoptosis Staining scored as absent (0) or weak (+) to intense (++++)

| Patient # | Thioredoxin Normal* | Thioredoxin Tumor | Tumor Proliferation Ki-67 | Tumor Apoptosis Tunel |
|---|---|---|---|---|
| 1. | ++ | ++++ | +++ | + |
| 2. | ++ | +++ | +++ | + |
| 3. | ++ | ++++ | NE | + |
| 4. | ++ | ++++ | ++++ | + |
| 5. | ++ | +++ | +++ | ++ |
| 6. | ++ | 0 | + | ++++ |
| 7. | ++ | + | + | +++ |
| 8. | ++ | 0 | + | ++++ |
| 9. | ++ | ++ | +++ | +++ |
| 10. | ++ | ++ | NE | ++ |

*= gastric pits; NE = non evaluable

MCF-7 human breast cancer cells were transfected with cDNA for thioredoxin or with a catalytic site redox-inactive mutant thioredoxin, C32S/C35S. using two constitutive eukaryotic expression vectors (pRXneo and pDC304neo) and a number of clones were selected for each. The level of transfected thioredoxin and C32S/C35S thioredoxin mRNA was up to 2-fold the endogenous message. Both types of transfected cells showed increased thioredoxin protein production, measured by quantitative Western blotting, up to 100% that of mock-transfected cells.

There was little difference in the growth of the transfected cells formed up to 4-fold more colonies when grown in soft agarose and the C32S/C35S transfected cells formed up to 80% fewer colonies as illustrated in FIGS. 4A–B.

When these cells were injected into Scid mice the thioredoxin transfected cells formed tumors while the C32S/C35S transfected cells did not form tumors, as illustrated in FIG. 5. This was confirmed by histology. Thus, a dominant-negative redox inactive thioredoxin can reverse the transformed phenotype and inhibits tumor growth in vivo providing molecular biology evidencing that thioredoxin is a novel target for anti-cancer drug development.

4.4 Use of Thiordoxin as an Anti-Tumor Drug Target

Although thioredoxin is a known protein, it has not been disclosed or suggested that thioredoxin be used as a screen for anti-tumor agents. It has now been shown that stable transfection of the MCF-7 breast cancer cells with a redox-inactive mutant thioredoxin causes inhibition of anchorage-independent growth of the cells in soft agarose and causes complete inhibition of tumor formation in vivo. The redox-inactive mutant is formed from thioredoxin where the catalytic site cysteine residues are replaced with serine. Further, it was shown that the mutant thioredoxin did not inhibit monolayer growth of the cells, i.e., does not inhibit normal cell growth, while it causes inhibition of anchorage-independent growth of the cells in soft agarose, i.e., does inhibit an in vitro characteristic of tumor cell growth. This is the activity that would be expected from drugs that inhibit thioredoxin.

4.4.1 Examples of Agents that Inhibit Thioredoxin

Agents that inhibit thioredoxin have been identified in accordance with the present invention, such agents may be antibodies, drugs or antisense. A series of unsymmetrical 2-imidazolyl disulfides were investigated as inhibitors of the thioredoxin system and as potential anti tumor agents. Although these agents were originally identified as competitive inhibitors of thioredoxin reductase (Oblong J E, et al., *Cancer Chemother. Pharmacol*, 34:434–438, 1994) but it has now been shown that they also to bind irreversibly to $Cys^{73}$ of thioredoxin and to block its reduction by thioredoxin reductase. A number of these disulfide compounds have been studied and have demonstrated anti-tumor activity against human tumor xenografts in Scid mice with up to 90% inhibition of MCF-7 breast cancer and HL-60 promyelocytic leukemia growth. It has now been demonstrated that the imidazolyl disulfides inhibit thioredoxin-dependent cell growth (Oblong J E, et al., *Cancer Chemother. Pharmacol.*, 34:434–438, 1994) and that their growth inhibitory activity in the National Cancer Institute 60 human tumor cell line panel correlates with levels of thioredoxin mRNA in these cell lines (Berggren M, et al., *Anticancer Res.*, 16:3459–3466, 1996). A COMPARE correlative analysis of the activity of the lead disulfide compounds in the NCI cell line panel with over 50,000 compounds already tested for cell growth inhibition by the NCI was conducted in order to identify compounds with a similar pattern of growth inhibitory activity: Some of the compounds identified in this way were inhibitor of thioredoxin reductase and some were inhibitors of thioredoxin.

4.5 Use of Thioredoxin Reductase as a Target for Inducing Anti-Proliferation

Although the general properties of human thioredoxin reductase as a protein and the cDNA base sequence of human thioredoxin reductase has been known in the art, it has now been discovered that thioredoxin reductase is useful as an anti-cancer drug target. It has now been shown above that redox activity is necessary for the growth stimulating activity of thioredoxin. Since thioredoxin reductase is the only known way for thioredoxin to be reduced biologically it is an obvious extension of the above observations that thioredoxin reductase could also be a target for the development of anti-cancer drugs.

4.6 Use of Recombinant Modified Thioredoxin for Stimulating Cell Growth

It has been discovered that human thioredoxin, and specifically recombinant modified thioredoxin (mutated thioredoxin), does not undergo spontaneous oxidation and/or dimer formation, or protected against breakdown by blood and tissues, may have therapeutic utility in situations where stimulation of cell growth is preferred or required. In a non-limiting embodiment of the present invention, such new uses include, and are not limited to, the beneficial use of thioredoxin and/or recombinant modified thioredoxin in stimulating cell proliferation in individuals (1) with myelodysplastic syndrome; (2) in need of bone marrow transplantation; (3) with post-chemotherapy to stimulate bone marrow growth; (4) in need of stimulation of the immune system; (5) in need of stimulation of wound healing; (6) such as transgenic animals in need of stimulation of body growth; (7) in need of simulation of the responses to sytokines and growth factors for growth stimulation effects; and (8) in gene therapy techniques.

The underlying defect in myelodysplastic syndrome is decreased multilineage progenitor cell growth associated with decreased sensitivity to growth factor stimulation. Thioredoxin acts to increase the sensitivity of cells to growth factors and stimulates multilineage progenitor cells which provides a beneficial utility in individuals with MDS.

In individuals in need of bone marrow transplantation, it would be of great utility to promote the growth of transplanted cells. Thioredoxin may be used to protect hematopoietic progenitor cells and to expand cells ex vivo for bone marrow cell growth. This would rely on a selective effect for bone marrow since tumor cells might also be stimulated by the thioredoxin.

It would provide a great benefit to individuals subject to chemotherapy treatment to selectively stimulate bone marrow cell growth post-chemotherapy.

It has been found that Cys73→Ser mutant thioredoxin will stimulate the proliferation of human immune cells in culture, which can provide a great benefit to individuals in need of stimulation of immune system cells.

Wild-type and Cys73→Ser mutant thioredoxin also stimulates the growth of fibroblasts, which are important components of wound healing process. There would be a great advantage of using thioredoxins to stimulate wound healing, for example after surgery.

It has been found that wild-type thioredoxin expressed as a transgene in mice may be lethal or is only weakly expressed. Therefore, it is possible that construction of transgenes with wild-type or mutant forms of thioredoxin, with or without tissue specific and/or inducible promoters, could be used to stimulate the development of the animal or the growth of selected organs.

It has been found that thioredoxin can potentiate the response of cells in culture to growth factors and cytokines such as IL-2 and basic fibroblast growth factor (bFGF). Combinations of thioredoxin with other growth factors or cytokines therefore increases the therapeutic usefulness of these growth factors where increased cell proliferation is the desired therapeutic effect.

Introduction of the thioredoxin or mutant thioredoxin genes into human cells provides a mechanism of improving the therapeutic usefulness of other cytokines or growth factors given directly or themselves as gene therapy, for example IL-2.

4.6.1 Examples of Stimulation of Cell Growth Using Thioredoxin Protein

Although thioredoxin mRNA has been found to be over expressed by some human tumor cells, it has been discovered that thioredokin, specifically recombinant modified thioredoxin also stimulates cell growth.

A novel mechanism or over-expression and secretion from the cells by a leaderless secretory pathway has important consequences for potential therapeutic uses of thioredoxin as explained below. It has been discovered that human recombinant thioredoxin undergoes spontaneous oxidation in air to give a form that will not stimulate cell growth. This spontaneous oxidation appears to involves Cys73 since a mutant thioredoxin where this residue has been converted to serine (Cys73→Ser thioredoxin) does not undergo this loss of activity. X-ray crystallography studies of wild-type and C73S thioredoxin show that thioredoxin has a highly conserved hydrophobic dimer forming surface and that Cys73 stabilizes homodimer formation through a Cys73—Cys73 disulfide bond (Weichsel A, et al. Structure 4:735–751

(1996)). The active site Cys residues become relatively inaccessible in the thioredoxin homodimer so that it is a very poor substrate for thioredoxin reductase. The thioredoxin homodimer does not stimulate cell proliferation. The half life of recombinant human thioredoxin in phosphate buffered 0.9% NaCI at −20° C. is 6–8 days. Thus, the wild type thioredoxin is not a good protein for therapeutic use because of is tendency to oxidize and lose biological activity.

It has been found that wild-type thioredoxin loses its ability to stimulate cell proliferation even over a few days even before formation of the Cys73—Cys73 disulfide stabilized dimer. This appears to be due to modification of the monomeric form of thioredoxin possibly involving reversible dimerization without covalent linkage, or to other oxidative events in the protein. In contrast, it has been found that Cys73→Ser thioredoxin is stable in solution over several weeks, even at room temperature, and does not dimerize. Cys73→Ser thioredoxin is as effective as wild-type thioredoxin at stimulating cell proliferation and retains this ability with no loss over many days and, thus, appears to be more suitable as a potential therapeutic agent.

In order to investigate whether thioredoxin and mutant thioredoxin proteins have activity in intact animals I studied the ability of the Cys73→Ser mutant thioredoxin to prolong the life of mice that had been lethally γ-irradiated and which, if untreated, die from bone marrow suppression as shown in Table 3. Mice that had been injected with the Cys73→Ser mutant thioredoxin survived 850 Gy γ-radiation whereas non-injected mice died. Thus, Cys73→Ser mutant thioredoxin can prevent the death of lethally y-irradiated mice. While not wishing to be bound to any particular theory, it is presumed that this effect is due to stimulation of bone marrow cell growth.

TABLE 3

Protection Against Radiation Induced Death by Cys73→Ser Mutant Thioredoxin
Mice received 8.5 Gy γ-irradiation. One group of mice was treated with Cys73→Ser thioredoxin in 0.9% NaCl 0.85 mg/mouse injected i.v. 30 min before and 24 hr. after radiation. There were 6 mice in the control group and 4 mice in the treated group. The study was terminated on day 30.

| mouse | control day of death | Cys72→Ser thioredoxin day of death |
|---|---|---|
| 1 | 11 | alive |
| 2 | 16 | alive |
| 3 | 16 | alive |
| 4 | 16 | alive |
| 5 | 17 | alive |
| median | 16 ± 2.1 | alive |

Evidence that Cys73→Ser mutant Thioredoxin stimulates the growth of bone marrow was obtained directly by adding Cys73→Ser mutant thioredoxin directly to human bone marrow and studying its effects on colony formation by the cells, as illustrated in FIG. 1. Cys73→Ser mutant thioredoxin stimulates colony formation by the muitilineage progenitor cells (CFU-GEMM) but does not stimulate the lineage specific erythroid progenitor (BFU-E) and myeloid progenitor (CFU-GM) cells.

FIG. 1 illustrates the stimulation of human bone marrow colony formation by Cys73→Ser mutant thioredoxin, in accordance with the present invention. Human bone marrow was obtained as excess material from normal allogeneic bone marrow donors. The effects of Cys73→Ser thioredoxin on colony formation are shown by (○) multilineage progenitors (CFU-GEMM); (●) erythroid progenitors (BFU-E); and (▼) myeloid progenitors (CFU-GM), as measured over 10 days as described. (Values are the mean of 4 determinations and bars are S.D.) It has further been found that Cys73→Ser thioredoxin can stimulate cell proliferation by increasing the response of the cells to other cytokines or growth factors such as interleukin-2 (IL-2) and fibroblast growth factor (FGF) as illustrated in the chart in FIG. 2. FIG. 2 illustrates potentiation of IL-2 induced MCF-7 breast cancer cell growth by Cys73→Ser mutant thioredoxin, in accordance with the present invention. Cells were growth arrested for 48 hr. in medium with 0.5% serum ($10^5$ cells) then stimulated in the absence of medium with either IL-2 or Cys32→Ser mutant thioredoxin at the concentrations shown. Cell number was measured after 48 hr. Each point on the chart represents the mean of 3 determinations and bars represent S.E. The dotted line shows stimulation by 10% serum.

In addition, antibodies to the receptors for the growth factors can block the response to these agents, in accordance with the present invention as shown in FIG. 3. FIG. 3 illustrates the inhibition of thioredoxin stimulated MCF-7 cell growth by receptor antibodies, in accordance with the present invention. Cell proliferation was measured as described above in the context of FIG. 2. The concentrations of agents used were Cys73→Ser mutant thioredoxin (Thioredoxin) 1 μM; monoclonal antibodies to FGF receptor, IL-2-receptor and EGF-receptor 4 μg/ml; and EGF 10 nM. The EGF and EGFR were added as a negative control. Values represent the mean of 3 determinations and bars represent S.E. The dotted line shows the effect of 10% serum alone.

Therefore, the discovery that human thioredoxin, and specifically recombinant modified thioredoxin, does not undergo spontaneous oxidation and/or dimer formation has a tremendous potential in vivo utility in situations where stimulation of cell growth is required. In addition, it may be advantageous to modify the thioredoxin structure to increase the potency and therapeutic usefulness, such as changing the amino acid sequence at the site of proteolytic cleavage to prevent breakdown by plasma enzymes.

Thioredoxin/mutant thioredoxin may have use after bone marrow transplantation of cancer patients or together with chemotherapy to stimulate bone marrow recovery, or to stimulate the immune system in patients with AIDS. There may be other potential therapeutic applications for thioredoxin/mutant thioredoxin such as increasing the rate of wound healing. If a thioredoxin or mutant thioredoxin gene could be introduced into an animal as a transgene this might result in an increased growth rate of the animal. A thioredoxin transgenic mouse has been developed, although the levels of gene expression are very low and the animal does not show an increased growth rate. However, a gene for mutant thioredoxin might be more effective in this regard. The use of mutant thioredoxins may not be limited to the Cys73→Ser mutant. Mutation of the other Cys residues can also affect biological activity. There are also other amino acid residues on the hydrophobic domain of the molecule that X-ray crystallographic studies have shown might also be important for dimer formation. Mutation of these and possibly other amino acid residues, might alter the biological activity of thioredoxin.

The in vitro cell growth stimulating activity of human thieredoxin has been previously reported for human lymphoid and solid tumor cancer cells (Gasdaska J R, et al., *Cell Growth Differ.*, 6:1643–1650, 1995; Oblong J E, et al., *J. Biol. Chem.*, 269:11714–11720, 1994) and for mouse fibroblast cells (Oblong J E, et al., *J. Biol. Chem.*, 269:11714–11720, 1994). The production of a Cys73→Ser mutant thioredoxin has been previously reported. In one study it did not act like wild-type thioredoxin as a component of a complex cell growth stimulating factor called "early pregnancy factor" (Tonissen K, et al., *J. Biol. Chem.*, 268:22485–22489, 1993). In another study it was reported that Cys73→Ser mutant thioredoxin did not form a dimer, but cell growth stimulating activity by the mutant thioredoxin was not investigated in this study (Ren X, et al., *Biochem.*, 32:9701–9705, 1993). However, the ability of the Cys73→Ser mutant and other mutant thioredoxins to stimulate cell proliferation has not been reported. There have been no prior reports of administration of wild-type or mutant thioredoxins in vivo.

4.6.2 Role of Oxidative Inactivation of Thioredoxin as a Cellular Growth Factor

Thioredoxin (Trx) is a widely distributed redox protein that regulates several intracellular redox-dependent processes and stimulates the proliferation of both normal and tumor cells. We have found that when stored in the absence of reducing agents, human recombinant Trx undergoes spontaneous oxidation, losing its ability to stimulate cell growth, but is still a substrate for NADPH-dependent reduction by human thioredoxin reductase. There is a slower spontaneous conversion of Trx to a homodimer that is not a substrate for reduction by thioredoxin reductase and that does not stimulate cell proliferation. Both conversions can be induced by chemical oxidants and are reversible by treatment with the thiol reducing agent-dithiothreitol. SDS-PAGE suggests that Trx undergoes oxidation to monomeric form(s) preceding dimer formation. We have recently shown by X-ray crystallography that Trx forms a dimer that is stabilized by an intermolecular $Cys^{73}$-$Cys^{73}$ disulfide bond. A $Cys^{73}$→Ser mutant Trx (C73S) was prepared to determine the role of $Cys^{73}$ in oxidative stability and growth stimulation. C73S was as effective as Trx in stimulating cell growth and was a comparable substrate for thioredoxin reductase. C73S did not show spontaneous or oxidant-induced loss of activity and did not form a dimer. The results suggest that Trx can exist in monomeric forms, some of which are mediated by $Cys^{73}$ that do not stimulate cell proliferation but can be reduced by thioredoxin reductase. $Cys^{73}$ is also involved in formation of an enzymatically inactive homodimer, which occurs on long term storage or by chemical oxidation. Thus, although clearly involved in protein inactivation, $Cys^{73}$ is not necessary for the growth stimulating activity of Trx.

Trx is a redox protein found in both eukaryotes and prokaryotes (Holmgren A., *Annu. Rev. Biochem.*, 54:237–271, 1985). The redox activity of Trx arises from a highly conserved Trp-Cys-Gly-Pro-Cys-Lys active site sequence where the 2 cysteine residues (Cys) undergo reversible oxidation to cystine. Reduction of Trx is catalyzed by thioredoxin reductase (Luthman M. et al., *Biochem.*, 21:6628–6633, 1982). Trx was originally identified in *Escherichia coli* as a hydrogen donor for ribonucleotide reductase (Laurent T C. et al., *J. Biol. Chem.*, 239:3436–3444, 1964). Trx has since been found to act as an intracellular dithiol-disulfide reductase and to modulate the activity of a number of intracellular proteins (Fountoulakis M., *J. Biol. Chem.*, 267:7095–7100, 1992; Kistner 25 A. et al., *Toxicon.*, 31:1423–1434, 1993; Silverman R B et al., *Biochem. Biophys. Res. Commun.*, 155:1248–1254, 1988) including the DNA binding of transcription factors (Hayashi T. et al., *J. Biol. Chem.*, 268:11380–11388, 1993; Galter D. et al., *Eur. J. Biochem.*, 221:639–648. 1994; Grippo J F et al., *J. Biol. Chem.*, 258:13658–13664, 1983; Cromlish J A et al. *J. Biol. Chem.*, 264:18100–18109, 1989). Trx-like sequences are found in other proteins including protein disulfide isomerase (Freedman R B et al., *Trends Biochem. Sci.*, 19:331–336, 1994). There is evidence that Trx may play a role in the growth and transformed phenotype of some cancers. Trx is over expressed by a number of human cancers compared with normal tissue (Berggren M. et al., *Anticancer Res.* 17:3377–3380, 1997); Gasdaska P Y et al., *Biochem. Biophys. Acta.*, 1218:292–296, 1994; Nakamura H. et al., *Cancer* 69:2091–2097, 1992). It has recently been shown that transfection of human cancer cells with a dominant-negative mutant human Trx inhibits anchorage-independent growth in vitro and tumor formation in vivo (Gallegos A. et al., *Cancer Res.* 56:5765–5770, 1996).

As well as having intracellular actions, Trx acts exogenously as a redox-active growth factor. Human Trx is identical to the leukemic cell autocrine growth factor adult T-cell leukemic factor (Gasdaska P Y et al., *Biochem. Biophys. Acta.*, 1218:292–296, 1994), and stimulates the growth of both normal fibroblasts (Oblong J E et al., *J. Biol., Chem.*, 269:11714–11720, 1994) and human hematologic and solid tumor cancer cells in culture (Wakasugi N. et al. *Proc. Natl. Acad. Sci USA*, 87:8282–8286, 1990; Gasdaska J R et al., *Cell Growth Differ.*, 6:1643–1650, 1995). Trx appears to act by a helper mechanism that sensitizes the cells to growth factors secreted by the cells themselves (Gasdaska J R et al., *Cell Growth Differ.*, 6:1643–1650, 1995). Mutant human Trxs, where the $Cys^{32}$ and $Cys^{35}$ residues at the catalytic site (numbering of amino acid residues is from the N-terminal methionine, although this may be removed in some forms of Trx) are converted to serines (Ser) either singly or together, are redox inactive and do not stimulate cell growth (Oblong J E et al., *J. Biol. Chem.*, 269:11714–11720, 1994). Trx is secreted from cells by a leaderless secretory pathway (Rubartelli A. et al., *J. Biol. Chem.*, 267:24161–24164, 1992) and could be acting as an autocrine factor for the growth of some cancer cells (Gasdaska J R, et al., *Cell Growth Differ.*, 6:1643–1650, 1995).

We have found that *E. coli* Trx, unlike human Trx, does not stimulate the growth of human solid cancer cells (Gasdaska J R, et al., *Cell Growth Differ.*, 6:1643–1650, 1995). The structures of *E. coli* and human Trx are similar, and both are substrates for human thioredoxin reductase. However, the surface residues of the two forms vary considerably (Weichsel A. et al., *Structure* 4:735–751, 1996). Human Trx has 3 additional cysteine residues, $Cys^{62}$, $Cys^{69}$ and $Cys^{73}$, in addition to those in the active site, which do not normally form intramolecular disulfide bonds (Weichsel A. et al., *Structure* 4:735–751, 1996; Forman-Kay J D et al., *Biochem.*, 30:2685–2698, 1991). Trx can also form a homodimer with al 100 $A^2$ interface domain and a disulfide bond between $Cys^{73}$ from each monomer (Weichsel A. et al., *Structure* 4:735–751, 1996). During our studies of cell growth stimulation by Trx we observed that storage of the Trx without a reducing agent for even a few days resulted in a loss of its growth-stimulating activity, although the Trx remained a substrate for reduction by thioredoxin reductase. We have, therefore, examined the, role of spontaneous and induced oxidation of Trx and cysteine-deleted mutant Trxs, and their ability to stimulate cell proliferation.

4.6.2.1 Preparation of Thioredoxins

Recombinant human Trx and $Cys^{32} \rightarrow Ser/Cys^{35} \rightarrow Ser$ mutant Trx (C32S/C35S) were prepared and purified as previously described (Oblong J E et al., J. Biol. Chem., 269:11714–11720, 1994). $Cys^{73} \rightarrow Ser$ mutant human Trx (C73S) was prepared from single-stranded, sense strand human Trx cDNA ligated by polyethylene glycol precipitation into the pBluescript KS vector (Stratagene, La Jolla, Calif.) using 8408 helper phage. The single-stranded cDNA was used for oligonucleotide-directed in vitro mutagenesis (Version 2.1 Kit, Amersham, Buckinghamshire, U.K.) using oligonucleotide 5'-TGTTGGCATGGATTTGACTTC-3'. Point mutagenesis was confirmed by dideoxy sequencing of base-denatured double-stranded DNA using the Sequenase Version 2.0 kit (USB, Cleveland, Ohio). Novel NdeI and BamHI restricted sites were introduced at the 5' and 3' ends of the mutant Trx cDNA by oligonucleotide-directed PCR. NdeI/BamHI restricted fragments were extracted from agarose gels, ligated into a suitably restricted pET-3a expression vector (Studier F W et al., Methods Enzymol., 185:60–89, 1991), transformed into E. coli BL21 cells and confirmed by dideoxy sequencing. C73S Trx was expressed and purified as previously described (Oblong J E et al., J. Biol. Chem., 269:11714–11720, 1994). All Trxs were stored at $-20°$ as a 25, $\mu$M stock solution in 5 mM DTT. Before use, the DTT was removed by passing the Trx solution through a PD-10 desalting column (Pharmacia, Uppsala, Sweden). The Trx solution was kept at 4° and used within 2 hr. (fresh) or stored in water or 0.1 M potassium phosphate-buffered 0.9% NaCl at 4° or $-20$ ° for specified times. Oxidized Trx for cell growth studies was prepared by adding a 5-fold molar excess of $H_2O_2$, to a 25, um Trx stock solution without DTT and 1 hr. later removing unrecalled $H_2O_2$ using a PD-10 column.

4.6.2.2 Cell Growth Studies

MCF-7 human breast cancer cells were obtained from the American Type Culture Collection (Rockville, Md.), maintained in DMEM containing 10% fetal bovine serum at 37° and 6% $CO_2$, and passaged at 75% confluence. The effect of Trx and modified Trxs on MCF-7 cell growth was determined as previously described (Gasdaska J R et al., Cell Growth Differ., 6:1643–1650, 1995). Briefly, 105 cells were plated in a 35-mm culture dish in DMEM containing 10% fetal bovine serum and, after attachment for 24 hr., growth arrested using DMEM with 0.5% fetal bovine serum for 48 hr. The medium was then replaced with DMEM containing Trx or other additions for 2 days and cell number measured with a hemocytometer. All incubations were conducted in triplicate.

4.6.2.3 Thioredoxin Reductase Assay

Human placenta thioredoxin reductase, specific activity 33.3 $\mu$mol Trx reduced/min/mg protein, was prepared as previously described (Oblong J E et al., Biochem., 32:7271–7277, 1993). Reduction of Trx and C73S by thioredoxin reductase was measured by the oxidation of NADPH at 340 nM with insulin as the final electron acceptor as described by Luthman and Holmgren (Luthman M. et al., Biochem., 21:6628–6633, 1982).

4.6.2.4 Electrophoresis

A 25 $\mu$M solution of fresh Trx, mutant C73S or C32S/C35S Trxs; Trxs that had been aged at room temperature for 48 hr., 7 days, 90 days; or Trxs treated for 1 hr. with 1 mM diamide. 10 mM DTT, 3 mM 2-mercaptoethanol or 2:1 (v:v) $H_2O_2O$, was mixed with an equal volume of loading buffer containing 3% SDS, 10% glycerol and 0.1% bromphenol blue in 0.05 M Tris-HCI, pH 6.8. Approximately 0.02, $\mu$g of the protein was 30 loaded in each lane of a 24×45 cm 16.5% polyacrylamide resolving gel (pH 8.4) containing 0.3% SDS, a 10% spacer gel and a 6% stacking gel and separated by electrophoresis using an anode buffer of 0.2M Tris-HCI, pH 8.9 and cathode buffer of 0.1 M Tris-HCI, 0.1% SDS, pH 8.2. The gel was run for 1 hr. at 400 volts before loading the samples and then at 400 volts for 24 hr. before fixing in 50% methanol, 7.5% acetic acid for 20 min, followed by 5% methanol, 7.5% acetic acid for 20 min, followed by 10% glutaraldehyde for 20 min. The gel was soaked in 2 L $H_2O$ overnight to remove unbound SDS and then silver stained (ICN Silver Stain Kit, Irvine, Calif.). Similar observations were made when the gels were stained with Coomassie Blue.

4.6.2.5 Growth Stimulation $Cys^{73} \rightarrow Ser$ mutant Trx (C73S) stimulated the proliferation of human MCF-7 breast cancer cells. The $EC_{50}$ for growth stimulation by C73S was 350 nM and the maximum effect was seen at 1 $\mu$M, which is similar to values we have previously reported for stimulation of MCF-7 cell proliferation by recombinant human Trx (Gasdaska J R et al., Cell Growth Differ 6:1643–1650, 1995). Storage of Trx in the absence of a reducing agent such as DTT at 4° for 5 days resulted in a 78% loss, and for 90 days a 98% loss of cell growth stimulating activity (FIG. 13). In contrast, C37S showed no loss of activity when stored under these conditions. Trx stored in the presence of bovine catalase at 1 unit/ml did not lose biological activity over a 5-day period (results not shown).

4.6.2.6 Reduction of Thioredoxin by Thioredoxin Reductase

C73S was a good substrate for reduction by human placental thioredoxin reductase with a $K_m$ of 0.20, $\mu$M and a $V_{max}$ of 6.3 nmol/min/,ug. These values are similar to those we have previously found for fresh Trx, which were a $K_m$ of 0.33 $\mu$M and a $V_{max}$ of 5.9 nmol/min/$\mu$g (Oblong J E et al., Biochem., 32:7271–7277, 1993).

The effect of storing Trx without DTT on its ability to act as a substrate for thioredoxin reductase was investigated (Table 4). When stored in $H_2O$ either at $-20°$ or at room temperature Trx showed a loss of activity with a half-life of 20–30 days. The loss of Trx activity was more rapid when stored in phosphate-buffered 0.9% NaCl, with a half life of 8 days. Phosphate buffer is known to contain small amounts of iron (Poyer J L et al., J. Biol. Chem., 246:263–269, 1971), which could catalyze an oxidative process increasing the loss of Trx activity. Alternatively, the lower pH of the solution in water could stabilize Trx or the increase in ionic strength of phosphate-buffered 0.9% NaCl could enhance the formation of the inactive homodimer of Trx. The aged Trx showed a slow, delayed reduction by thioredoxin reductase that was stimulated by catalytic amounts of fresh Trx (FIG. 14). It is important to note that the loss of activity of Trx as a substrate for thioredoxin reductase was much slower than the loss of activity as a stimulator of cell growth. C73S did not show a loss of activity as substrate for thioredoxin reductase upon storage for up to 30 days. The ability of Trx to act as a substrate for thioredoxin reductase was completely inhibited by treatment with 5 molar equivalents of $H_2O_2$, whereas C37S remained fully active after treatment with 100 molar equivalents of $H_2O_2$ (FIG. 15).

TABLE 4

Effect of Storage of Thioredoxins
As Substrates for Thioredoxin Reductase
25 μMstock solution of Trx of C73S in H₂O or phosphate
buffered 0.9% NaCl (PBS) free of D77 were stored frozen at
−20° or at room temperature (+21°) for up to 60 days and their
ability to act as a substrate for reduction by human placental
thioredoxin was measured. A first order decrease in activity
was found for Trx and the results are expressed as half-life ($t_{1/2}$).

|  | In H20 | | In PBS | |
| --- | --- | --- | --- | --- |
|  | −20° $t_{1/2}$ (days) | +21° $t_{1/2}$ (days) | −20° $t_{1/2}$ (days) | −21° $t_{1/2}$ (days) |
| Trx C73S | 30.5 stable* | 20.1 stable* | 8.2 stable* | 7_8 stable* |

*<10% loss of activity over 30 days.

4.6.2.7 Multiple Forms of Thioredoxin

Electrophoretic analysis of freshly prepared human Trx stored in DTT showed a mixture of 5 bands of apparent molecular weights ranging from 8.1 to 11 kDa (FIGS. 16, 17, and 18, lane 1). Storage of Trx at room temperature without DTT resulted in a change in the banding pattern with disappearance of the 8.1-kDa band by 48 hr. (FIG. 16, lane 2). Storage of Trx without DTT for 7 days resulted in the loss of additional bands and the appearance of a new band at 23 kDa due, apparently, to a Trx dimer (FIG. 16, lane 3). Storage of Trx without DTT for 90 days at 4° resulted in almost complete conversion to the Trx dimer (FIG. 16, lane 4). Treatment of 7-day aged Trx (FIG. 17, lane 2) with 2-mercaptoethanol resulted in the reappearance of the fresh Trx banding pattern, except for the 8.1-kDa band, which did not reappear (FIG. 17, lane 3). Loss of the smaller bands and dimer formation was seen when Trx was treated with diamide, a protein thiol oxidizing agent (Kosower N S et al., *Methods Enzymol.*, 251:123–132, 1995) (FIG. 17, lane 5). The formation of Trx dimer following diamide treatment was also confirmed by gel permeation chromatography (results are not shown). $H_2O_2$ treatment of Trx also caused dimerization but produced a different banding pattern to that produced by diamide (FIG. 17, lane 6). Treatment of Trx with NEM, a thiol alkylating agent (Gilbert H F, *Methods Enzymol.*, 251:8–30, 1995), gave a single band with a slightly elevated apparent molecular weight, but no dimer formation (FIG. 17, lane 4). Treatment of 7 day aged Trx with NEM produced both the higher molecular weight band as in FIG. 17, lane 4, and the bands illustrated in FIG. 17, lane 2 (data not shown), suggesting that in the aged Trx not all the sulthydryls are available for covalent modification. None of the changes caused by NEM were reversed with 2-mercaptoethanol treatment (data not shown). 2-Mercaptoethanol reversed Trx dimer formation caused by both diamide and $H_2O_2$, treatment (FIG. 17, lanes 7 and 8) but was less effective at reversing changes in the monomeric banding pattern of Trx produced by $H_2O_2$, (FIG. 17, lane 8).

Freshly prepared C73S Trx and C32S/C35S Trx showed fewer bands than wild type Trx (FIG. 18, lanes 2 and 3, compared with lane 1). Treatment of C32S/C35S Trx with diamide resulted in the formation of a 23-kDa dimer (FIG. 18, lane 6). Treatment of C7')S Trx with diamide caused the bands to coalesce into a single band of around 10 kDa, but there was no 23-kDa dimer formed (FIG. 18, lane 4). The effects of diamide on C37S and 02S/05S were reversed by treatment with DTT (FIG. 18, lanes 5 and 7).

4.6.2.8 Discussion

The study shows that human recombinant Trx undergoes at least 2 levels of spontaneous and induced oxidative transformation. The first oxidation occurs spontaneously within a few days to a form(s) that can no longer stimulate cell growth but remains a substrate for thioredoxin reductase. The slower oxidation occurs over a period of weeks, or can be induced by the thiol oxidizing agent diamide, and leads to a disulfide bonded homodimer which not only fails to stimulate cell growth but is a poor substrate for thioredoxin reductase. The fact that similar changes in Trx can be induced by chemical oxidation, are protected against by catalase and are reversed by the thiol reducing agent DTT is consistent with the interpretation that the changes in Trx are due to oxidation. $Cys^{73}$ appears to play a critical role in both levels of oxidant-induced inactivation since C73S does not lose the biological activity or its ability to act as a substrate for thioredoxin reductase upon aging.

We have shown by SDS-PAGE that fresh human recombinant Trx can exist in at least five different states, which probably reflect the fully reduced state of the protein as well as different intramolecular disulfide bonded states due to the five cysteine residues present in the protein. While the specific nature of these intramolecular disulfide bonds is not known, it is likely that some, at least, are due to non-natural disulfide bonded structures which form during denaturation and the oxidizing conditions of extended electrophoresis (Creighton T E, *Methods Enzymol.*, 107:305–329, 1984). The observation that C37S and C32S/C35S exhibit a simpler banding pattern than wild-type Trx upon SDS-PAGE also suggests that the banding pattern is due to disulfide bond formation. X-ray structural analysis indicates that in addition to a disulfide bond between $Cys^{32}$ and $Cys^{35}$, the only other intramolecular disulfide bond that could form in the nondenatured Trx is between $Cys^{73}$ and $Cys^{32}$ although even this would require a different conformation of the protein (Weichsel A. et al., *Structure* 4:735–751, 1996). With the exception of a possible slight modification in $Cys^{69}$ there is no evidence that $Cys^{32}$, $Cys^{35}$ or $Cys^{62}$ are oxidized in Trx crystals formed in the presence of 5 mM DTT (Weichsel A. et al., Structure 4:735–751, 1996). The fact that treatment of Trx with NEM produces only one band implies that prior to denaturation and electrophoresis fresh Trx exists as a single species. The number of free thiols in fresh Trx was determined to be 4.5 to 4.6/molecule by Ellman's reagent (Ellman G L, *Arch. Biochem. Biophys.*, 82:70–77, 1959) (data not shown), indicating that all five cysteines are in the sulfhydryl form. Treatment of NEM-alkylated Trx with oxidizing or reducing agents produces no change in the banding pattern (data not shown), which is further evidence that all 5 sulfhydryls have been alkylated. Oxidation of cysteines to sulfenic or sulfinic acids is unlikely to occur spontaneously (Claiborne A et al., *FASEB J* 7:1483–1490, 1993). It is noteworthy that $H_2O_2$ treatment of Trx gives rise to a different monomeric banding pattern than that of spontaneously oxidized Trx. The original monomeric banding pattern is also not regenerated by treatment with DTT. As has been previously suggested for NADH peroxidase (Poole L B et al., *J. Biol. Chem.*, 264:12330–12338, 1989), we speculate that $H_2O_2$ oxidizes the cysteines to sulfenic acids and to the irreversible sulfinic or sulfonic acid states.

During the same time interval that there was a loss of the growth stimulating activity of Trx, there was a shift of the electrophoretic banding pattern. There was a collapse of the banding pattern with loss of some of the Trx monomeric bands over 7 days, suggesting that Trx may be undergoing "native" intramolecular disulfide bond formation prior to electrophoresis, which prevents the formation of random disulfidebond formation seen with denaturation and electrophoresis of fresh Trx. A similar phenomena has been observed with bovine pancreatic trypsin inhibitor (Creighton T E, *Methods Enzymol.*, 107:305–329, 1984; Weissman J S et al., *Science* 253:1386–1393, 1995). Alkylation of aged Trx with NEM gave more than one protein product, indicating that aged Trx exists in multiple forms and not all the sulfhydryls are available for reaction. Since C73S does not undergo a similar shift in banding pattern and does not undergo loss of growth stimulating activity, it can be assumed that $Cys^{73}$ is involved in this intramolecular disulfide bond formation, perhaps with $Cys^{32}$ (FIG. 19). Thus, spontaneous aging of Trx over a few days results in the inability of Trx to stimulate cell growth, although Trx is still a substrate for reduction by thioredoxin reductase. Analysis of the X-ray structure of Trx shows that $Cys^{73}$ is by far the most accessible cysteine residue and possibly the most reactive (Page D L, *Am. J Surg. Pathol.*, 15:334–349, 1991).

If a solution of Trx is left long enough, or upon treatment with a strong oxidizing agent such as diamide or $H_2O_2$, there is formation of a 23-kDa Trx homodimer. Reduction of the Trx dimer by thioredoxin reductase is slow and delayed, and is stimulated by low concentrations of fresh Trx, suggesting there may be an autocatalytic process. A similar conclusion was reached by Ren X et al., *Biochem.*, 32:9701–9705, 1993. Formation of the Trx homodimer appears to involve the $Cys^{73}$ residue since C73S, where $Cys^{73}$ is replaced with serine, does not undergo oxidation-induced homodimer formation as do Trx and C32S/C35S. Ren X et al., *Biochem.*, 32:9701–9705, 1993 have shown C73S does not undergo oxidative homodimer formation induced by selenodithioglutathione. We recently reported the X-ray crystal structure of Trx and identified a largely hydrophobic dimer forming interface that is stabilized by a $Cys^{73}$—$Cys^{73}$ disulfide bond (Weichsel A. et al., *Structure* 4:735–751, 1996). Our observation that Trx undergoes a faster loss of activity with thioredoxin reductase in PBS versus water indicates that iron-induced oxidation or an increase in ionic strength may stabilize and enhance dimer formation, which is consistent with the hydrophobic nature of the dimer interface observed in crystals of human Trx.

The importance of the monomeric oxidative form(s) of Trx is unknown. While the structural nature is yet to be identified, it does have different biological activity in our in vitro system. Trx is secreted by cells into the extracelluar environment, which is predominantly oxidizing, and might be expected to undergo monomeric oxidation. Considering its ease of formation, it is reasonable to assume that monomeric oxidation will precede oxidative homodimer formation. Whether this might be sufficient to prevent Trx from acting as a growth factor is not known. The formation of the oxidized monomer inside the cell is less likely since it still can be slowly reduced by thioredoxin reductase and the interior of the cell is highly reducing.

The physiological significance of homodimer formation is also unknown. What might be Trx homodimer has been reported in diamide-treated Jurkat cells (Sato N. et al., *J. Immunol.*, 154:3194–3203, 1995). I have observed small amounts of the Trx homodimer by immunoblotting of untreated MCF-7 breast cancer and other cell lysates. It is intriguing to speculate that formation of an oxidized Trx monomer or homodimer in response to intracellular oxidants such as $H_2O_2$ might be a way mammalian cells detect oxidant formation. Trx is believed to exist in normal cells at concentrations from 1 to 10 $\mu$M (Luthman M. et al., *Biochem.*, 21:6628–6633, 1982; Berggren M. et al., *Anti-cancer Res.* (in press)), though in selected tissues and specific cell compartments this value could be much higher. It is therefore not unreasonable to assume that Trx will undergo homodimer formation in vivo. As I observed with the enhanced inactivation of Trx in phosphate buffered saline, I expect dimer formation to precede faster in vivo than observed in vitro in water. Whether dimer formation in vivo would prevent the faster oxidation to an intramolecular form is unknown. The slow autocatalytic reduction of the Trx homodimer to the monomer would be a way to restore the cell to normal operating conditions after the induction of oxidative stress.

In summary, we have found that human recombinant Trx undergoes relatively rapid (over a few days) spontaneous and oxidant-induced conversion to a form(s) that does not stimulate cell proliferation, but is still a substrate for reduction by thioredoxin reductase. There is much slower (over a period of weeks) spontaneous oxidation of Trx to a Cys73-stabilized homodimer form that is not a substrate for thioredoxin reductase and that also does not stimulate cell proliferation. Both conversions can be reversed by treatment with the thiol reducing agent DTT, and both appear to involve the $Cys^{73}$ residue. A Cys73→Ser mutant Trx, which stimulates cell proliferation and is as effective a substrate for thioredoxin reductase as Trx, did not show age or oxidation-induced loss of these activities. Thus, with time Trx gradually loses its ability to stimulate cell proliferation and to be a substrate for thioredoxin reductase, unlike the $Cys^{73}$→Ser mutant Trx, which retains these activities with no loss. Thus, $Cys^{73}$ is not critical for biological activity but may play a critical role in the oxidative regulation of Trx activity.

4.7 Reducing Inhibition of Apoptosis in Tumor Cells that Over-Express Thioredoxin The redox protein thioredoxin plays an important role in controlling cancer cell growth through regulation of DNA synthesis and transcription factor activity. Thioredoxin is overexpressed by a number of human primary cancers and its expression is decreased during dexamethasone-induced apoptosis of mouse WEHI7.2 thymoma cells. We examined the ability of WEHI7.2 cells stably transfected with human thioredoxin cDNA showing increased levels of cytoplasmic thioredoxin to undergo apoptosis in vitro and in vivo. The cells were protected from apoptosis induced by dexamethasone, staurosporine, etoposide, and thapsigargin, but not by N-acetyl-sphingosine. When inoculated into severe combined immunodeficient mice, the trx-transfected cells formed tumors that showed increased growth compared to wild-type, as well as bcl-2-transfected, WEHI7.2 cells. The trx- and bcl-2-transfected cell tumors both showed less spontaneous apoptosis than tumors formed by the wild-type cells. Unlike tumors formed by the wild-type and bcl-2-transfected WEHI7.2 cells, trx-transfected cell tumors did not show growth inhibition upon treatment with dexamethasone. This study suggests that increased thioredoxin expression in human cancers may result in an increased tumor growth through inhibition of spontaneous apoptosis and a decrease in the sensitivity of the tumor to drug-induced apoptosis.

Trx is a low molecular weight redox protein found in both prokaryotic and eukaryotic cells (Holmgren, A. *J. Biol. Chem.*, 264:13963–13966, 1989). The cysteine residues at the conserved $Cys^{32}$-Gly-Pro-$Cys^{35}$-Lys active site of Trx undergo reversible oxidation-reduction catalyzed by the NADPH-dependent selenium-containing flavoprotein Trx reductase (Luthman, M., et al., *Biochemistry*, 21:6628–6633, 1982). Human Trx is a protein of $M_r$ 11,500 with 27% of amino acid identity to *Escherichia coli* but containing three additional Cys residues not found in bacterial Trx that give the human protein unique biological properties (Gasdaska, P. Y. et al., *Biochem. Biophys. Acta*, 1218:292–296, 1994). Trx was originally studied for its ability to act as a reducing cofactor for ribonucleotide reductase, the first unique step in DNA synthesis (Laurent, T. C. et al., *J. Biol. Chem.*, 239:3436–3444, 1964). More recently, Trx has been shown to exert redox control over a number of transcription factors, including nuclear factor κB (Matthews, J. R., et. al., *Nucleic Acids Res.*, 20:3821–3830, 1992), transcription factor IIIC (Cromlish, J. A. et al., *J. Biol. Chem.*, 264:18100–18109, 1989), BZLF1 (Bannister, A. J. et al., *Oncogene*, 6:1243–1250, 1991), and the glucocorticoid receptor (Grippo, J. F. et al., *J. Biol Chem.*, 258:13658–13664, 1983), and indirectly, through nuclear redox factor Ref-1/HAPE, Trx can regulate AP-1 (Fos/Jun heterodimer; Abate, C. et al., *Science* (Washington, D.C.), 249:1157–1161, 1990).

Trx is also a growth factor with a unique mechanism of action. Human Trx stimulates the proliferation of both normal fibroblasts and a wide variety of human solid and leukemic cancer cell lines (Powis, G. et al., *Oncol. Res.*, 6:539–544, 1994; Oblong, J. E. et al., *J. Biol. Chem.*, 269:11714–11720, 1994). Redox activity is essential for growth stimulation by Trx, and mutant redox-inactive forms of Trx lacking the active site $Cys^{32}$ and $Cys^{35}$ residues are devoid of growth stimulating activity (Oblong, J. E. et al., *J. Biol Chem.*, 269:11714–11720, 1994). Studies with $^{125}$I-labeled Trx have revealed no high-affinity binding sites that might suggest receptors for Trx on the surface of cancer cells (Gasdaska, J. R. et al., *Cell Growth Differ.*, 6:1643–1650, 1995). Trx appears to stimulate cell proliferation by increasing the sensitivity of the cells to growth factors secreted by the cells themselves (Gasdaska, J. R. et al., *Cell Growth Differ.*, 6:1643–1650, 1995).

It has been found that Trx mRNA is elevated compared to paired normal tissue in almost half of the human primary lung and colon tumors we examined (Gasdaska, P. Y. et al., *Biochem. Biophys. Acta*, 1218:292–296, 1994; Berggren, M. et al., *Anticancer Res.*, 16:3459–3466, 1996). Other studies have found increased Trx in human neoplastic cervical squamous epithelium cells and hepatocellular carcinoma (Fujii, S. et al., *Cancer* (Phila.), 68:1583–1591, 1991; Kawahara, N. et al., *Cancer Res.*, 56:5330–5333, 1996). It has recently been shown that human breast cancer cells transfected with a dominant negative, redox-inactive mutant Trx show reduced anchorage-independent growth in vitro and an almost complete inhibition of tumor formation in vivo (Gallegos, A. et al., *Cancer Res.*, 56:5765–5770, 1996). Thus, Trx overexpression may be a factor in the growth of some human cancers.

It has previously been reported that Trx gene expression is decreased during dexamethasone-induced apoptosis of mouse thymoma-derived WEHI7.2 cells (Briehl, M. M. et al., *Cell Death Differ.*, 2:41–46, 1995). To further study the effects of Trx on apoptosis, in this study we stably transfected WEHI7.2 cells with human Trx cDNA and examined the effects on both spontaneous and drug-induced apoptosis in vitro and with the cells growing in Scid mice.

4.7.1 Materials and Methods 4.7.1.1 Cells

Human wild-type Trx cDNA was prepared as described previously, cloned into the NotI site of the pDC304neo mammalian transfection vector (Gallegos, A. et al., *Cancer Res.*, 56:5765–5770, 1996) and transfected by electroporation into mouse WEHI7.2 thymoma-derived cells (Harris, A. W. et al., *J. Immunol*, 110:431–438, 1973). Transfected cells were maintained at culture densities up to $10^6$ cells/ml in DMEM containing 10% fetal bovine serum supplemented with 800 μg/ml G418 sulfate. All studies were conducted on clonal lines between passages 3 and 20. Stably transfected bcl-2 WEHI7.2 cells (W.Hbl2 cells) were obtained from Dr. Roger Miesfeld (University of Arizona, Tucson, Ariz.; Lam, M. et al., *Proc. Natl. Acad. Sci. USA*, 91:6569–6573, 1994). Drugs were added at a culture density of $1\times10^5$ to $2\times10^5$ cells/ml. Stock solutions (10 mm) of dexamethasone were prepared in ethanol, whereas staurosporine, etoposide, thapsigargin, and N-acetyl-sphingosine were prepared in DMSO. Further dilutions were made using culture medium.

4.7.1.2 mRNA Expression

Northern blot hybridization analysis was performed as described previously using a full-length [α-$^{32}$P]dCTP-labeled human Trx cDNA probe (Gasdaska P Y, et al., *Biochem. Biophys. Acta.*, 1218.:292–296, 1994). Blots were quantified using a Molecular Dynamics PhosphorImager.

4.7.1.3 Glucocorticoid Receptors

The level of functional glucocorticoid receptors was assessed using a transient contransfection of cells with a glucocorticoid response element/chloramphenicol acetyltransferase ("CAT") reporter plasmid (pmmCAT; Rundlett, S. E. et al., *Exp. Cell Res.*, 203:214–221, 1992) and β-galactosidase. After a 22-h recovery period, the cells were treated with 1 μM desamethasone, and CAT protein was measured after an additional 24 hr. using a CAT ELISA (Boehringer Mannheim, Indianapolis, Ind.). An aliquot of the transfected cells was stained for β-galactosidase activity and CAT activity normalized for transfection efficiency.

4.7.1.4 Apoptosis

Apoptosis was measured by an ELISA for histone-associated DNA fragments (Leist, M. et al., *Biochemica.*, 11:20–22, 1994), by morphology and by flow cytometry (Philpott, N. H. et al., *Blood*, 6:2244–2251, 1996). The criteria used for the morphological identification of apoptotic cells included condensation and margination of the chromatin with the formation of crescents, cell shrinkage, increased staining, nuclear fragmentation, cytuplasmic vacuolization, and apoptotic body formation. Cells were incubated with 20 μg/ml 7-amino actinomycin D for 30 min at 4° C. before being analyzed by flow cytometry.

4.7.1.5 Immunofluorescence Staining

Cells were centrifuged onto 0.17-mm-thick quartz coverslips, air dried for 10 min, fixed with 4% methanol-free formaldehyde for 20 min at room temperature, washed for 15 min in PBS, pH 7.2, and permeabilized with 100% methanol at −20° C. for 6 min. The coverslips were then stored at −20° C. until immunostaining, when they were allowed to come to room temperature and blocked with 1% BSA in PBS. This was followed by a 1:10 dilution of goat serum in PBS, before reacting for 1 h with a 1:100 dilution of immunoaffinity purified rabbit antihuman Trx polyclonal antibody (Berggren, M. et al., *Anticancer Res.*, 16:3459–3466, 1996). After being washed with PBS, the coverslips were exposed to a 1:100 dilution of goat antirabbit biotinylated IgG for h, washed with PBS, exposed to a 1:50 dilution of fluorescein streptavidin fluorochrome, and again washed with PBS. Cells were examined using a Leica TCS-4D laser scanning confocal microscope with an excitation wavelength of 488 nm. For subcellular localization studies of Trx, Cy5 (indodicarbocyanine) streptavidin was used as the fluorochrome, followed by digestion for 1 h at room temperature with 100 μg/ml RNase A and DNA stained with 25 nM YOYO-1 iodide for 10 min. Cells were then examined by laser scanning confocal microscopy at excitations of 488 nm (YOYO-1) and 647 nm (Cy5). Relative fluorescence intensities of groups of 20 cells were measured at the same laser power, photomultiplier tube voltage, and line averaging setting as gray level intensities using SigmaScan software (Jandel Scientific, Corte Madera, Calif.). Because the transfected cells exhibited an uneven distribution of fluorescent staining, a template of a regular array of dots was placed over the image, and multiple (up to 90) nuclear and cytoplasmic measurements were made.

4.7.1.6 In Vivo Tumor Growth

Tumor formation by wild-type and transfected WEHI7.2 cells was studied by injecting $2 \times 10^7$ cells in 0.1 ml of matrigel s.c. into the flanks of groups of 20 female Scid mice. Tumor volume was measured with calipers, and mice were euthanized when the tumor volume exceeded 2 cm$^3$. Nine days after tumor cell injection, 10 mice from each group were injected i.p. with 1 mg/kg/day dexamethasone in 10% ethanol in 0.9% NaCl. Control mice were injected with vehicle alone. On day 14, three mice from each group were euthanized with $CO_2$ and the tumors were excised and immediately fixed in glutaraldehyde.

4.7.1.7 Preparation of Tissue for Bright-Field Examination

The glutaraldehyde-fixed tissue was postfixed in osmium tetroxide, dehydrated in a graded series of alcohols, and embedded in epoxy resin. One-μm-thick sections were prepared and stained with toluidine blue for bright-field examination.

4.7.2 Results

WEHI7.2 cells were stably transfected with human Trx cDNA in the pDC304neo mammalian transfection vector. I examined multiple clones and found the maximal increase in Trc mRNA compared to endogenous levels of mouse Trx mRNA, was 1.8-fold for clones Trx5 and Trx6 (FIG. 20A). As determined by immunofluorescent staining and confocal microscopy, the trx-transfected cells showed increased levels of Trx (FIG. 20B). The relative fluorescence intensity of wild-type WEHI7.2 cells (±SE; n=20) was 1.00±0.05; of Trx5 cells, 2.15±0.14 (P<0.001 compared to wild type); and of Trx6 cells, 1.87±0.11 (P<0.001 compared to wild type). Trx-like fluorescent staining was observed in the nucleus as well as the cytoplasm of the cells (FIG. 20C). In the wild-type cells, 60.1±5.1% of the fluorescent staining was in the nucleus, in the Trx5 cells it was 59.8±2.5%, and in the Trx6 cells it was 36.1±1.8%.

Compared to both wild-type or vector-alone-transfected cells, the trx-transfected WEHI7.2 cells were resistant to apoptosis induced by 1 μM dexamethasone as measured by histone-associated DNA fragmentation (FIG. 21A) or by flow cytometry (FIG. 21B). Histological examination of the WEHI7.2 cells revealed a classic apoptotic morphology in response to dexamethasone. However, only a small fraction of the cells undergo apoptosis at any one time, and they rapidly progress to fragmented cells. For this reason, results are expressed as relative apoptosis rather than percentage of apoptotic cells, Glucocorticoid receptor activity measured using a glucocorticoid receptor/CAT reporter plasmid was not decreased in the trx-transfected cells (Results of three studies not shown). I also studied the effect of trx transfection on other agents known to induce apoptosis (Table 5). Compared to vector-alone-transfected cells, trx-transfected cells were resistant to apoptosis induced by staurosporine, a general kinase inhibitor (Kondo, Y. et al., *Cancer Res.*, 55:2021–2023, 1995); by a cell-permeant sphingosine analogue, N-acetyl sphingosine (Pushkareva, M. et al., *Immunol. Today*, 16:294–297, 1995); by thapsigargin, which blocks the uptake of intracellular $Ca^{2+}$ resulting in an increase in intracellular free $Ca^{2+}$ concentration (Lam, M. et al., *Proc. Natl. Acad Sci. USA*, 91:6569–6573, 1994); and by etoposide, a topoisomerase II inhibitor (Onishi, Y. et al., *Biochem. Biophys. Acta.*, 1175:147–154, 1993). WEHI7.2 cells transfected with the bcl-2 antiapoptotic proto-oncogene (W.HB 12 cells) showed a similar pattern of protection against apoptosis induced by the various agents as did the trx-transfected cells (Table 5).

TABLE 5

Effect of Trx and Bcl-2 Transfection
On Apoptosis Induced by Different Agents
pDC304neo vector-alone-transfected WEHI7.2 cells (Neo), bcl-2-transfected WEHI7.2 cells (W.Hb12), and Trx5 and Trx6 trx-transfected WEHI7.2 cells were treated with 1 μM dexamethasone for 48 h, 100 nM staurosporine for 21 hr., 100 μM N-acetyl-sphingosine for 24 hr., 1 μM etoposide for 15 hr., or 50 nM thapsigargin for 24 hr. The times were determined to be optimum for detecting apoptosis with each agent. Apoptosis was measured by flow cytometry as in FIG. 21B. Relative apoptosis is expressed as the ratio of the sum of regions R2 and R3 (early and late apoptotic cells, respectively) divided by region RI (live nonapoptotic cells) normalized to the ratio for vehicle treated vector-alone transfected cells. Values are the mean of 3 determinations ± SE. Statistical analysis was by linear regression with indicator values for drugs and cells using the Stata statistical package (Stat Corp., College Station, TX).

Relative Apoptosis

|  | Neo | Trx5[a] | Trx6[a] | W.Hb 12[a] |
|---|---|---|---|---|
| Dexamethasone | 19.2 ± 0.6 | 4.4 ± 0.7 | 7.7 ± 1.2 | 0.7 ± 0.0 |
| Staurosporine | 58.3 ± 9.8 | 5.3 ± 0.0 | 9.9 ± 1.1 | 4.8 ± 0.7 |
| N-Acetyl-sphingosine | 58.8 ± 7.1 | 11.1 ± 9.8 | 22.6 ± 4.5 | 5.5 ± 1.3 |
| Etoposide | 162.5 ± 12.1 | 6.0 ± 0.6 | 20.9 ± 4.1 | 4.5 ± 0.7 |
| Thapsigargin | 4.3 ± 0.9 | 2.3 ± 1.8 | 1.8 ± 1.2 | 0.9 ± 0.6 I |

[a]$P < 0.05$ compared to vector-alone transfected control cells.

When inoculated into Scid mice, the trx-transfected WEHI7.2 cells formed tumors that grew more rapidly than tumors formed by either wild-type or bcl-2-transfected WEHI7.2 cells (FIG. 22A). Upon histological examination, tumors formed by the wild-type cells showed fields of apoptotic cells adjacent to fields of viable cells, as well as apoptotic cells admixed with viable-appearing cells (FIG. 22B). The cells undergoing apoptosis exhibited the classic appearance of condensed and marginated chromatin, some in the form of crescents, and a dense cytoplasm accompanied by vacuolization. The trx-transfected WEHI7.2 cell tumors showed minimal numbers of cells undergoing apoptosis scattered throughout the tumor mass. Tumors formed by bcl-2-transfected WEHI7.2 cells also showed very few cells undergoing apoptosis (not shown). Areas of necrosis were seen in wild-type, trx-transfected, and bcl-2-transfected cell tumors, usually adjacent to fields of viable-appearing tumor cells or, in the case of the wild-type cells, adjacent to areas that show extensive apoptosis or next to viable-appearing cells. Treatment of the mice with dexamethasone starting at day 9 had no effect on the growth of the trx-transfected cell tumors but markedly inhibited the growth of the wild-type tumors and the bcl-2-transfected cell tumors (FIG. 22A). Histological examination revealed no evidence of increased apoptosis caused by dexamethasone treatment of wild-type, trx-transfected, or bcl-2-transfected cell tumors.

4.7.3 Discussion

WEHI7.2 cells stably transfected with human trx showed a maximal increase of 1.8-fold in Trx mRNA compared to endogenous levels of mouse Trx mRNA. This relatively low level of overexpression is similar to the experience with trx transfection of mouse NIH 3T3 cells and human MCF-7 breast cancer cells (Gallegos, A. et al., *Cancer Res.*, 56:5765–5770, 1996), suggesting that higher levels of unregulated trx expression may be toxic to cells. As determined by immunofluorescent staining and confocal microscopy, the trx-transfected cells showed approximately 2-fold increased levels of Trx. The finding that Trx is present in the cytoplasm and the nucleus of cells confirms an earlier immunohistochemical study using conventional light microscopy of cervical tumor cells that reported cytoplasmic, nuclear, or cytoplasmic and nuclear localization of Trx (Fujii, S. et al., *Cancer* (Phila.), 68:1583–1591, 1991). This is an important observation because Trx may be able to directly reduce redox-regulated nuclear transcription factors, such as AP-1 (Fox/Jun heterodimer; Abate, C. et al., *Science* (Washington, D.C.), 249:1157–1161, 1990). If Trx can enter the nucleus, it may not need other nuclear redox factors such as Ref-1/HAP1, as has been suggested (Abate, C. et al., Science (Washington, D.C.), 249:1157–1161, 1990).

The trx-transfected cells were resistant to apoptosis induced by dexamethasone. Trx has been reported to be necessary for assembly of the glucocorticoid receptor (Grippo, J. F. et al., *J. Biol. Chem.*, 258:13658–13664, 1983). However, glucocorticoid receptor activity was not decreased in the transfected cells, suggesting that the effects of Trx on apoptosis appear to lie downstream of the glucocorticoid receptor. The trx-transfected cells also showed resistance to apoptosis induced by staurosporine etoposide, N-acetyl sphingosine, and thapsigargin. Exogenously added human Trx has been reported to inhibit apoptosis induced by tumor necrosis factor α in U937 human lymphoma cells (Matsuda, M. et al., *J. Immunol.*, 147:3837–3841, 1991). However, it has been found that exogenously added human Trx did not protect WEHI7.2 cells against apoptosis induced by dexamethasone (Baker, A R et al., *Cell Death Differ.*, 3:207–213, 1996). Tumor necrosis factor α and dexamethasone are thought to trigger apoptosis by different signaling pathways. It may also be that exogenous Trx is not taken up by WEHI7.2 cells. We have found that other tumor cells take up Trx poorly, if at all (Gasdaska, J. R. et al., *Cell Growth Differ.*, 6:1643–1650, 1995). Clearly, an increase in intracellular Trx achieved by transfection of trx in the present study is associated with resistance of the WEHI7.2 cells to apoptosis induced by dexamethasone and other agents.

The pattern of resistance to drug-induced apoptosis caused by trx transfection is similar to that produced by transfection with the human proto-oncogene bcl-2. Bcl-2 is believed to exert its inhibitory effects upstream of the activation of the cysteine aspartate proteases cascade (caspase) responsible for the final stages of apoptosis (Shimizu, S. et al., *Oncogene.* 12:2251–2257, 1996). The protective effects of Bcl-2 against apoptosis have been suggested to involve an antioxidant mechanism (Hockenberry, D. M. et al., *Cell,* 75:241–251, 1993), although this is disputed based on the ability of Bcl-2 to block apoptosis caused by agents that are thought not to act by an oxidant mechanism (Jacobsen, M. D. et al., *EMBO J.*, 13:1899–1910, 1994) or caused by hypoxia (Jacobsen, M. D. et al., *Nature* (Lond.), 374:814–816, 1995). The antioxidants N-acetyl-cysteine, pyrrolidine dithio-carbamate. Trolox ( a water-soluble vitamin E analogue), and butylated hydroxytoluene protect rat thymocytes against drug-induced apoptosis (Wolfe, J. T. et al., *FEBS Lett.*, 352:58–62, 1994; Salgo, M. G. et al., *Arch. Biochem. Biophys.*, 333:482–488, 1996). We have previously reported that Trolox, catalase, and superoxide disimutase protect murine WEHI7.2 cells against dexamethasone-induced apoptosis (Baker, A. F. et al., *Cell Death Differ.*, 3:207–213, 1996). It is intriguing, therefore, that trx, a gene that codes for a known redox-active protein, also inhibits apoptosis. The mechanism by which Trx inhibits apoptosis remains to be established, but its pattern of of antiapoptotic activity similar to Bcl-2 suggests that it also may act upstream of the cysteine proteases.

WEHI7.2 cells transfected with trx formed tumors in Scid mice that grew considerably faster than tumors formed by the wild-type parental cells or by bcl-2-transfected cells. This may be due, in part, to a decreased rate of spontaneous apoptosis that occurred in the trx-transfected cell tumors. High levels of Bcl-2 have been found in a wide variety of human cancers (Reed, J. C. et al., *J. Cell. Biochem.*, 60:23–32, 1996). Although transfection with bcl-2 is known to confer resistance to apoptosis induced by anticancer drugs and radiation, the effects of bcl-2 on tumor growth are less clear. Transfection with bcl-2 gives a survival advantage to cells in culture (Maeyama, Y. *Kurume Med. J.*, 42:291–297, 1995). Transgenic mice overexpressing Bcl-2 under transcriptional regulation of the immunoglobulin heavy chain enhancer develop benign lymphoma that eventually progresses to high-grade malignant disease (McDonnell, T. J. et al., *Nature* (Lond.), 349:254–256, 1991). This suggests that bcl-2 also provides a survival advantage to cells in vivo but that an additional change, most frequently rearrangement of myc (McDonnell, T. J. et al., *Nature* (Lond.), 349:254–256, 1991), is necessary for tumor growth. Our studies using WEHI7.2 thymoma cells show that bcl-2-transfected cells formed tumors that grew faster than tumors formed by wild-type WEHI7.2 cells. This may be due to a reduction in the rate of spontaneous apoptosis observed in the bcl-2 transfected cell tumors compared to the wild-type tumors. It was not possible to distinguish a difference in the rates of spontaneous apoptosis between the trx and bcl-2-transfected cell tumors. Paradoxically, the bcl-2-transfected cell tumors still showed growth inhibition by high-dose dexamethasone treatment, as did wild-type cell tumors. There was no evidence for increased apoptosis caused by dexamethasone treatment of wild-type, trx-transfected, or bcl-2-transfected cell tumors, so the possibility remains that in vivo dexamethasone does not inhibit tumor growth in vivo by a mechanism that involves increasing the rate of apoptosis.

The results of this study and our previous work (Gallegos, A. et al., *Cancer Res.,* 56:5765–5770, 1996) suggest that the Trx system offers a novel target for agents to promote apoptosis and inhibit tumor growth, as well as to reverse the drug resistance of some cancers It is interesting, therefore, that some 2-imidazolyl disulfide inhibitors of Trx (Kuperus, M. et al., *Proc. Am. Assoc. Cancer Res.*, 36:426, 1995) have been shown to induce apoptosis in cancer cells (Powis, G. et al., *Anticancer Drugs,* 7 (Suppl. 3):121126, 1996) and, in animal studies, to have antitumor effects (Powis, G. et al., *Anticancer Drugs*, 7 (Suppl. 3):121–126, 1996).

In summary, it has been shown that transfection with trx, a gene found to be overexpressed in a number of human cancers, can inhibit apoptosis of cancer cells in culture included by a variety of agents. In animals, the trx-transfected cancer cells show an increased growth, decreased spontaneous apoptosis, and decreased sensitivity to apoptosis induced by dexamethasone. If similar effects occur in patient tumors, then trx could be a new human proto-oncogene.

4.8 Thioredoxin, a Putative Oncogene Product, is Over-Expressed in Gastric Carcinoma and Associated with Increased and Decreased Apoptosis Human thioredoxin is a putative oncogene that may confer both a growth and survival advantage to tumor cells. Over-expressed thioredoxin mRNA has been found in both primary human lung and colorectal cancers. To determine the intratumor distribution and amount of thioredoxin protein in human primary tumors and to determine if its overexpression is related to proliferation or apoptosis, I studied primary human gastric carcinoma samples. An immunohistochemical assay for thioredoxin in paraffin embedded blocks was developed. Ten patients were studied with primary high risk gastric carcinoma. To relate thioredoxin protein overexpression to apoptosis I utilized a paraffin based in situ assay (Tunel) and to delineate proliferation we utilized the nuclear proliferation antigen detected by Ki67. In this survey I found thioredoxin was localized to tumor cells and overexpressed compared to normal gastric mucosa in 8 of 10 gastric carcinomas. The thioredoxin was found at high levels in 5 of the 8 overexpressing carcinomas. The overexpression of thioredoxin was typically found in both a nuclear and cytoplasmic location in the neoplastic cells. There was a significant positive correlation (P=0.0061) with cancer cell proliferation measured by Ki67. There was a significant negative correlation (P=0.0001) with apoptosis measured by the Tunel assay. Thus, human primary gastric tumors that are highly expressive of thioredoxin have both a higher proliferative rate and a lower rate of spontaneous apoptosis than tumors that do not express thioredoxin. Whether this thioredoxin-related combined growth and survival advantage translates into poor clinical outcome remains to be determined.

Thioredoxins are low molecular weight redox proteins found in both prokaryotic and eukaryotic cells (Holmgren, A. 1989. *J. Biol. Chem.*, 264:13963–13966). The cysteine (Cys) residues at the conserved -Cys-Gly-Pro-Cys-Lys active site of thioredoxin undergo reversible oxidation-reduction catalyzed by the NADPH-dependent selenium containing flavoprotein thioredoxin reductase (Luthman, M. et al., *Biochem.*, 21:6628–6633, 1982). Human thioredoxin is an 11.5 kDa protein, with 27% amino acid identity to *E. coli* thioredoxin. It contains 3 additional Cys residues not found in bacterial thioredoxin that give it unique biological properties (Gasdaska, P. Y. et al., *Biochem. Biophys. Acta.*, 1218:292–296, 1994).

Thioredoxin was first studied for its ability to act as reducing cofactor for ribonucleotide reductase, the first unique step in DNA synthesis (Laurent, T. C. et al., *I. Biol. Chem.*, 239:3436–3444, 1964). More recently thioredoxin has been shown to exert redox control over a number of transcription factors, including NF-KB (Matthews, J. R. et al., *Nucl. Acids Res.*, 20:3821–3830, 1992), TFIHC (Cromlish, J. A. et al., *J. Biol. Chem.*, 264:18100–18109, 1989), BZLF1 (Bannister, A. J. et al., *Oncogene*, 6:1243–1250, 1991), the glucocorticoid receptor (Grippo, J. F. et al., *J. Biol. Chem.*, 258:13658–13664, 1983) and, indirectly through another redox factor Ref-1, AP-1 (Fos/Jun heterodimer) (Bannister, A. J. et al., *Oncogene*, 6:1243–1250, 1991). Thioredoxin modulates the binding of the transcription factors to DNA and thus, regulates gene transcription.

Thioredoxin is also a growth factor with a unique mechanism of action. The predicted amino acid sequence of thioredoxin is identical to that of a previously identified growth factor secreted by HTLV-1 transformed leukemic cell lines, called adult T-cell leukemia-derived factor (ADF) (Gasdaska, P. Y. et al., *Biochem. Biophys. Acta.*, 1218:292–296, 1994). ADF stimulates growth of lymphoid cells (Wakasugi, N. et al., *Proc. Natl. Acad. Sci. USA*, 87:8282–8286, 1990; Yodoi, J. et al., *Adv. Cancer Res.*, 57:381–411, 1991). It has been shown that human recombinant thioredoxin stimulates the proliferation of normal fibroblasts and human solid tumor cancer cells even in the absence of serum (Powis, G. et al., *Oncol. Res.*, 6:539–544, 1994; Oblong, J. E. et al., *J. Biol. Chem.*, 269:11714–11720, 1994). It does this by increasing the sensitivity of the cells to growth factors secreted by the cells themselves (Gasdaska, J. R. et al., *Cell Growth Differ.*, 6:1643–1650, 1995). For example thioredoxin at nM concentrations, as are found in human serum (Kitaoka, Y. et al., *Immunol. Lett.*, 41:155–161, 1994), increases the sensitivity of human breast cancer cells to interleukin-2 (IL-2) and basic fibroblast growth factor (bFGF) by 1000 and 100 fold, respectively (unpublished observations). The term "voitocrine",from the Greek "to help", has been coined to describe this growth stimulating activity of thioredoxin (Gasdaska, J. R. et al., *Cell Growth Differ.*, 6:1643–1650, 1995). Mutant redox-inactive forms of thioredoxin lacking the active site cysteine residues and *E. coli* thioredoxin are devoid of growth stimulating activity (Oblong, J. E. et al., *J. Biol. Chem.*, 269:11714–11720, 1994). Human thioredoxin is known to be secreted from cells by a leaderless secretory pathway (Rubartelli, A. et al., *J. Biol. Chem.*, 267:24161–24164, 1992) so that it could be acting extracellularly to stimulate cancer cell growth.

Our work has shown that thioredoxin is important for the growth, death and transformed phenotype of some human cancers. Stable transfection of normal fibroblasts with human thioredoxin cDNA (trx) increases their growth rate and transfection of human MCF-7 breast cancer cells with trx increases their colony formation in soft agarose (Gallegos, A. et al., *Cancer Res.*, 56:5765–5770, 1996). Transfection of the MCF-7 cells with a dominant negative redox inactive mutant trx causes inhibition of colony formation and almost complete inhibition of tumor formation when the cells were inoculated into Scid mice. In recent studies I have shown that stable transfection of mouse thymoma cells with human trx inhibits apoptosis induced by a variety of agents including glucocorticoid, staurosporine, N-acetylsphingosine, thapsigargin and etoposide, which is similar to the pattern of inhibition seen with the antiapoptotic oncogene bcl-2 in these cells (Baker, A. et al., *Cancer Research*, 57:5162–5167, 1996). The trx transfected cells form tumors that when inoculated in Scid mice grow more rapidly and show less spontaneous apoptosis than vector alone or bcl-2 transfected cells, and are resistant to growth inhibition by glucocorticoid (Baker, A. et al., *Cancer Research*, 57:5162–5167, 1996). These results suggest that trx offers a survival as well as a growth advantage to tumors in vivo, unlike bcl-2 which offers only a survival advantage and requires other genetic changes for tumor growth (McDonnell, T. J. et al., *Nature*, 349:254–256, 1991).

It has previously been reported that almost half of human primary lung cancers examined overexpress thioredoxin mRNA compared to normal lung tissue from the same subject (Gasdaska, P. Y. et al., *Biochem. Biophys. Acta.*, 1218:292–296, 1994). Recently it has been found that more than half of human primary colorectal tumors have elevated levels of thioredoxin mRNA, up to over 100 fold for one subject, compared to normal colonic mucosa taken from within 5 cm of the tumor from the same subject (Berggren, M. et al., *Anticancer Res.,* 16:3459–3466, 1996). In these studies, however, thioredoxin mRNA was extracted from pieces of tumor and nothing is known of its intratumor distribution, or even if the increased thioredoxin mRNA leads to an increase in thioredoxin protein. It remains to be determined if thioredoxin overexpression is related to proliferation or apoptosis in human primary tumors. These are clearly important questions that are now addressed in the present studies utilizing primary human gastric carcinoma samples.

The current study sought to develop an assay for thioredoxin in paraffin embedded blocks allowing survey of human tumors in archival tissue banks. To this end the Southwest Oncology Group (SWOG) Gastrointestinal Biology Laboratory made available a relevant archival paraffin block bank of gastric carcinomas. Furthermore, to relate thioredoxin to apoptosis I also sought to refine a paraffin-based in situ assay of apoptosis (Grogan, T. M. et al., *Automation of Immunohistochemistry*, In Weinstein, R. S. (ed); *Advances in Pathology and Laboratory Medicine*, vol. 6. St. Louis, Mosby, 1993, pp. 253–283; Grogan, T. M. et al. *Kinetic-mode, Automated Double-labeled Immounohistochemistry and In Situ Hybridization in Diagnostic Pathology, Advances in Pathology and Laboratory Medicine*, 8:79–100, 1995). Finally, to relate thioredoxin to proliferation, I utilized the previously developed assay of the nuclear proliferation antigen detected by Ki67 (Miller, T. et al., *Blood*, 83:1460–1466, 1994).

4.8.1 Methods 4.8.1.1 Patient Samples

Paraffn blocks from ten gastric carcinoma resections were studied. These pathology samples derived from ten patients on Southwest Oncology Group (SWOG) protocol 9008 (also known as intergroup study #0116). This is a study of high risk gastric carcinoma comparing gastrectomy only versus gastrectomy plus adjuvant therapy. The patients ranging in age from 42 to 75; all had previously untreated, stage II and III B gastric carcinoma. They had biopsy proven adenocarcinoma of the stomach which had a high risk for recurrences due to evidence of carcinoma extension beyond the muscularis propria and/or having lymph node involvement. Patients with Stage O, IA or any stage with M1 were not eligible. As of December 1996 this study has accrued 486 patients.

4.8.1.2 Immunohistochemistry

Five micron thick sections were deparaffinized and then subjected to antigen unmasking with one of two methods with heat plus citrate buffer a pH 6.6 or microwave plus EDTA buffer at pH 8.0 as previously described (Grogan, T. M. et al., *Automation of Immunohistochemistry*, In Weinstein, R. S. (ed); *Advances in Pathology and Laboratory Medicine*, vol. 6. St. Louis, Mosby, 1993, pp. 253–283; Grogan, T. M. et al. *Kinetic-mode, Automated Double-labeled Immounohistochemistry and In Situ Hybridization in Diagnostic Pathology, Advances in Pathology and Laboratory Medicine*, 8:79–100, 1995). The best signal to noise ratio was established by judging reactivity with cell lines known to be a high expressor of thioredoxin (A549 human lung cancer) and a low expressor of thioredoxin (SK BR3 human breast cancer) (Berggren, M. et al., *Anticancer Res.*, 16:3459–3466, 1996).

All tumor samples and control cell lines were stained using a standard immunohistochemical method as previously described (Grogan, T. M. et al., *Automation of Immunohistochemistry*, In Weinstein, R. S. (ed); *Advances in Pathology and Laboratory Medicine*, vol. 6. St. Louis, Mosby, 1993, pp. 253–283; Grogan, T. M. et al. *Kinetic-mode, Automated Double-labeled Immounohistochemistry and In Situ Hybridization in Diagnostic Pathology, Advances in Pathology and Laboratory Medicine*, 8:79–100, 1995). To obviate biotin receptor reactivity, biotin-avidin blocking was performed first. Then the primary antibody (polyclonal rabbit anti-human thioredoxin) (Berggren, M. et al., *Anticancer Res.*, 16:3459–3466, 1996) was utilized at a titer of 1/200 after titration of control cell lines. The best signal to noise ratio was found following microwaving at pH 8.0 with EDTA buffer. Sections were treated with biotinylated goat-anti-rabbit antibody and then with avidin-peroxidase complex, each for 30 minutes at 42° C. in an automated immunostainer (VMS ES, Ventana Medical Systems, Tucson, Ariz.) (Grogan, T. M. et al., *Automation of Immunohistochemistry*, In Weinstein, R. S. (ed); *Advances in Pathology and Laboratory Medicine*, vol. 6. St. Louis, Mosby, 1993, pp. 253–283; Grogan, T. M. et al. *Kinetic-mode, Automated Double-labeled Immounohistochemistry and In Situ Hybridization in Diagnostic Pathology, Advances in Pathology and Laboratory Medicine*, 8:79–100, 1995). Sections were counterstained with methyl green, dehydrated, rinsed in xylene and coverslipped.

The degree of thioredoxin expression in tumor cells was judged at 400× magnification as 4+ (very intensely positive), 3+ (moderately intensely positive), 2+ (moderate), 1+ (faint), or 0 (completely negative) throughout the sample. A single investigator (TG) was responsible for scoring all the samples.

Additional immunohistochemical assays employed antibody to proliferation antigens, Ki67 (Ventana, Tucson, Ariz.), also using the biotin-avidin labelled method after avidin blocking (Miller, T. et al., *Blood*, 83:1460–1466, 1994). The degree of Ki67 staining, again judged at 400× magnification, was classified as the percentage of nuclear positive tumor cells listed as: absent (0),>0–5% (+), 6–25% (++), 26–50(+++),>51% (++++).

4.8.1.3 Apoptosis Assay

Apoptotic cells were detected utilizing the TUNEL assay (Gavrieli, Y. et al., *J. Cell Biol.*, 119:493–501, 1992; Grasl-Kraupp, B. et al., *Hepatology*, 21:1465–1468, 1995) adapted to an automated in situ hybridization instrument (gen II, Ventana Medical Systems, Inc.). The TUNEL assay utilizes recombinant terminal deoxynucleotidyl transferase (Tdr) (GIBCO BRL) for adding homopolymer tails to the 3' ends of DNA which are more abundant in apoptotic cells (Gavrieli, Y. et al., *J. Cell Biol.*, 119:493–501, 1992; Grasl-Kraupp, B. et al.,*Hepatology*, 21:1465–1468, 1995). Biotin-16, 2'-deoxyuridine-5' triphosphate (Biotin 16-dUTP) (Boehringer-Mannheim, Indianapolis, Ind.) was the label used for terminal transferase in this DNA 3'-end labelling reaction. Avidin-Horseradish Peroxidase and 3,3'-diaminobenzidine as chromogen (Gavrieli, Y. et al., *J. Cell Biol.*, 119:493–501, 1992; Grasl-Kraupp, B. et al., *Hepatology*, 21:1465–1468, 1995).

The instrument utilized deparaffinized sections with subsequent digestion with Protease I (Ventana Medical Systems, Tucson, Ariz.) for 8 minutes VMS 1). Incubations were performed per Ventana Gen II protocol on the instrument with the final steps being as above using avidin-horse radish peroxidase and DAB detection method to visualize the apoptotic nuclei as an intense brown color (diaminobenzidine). As an enzyme control we utilized two sections from each tissue: one with Tdt enzyme and one without enzyme (negative control).

The TUNEL assay result was scored by the number of brown—apoptotic tumor nuclei per high power field (400× objective). The values were: 0 (absence of apoptotic cells),+ (>0–2/hpf),++(2–4/hpf),+++(>4–8/hpf), ++++(>8/hpf).

4.8.2 Statistical Analysis

Thioredoxin expression was correlated with Ki67 expression and with apoptosis measured by the TUNEL assay using Spearman's nonparametric rank correlation test.

4.8.3 Results

The optimum signal to noise ratio was found by using the following antigen retrieval conditions: microwaving at pH 8.0 in EDTA as tested by a high thioredoxin expressor (A 549) and low thioredoxin expressing (Sk BR3) cell line.

Immunohistochemical localization of thioredoxin (positive staining) was found in the tumor cells of 8 of 10 gastric carcinoma samples (Table 2, supra). Seven of these eight showed both nuclear and cytoplasmic staining (FIG. 23). The two cases with no tumor thioredoxin showed positive staining in the adjacent normal mucosa and are important controls, suggesting these are true, not false-negative, tumors (FIG. 24).

Among the eight thioredoxin positive gastric carcinomas there was a range of positivity from faint (+) to intense (++++) with five cases having high level thioredoxin (+++to ++++) and three having low level (+to ++) (Table 2, supra).

In all samples there was the adjacent normal mucosa where the strongest staining was found in the gastric mucosal pits (++) while faint staining was found in the superficial mucosa (+). The localization differed based on site with gastric pits showing both nuclear and cytoplasmic staining while the middle mucosa had only cytoplasmic staining (FIG. 25).

Increased levels of thioredoxin levels positively correlated with increased cell proliferation as measured by Ki67 expression (r=0.861, p=0.0061) and negatively correlated with apoptosis as measured by the Tunel assay (r=0.949, p–0.0001) (see Table 2, and FIGS. 26 and 27).

4.8.4 Discussion

An important aspect enabling this study is the development of two methodologic refinements: (Holmgren, A. 1989. *J. Biol. Chem.*, 264:13963–13966) the use of heatbased antigen unmasking methods to allow optimal, reliable measurement of thioredoxin by IHC in archival paraffin embedded tissues; and (Luthman, M., Holmgren, A. *Biochem.*, 21:6628–6633) adaptation of the Tdt based TUNEL assay to an automated procedure on an automated in situ machine. The heat-based antigen optimization of IHC entailed heating the paraffin section in 5 mM EDTA in 0.1 M TRIS, pH 8.0. The specificity of the reaction was assured by the finding of high positive signal in A549 human lung carcinoma, a known high level thioredoxin expressor as determined by prior Western blotting (Berggren, M. et al., *Anticancer Res.*, 16:3459–3466, 1996). SK BR3 breast carcinoma cells likewise served as low level expressor control also established by prior Western blotting. The gastric tumor samples themselves also served as positive and negative, same-slide controls. In particular, within the entrapped normal gastric mucosa gastric pits and mid-level mucosal cells showed thioredoxin signal while surface mucosal cells were negative. There was a clear difference in the subcellular localization of thioredoxin in normal positive gastric cells, the lower level in the pits showed cytoplasmic and scattered nuclear staining, while the higher mid-level graduation staining was typically lighter and restricted to the cytoplasm. The significance of this differential distributions is not known. Thioredoxin does not have a known nuclear localization sequence (Gasdaska, P. Y. et al., *Biochem. Biophys. Acta.*, 1218:292–296, 1994). From our IHC studies it is clear that thioredoxin is specifically located within neoplastic gastric carcinoma cells and not in stromal cells or admixed B or T lymphocytes or macrophages. The tumor cell thioredoxin density typically exceeded that of the adjacent normal mucosa. The minimal background staining and strong signal to noise in all the samples, as illustrated in FIGS. 23–27, demonstrate the refinement of the thioredoxin paraffin assay we have developed.

In this survey of 10 primary human gastric carcinomas we have determined the extent of thioredoxin overexpression and determined its localization and its relationship to proliferation and cell survival (apoptosis) status. We found thioredoxin is overexpressed, compared to normal gastric mucosa, in the malignant cells of 8 of 10 gastric carcinomas. The thioredoxin protein was found at high levels in five of the eight overexpression carcinomas. The expression was typically found in both a nuclear and cytoplasmic location in the neoplastic cells. There was a significant positive correlation (p<0.01) between increased levels of thioredoxin expression and cell proliferation measured by Ki67 expression. There was also a significant negative correlation (p<0.0001) between increased levels of thioredoxin and apoptosis measured by the TUNEL assay. Thus, human primary gastric tumors highly expressive of thioredoxin have both a higher proliferative rate and a lower rate of spontaneous apoptosis than tumors with absent or low thioredoxin (FIG. 26). This finding is consistent with our experimental observation that the stable transfection of mouse WEHI7.2 cells with human wild type thioredoxin leads to increased tumor growth rate in vivo associated with a decreased rate of spontaneous apoptosis (Baker, A. et al., *Cancer Research*, (in press) 1996). We have also found that transfection of human MCF-7 breast cancer cells with a dominant-negative redox inactive mutant thioredoxin inhibits tumor growth in vivo (McDonnell, T. J. et al., *Nature*, 349:254–256, 1991). Thus, overexpression of thioredoxin in gastric carciroma is associated with increased cell growth and cell survival giving the cells doubly immortalizing properties. Whether this will translate in patients into more aggressive tumor growth, as seen in animals with thioredoxin transfected tumor cells, and a poor prognosis remains to be determined.

There have been 2 reports of the immunohistochemical distribution of thioredoxin in human primary tumors, Fujii et al., *Cancer*, 68:1583–1591, 1991 reported that, while the squamous and glandular cells of normal human cervix showed no thioredoxin IHC, the immediate and superficial layers of cervical squamous neoplastic tissue, as well as invasive squamous cell carcinoma showed cytoplasmic and nuclear staining for thioredoxin. A study by Kawahara, N. et al., *Cancer Res.*, 56:5330–5333, 1996 has reported enhanced expression of thioredoxin in human hepatocellular carcinoma compared to adjacent non-cancerous liver, with both a nuclear and cytoplasmic localization of the staining. Thus, thioredoxin overexpression appears to be a common phenomenon among a diversity of human neoplasms.

Future studies are required to confirm the relationship between thioredoxin overexpression, increased gastric cancer proliferation and increased cell survival. The newly developed ability to simultaneously perform combined TUNEL and IHC assays on a single tissue section should allow more precise definition of the relationship of thioredoxin to cell proliferation or cell death, since the phenotype of individual apoptotic or proliferative cells may now be discerned by these double labelled assays.

Finally, correlative clinical studies are anticipated to relate thioredoxin expression, Ki67 and apoptosis index to pathogenic grade, response to chemotherapy, disease free survival or overall survival thus defining the impact of thioredoxin on human carcinomas. Our patient data on the SWOG 9008 (Intergroup 0116) study of high risk gastric carcinomas which is now ongoing and has accrued 486 gastric carcinoma patients would seem to be the ideal patient cohort to study. Now that we have developed paraffin-based assays for thioredoxin, Ki67 and Tdt apoptosis by the Tunel assay in a standardized optimized manner, the full clinical study testing the clinical impact of thioredoxin is now feasible.

All of the various publications cited above are hereby incorporated by reference in their entireties.

I claim:

1. A method of inhibiting tumor growth in vivo in a tumor cell that over-expresses thioredoxin comprising contacting said tumor cell with a cell growth inhibiting effective amount of an inhibitor of thioredoxin, said inhibitor of thioredoxin interacting with a cysteine of human thioredoxin at residue 73 of said human thioredoxin.

2. The method of claim 1, wherein said inhibitor is a 2-imidazolyl disulfide.

3. The method in claim 2, wherein said inhibitor of thioredoxin expression binds the cysteine at residue 73 of human thioredoxin.

* * * * *